United States Patent
Komatsu et al.

(10) Patent No.: US 9,399,703 B2
(45) Date of Patent: Jul. 26, 2016

(54) POLYIMIDE AND ALICYCLIC TETRACARBOXYLIC DIANHYDRIDE USED FOR PRODUCING THE SAME

(71) Applicant: JX NIPPON OIL & ENERGY CORPORATION, Chiyoda-ku, Tokyo (JP)

(72) Inventors: Shinichi Komatsu, Tokyo (JP); Rieko Fujishiro, Tokyo (JP); Miki Fujiwara, Tokyo (JP); Daisuke Watanabe, Tokyo (JP); Akira Shibashi, Tokyo (JP); Takaya Matsumoto, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 0 days.

(21) Appl. No.: 14/424,314

(22) PCT Filed: Aug. 29, 2013

(86) PCT No.: PCT/JP2013/073104
§ 371 (c)(1),
(2) Date: Feb. 26, 2015

(87) PCT Pub. No.: WO2014/034760
PCT Pub. Date: Mar. 6, 2014

(65) Prior Publication Data
US 2015/0218317 A1 Aug. 6, 2015

(30) Foreign Application Priority Data

Aug. 31, 2012 (JP) ................................ 2012-191731
Mar. 18, 2013 (JP) ................................ 2013-055804

(51) Int. Cl.
C07D 407/08 (2006.01)
C08G 73/10 (2006.01)
C07D 493/10 (2006.01)

(52) U.S. Cl.
CPC .......... *C08G 73/1067* (2013.01); *C07D 493/10* (2013.01); *C08G 73/10* (2013.01); *C08G 73/1007* (2013.01); *C08G 73/1075* (2013.01); *C08G 73/1078* (2013.01); *C07C 2103/93* (2013.01)

(58) Field of Classification Search
CPC .......... C07C 2103/93; C08G 73/1007; C08G 73/1075; C07D 493/10
See application file for complete search history.

(56) References Cited

U.S. PATENT DOCUMENTS

| 3,326,940 A | 6/1967 | Dunkel |
| 8,629,303 B2 | 1/2014 | Komatsu et al. |
| 2009/0182114 A1 | 7/2009 | Kusaka et al. |
| 2012/0310013 A1 | 12/2012 | Komatsu et al. |
| 2013/0079490 A1 | 3/2013 | Matsumoto et al. |
| 2014/0224318 A1 | 8/2014 | Komatsu et al. |

FOREIGN PATENT DOCUMENTS

| JP | H05-271409 A | 10/1993 |
| JP | H07-304868 A | 11/1995 |
| JP | 2004-18422 A | 1/2004 |
| JP | 2005-336246 A | 12/2005 |
| JP | 2008-31406 A | 2/2008 |
| JP | 2010-184898 A | 8/2010 |
| JP | 2011-162479 A | 8/2011 |
| WO | 2011/099518 A1 | 8/2011 |
| WO | 2013/021942 A1 | 2/2013 |

OTHER PUBLICATIONS

USPTO structure search, Oct. 2015.*
International Search Report dated Nov. 18, 2013, issued in International Application PCT/JP2013/073104.
Ryosuke, Kimura, Toshihiko Matsumoto, "Colorless and Thermally Stable Polymer—An Alicyclic Polyimide with Cyclopentanone Bis-spironorbornane Structure", Japanese Journal of Polymer Science and Technology, Apr. 19, 2011, vol. 68. No. 3, pp. 127 to 131.
Saishin Poriimido—Kiso to Ouyou—(Current Polyimides—Fundamentals and Applications-), newly-revised edition, NTS Inc., published in 2010, pp. 291 to 293.
Ryosuke Kimura et al. "Colorless and Thermally Stable Polymer—An Alicyclic Polyimide with Cyclopentanone Bis-spironorbornane Structure", Japanese Journal of Polymer Science and Technology, vol. 68, No. 3, pp. 127-131.
Office Action mailed Feb. 3, 2016, for Chinese Application No. 201380045721.8. (with translation).

* cited by examiner

Primary Examiner — Gregory Listvoyb
(74) Attorney, Agent, or Firm — Fitch, Even, Tabin & Flannery LLP

(57) ABSTRACT

A polyimide containing at least one of repeating units represented by the following general formulae (1) and (2):

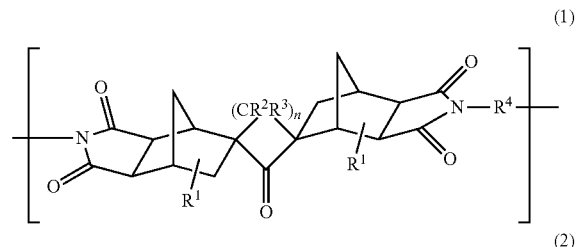

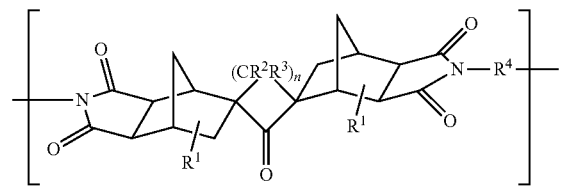

wherein the formulae (1) and (2), $R^1$, $R^2$, and $R^3$ each independently represents a hydrogen atom or the like, $R^4$ represents an aryl group having 6 to 40 carbon atoms, and n represents an integer of 0 to 12, wherein a total amount of the repeating units represented by the general formulae (1) and (2) is 90% by mole or more relative to all repeating units.

15 Claims, 25 Drawing Sheets

POLYIMIDE AND ALICYCLIC TETRACARBOXYLIC DIANHYDRIDE USED FOR PRODUCING THE SAME

CROSS-REFERENCE TO RELATED APPLICATIONS

This Application is a U.S. National Stage Application filed under 35 U.S.C. §371 of International Application PCT/JP2013/073104, filed Aug. 29, 2013, designating the United States, which claims priority from Japanese Patent Application 2012-191731, filed Aug. 31, 2012, and Japanese Patent Application 2013-055804, filed Mar. 18, 2013, the complete disclosures of which are hereby incorporated herein by reference in their entirety for all purposes.

TECHNICAL FIELD

The present invention relates to a polyimide and an alicyclic tetracarboxylic dianhydride used for producing the polyimide.

BACKGROUND ART

Recently, research and development of heat-resistant materials has been actively conducted, and polyimides have attracted attention from the viewpoints of their excellent heat resistance and excellent dimensional stability. As such a polyimide, an aromatic polyimide "Kapton" is commercially available. This aromatic polyimide is a representative organic material developed in 1960's by DuPont USA, and has a heat resistance of the highest class among heat resistant polymers. The aromatic polyimide is known as a polymer material which can withstand high temperature of about 300° C. and even harsh space environment for a long period. However, such a wholly aromatic polyimide is colored in brown, because the intramolecular charge transfer (CT) occurs between an aromatic tetracarboxylic dianhydride unit and an aromatic diamine unit. Hence, the wholly aromatic polyimide cannot be used in applications where transparency is necessary (the printable electronics application, the flexible glass alternative application, the semiconductor resist application, and the like). For this reason, to produce a polyimide which can be used in applications where transparency is necessary, alicyclic polyimides which undergo no intramolecular CT and which have high light transmittance have been researched recently.

As such an alicyclic polyimide, for example, a polyimide is known which is obtained by using a combination of trans-1, 4-cyclohexanediamine (t-CHDA) with pyromellitic anhydride (PMDA) or 3,3',4,4'-biphenyltetracarboxylic dianhydride (BPDA). The alicyclic polyimide obtained by using a combination of t-CHDA with PMDA or BPDA is also known to have an extremely low linear expansion coefficient (for example, 10 ppm/° C. for a t-CHDA/PMDA system, and 10 ppm/° C. for a t-CHDA/BPDA system) (see SAISHIN PORIIMIDO—KISO TO OUYOU—(Current Polyimides—Fundamentals and Applications—), newly-revised edition, NTS INC., 2010, PP. 291 to 293 (NPL 1)). However, trans-1,4-cyclohexanediamine (t-CHDA) used for producing such an alicyclic polyimide is a monomer which forms an extremely hard salt at the initial stage of the polymerization with PMDA or BPDA, and hence is extremely difficult to polymerize in a usual manner. Accordingly, such a polyimide is not necessarily sufficient in terms of polymerizability, and is difficult to put into practical use.

Meanwhile, as another alicyclic polyimide, for example, International Publication No. WO2011/099518 (PTL 1) discloses a polyimide having a repeating unit represented by the following general formula:

[Chem. 1]

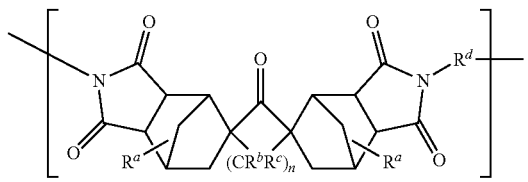

[in the formula, $R^a$, $R^b$, and $R^c$ each independently represent one selected from the group consisting of a hydrogen atom, alkyl groups having 1 to 10 carbon atoms, and a fluorine atom, $R^d$ represents an aryl group having 6 to 40 carbon atoms, and n represents an integer of 0 to 12].

CITATION LIST

Patent Literature

[PTL 1] International Publication No. WO2011/099518

Non Patent Literature

[NPL 1] SAISHIN PORIIMIDO—KISO TO OUYOU—(Current Polyimides—Fundamentals and Applications—), newly-revised edition, NTS INC., published in 2010, pp. 291 to 293

SUMMARY OF INVENTION

Technical Problem

The polyimide described in PTL 1 can be produced under ordinary production conditions, and is sufficiently highly practical. In addition, the polyimide described in PTL 1 has a high light transmittance and also a sufficiently high heat resistance. Moreover, the present inventors have found that the polyimide described in PTL 1 had a linear expansion coefficient of 19 ppm/° C. in one embodiment thereof (see Comparative Example 1 and Table 1 in DESCRIPTION of the present application), and had a suitable linear expansion coefficient sufficient to be preferably used in various applications such as the printable electronics application, the flexible glass alternative application, and the semiconductor resist application.

However, as an alicyclic polyimide used for the applications such as the printable electronics application, the flexible glass alternative application, and the semiconductor resist application, an advent of a polyimide having such a lower linear expansion coefficient that the expansion due to heat can be suppressed at a higher level have been awaited from the viewpoint that, in a step involving heating employed during the use of the polyimide, such as a step of stacking an inorganic material having a small linear expansion coefficient (CTE) on the polyimide, cracks, peeling, and the like due to a stress caused by the difference in linear expansion coefficient between the inorganic layer and the polyimide layer are more reliably prevented at a higher level.

The present invention has been made in view of the problem of the above-described conventional technology, and an object of the present invention is to provide a polyimide which is excellent in light transmittance and heat resistance and which has a sufficiently low linear expansion coefficient, and an alicyclic tetracarboxylic dianhydride used for producing the polyimide.

Solution to Problem

The present inventors have conducted intensive study to achieve the above-described object, and consequently found that, astonishingly, when a polyimide comprises repeating units having specific structures and being represented by the following general formulae (1) and (2) in an amount of 90% by mole or more relative to all repeating units, the obtained polyimide not only is sufficiently excellent in light transmittance and heat resistance, but also has a sufficiently low linear expansion coefficient. This finding has led to the completion of the present invention.

Specifically, a polyimide of the present invention is a polyimide comprising at least one of repeating units represented by the following general formulae (1) and (2):

[Chem. 2]

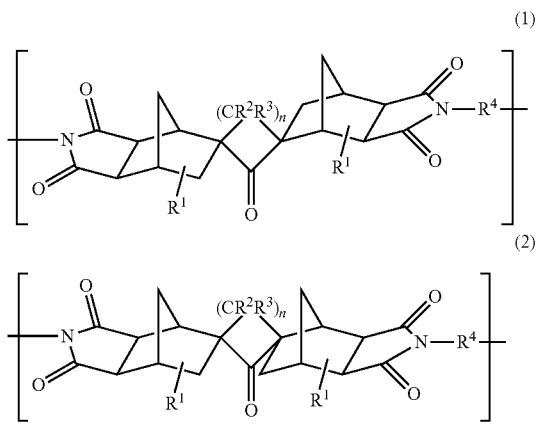

[in the formulae (1) and (2), $R^1$, $R^2$, and $R^3$ each independently represent one selected from the group consisting of a hydrogen atom, alkyl groups having 1 to 10 carbon atoms, and a fluorine atom, $R^4$ represents an aryl group having 6 to 40 carbon atoms, and n represents an integer of 0 to 12], wherein a total amount of the repeating units represented by the general formulae (1) and (2) is 90% by mole or more relative to all repeating units.

In addition, in the polyimide of the present invention, $R^4$ in the general formulae (1) and (2) is preferably one of groups represented by the following general formulae (3) to (6):

[Chem. 3]

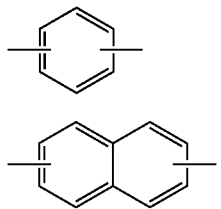

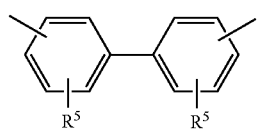

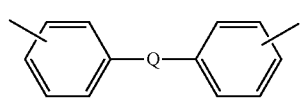

[in the formula (5), $R^5$ represents one selected from the group consisting of a hydrogen atom, a fluorine atom, a methyl group, an ethyl group, and a trifluoromethyl group, and in the formula (6), Q represents one selected from the group consisting of groups represented by the formulae: —O—, —S—, —CO—, —CONH—, —$C_6H_4$—, —COO—, —$SO_2$—, —$C(CF_3)_2$—, —$C(CH_3)_2$—, —$CH_2$—, —O—$C_6H_4$—C$(CH_3)_2$—$C_6H_4$—O—, —O—$C_6H_4$—$SO_2$—$C_6H_4$—O—, —$C(CH_3)_2$—$C_6H_4$—$C(CH_3)_2$—, —O—$C_6H_4$—$C_6H_4$—O—, and —O—$C_6H_4$—O—].

In addition, the polyimide of the present invention preferably has a linear expansion coefficient of 15 ppm/° C. or less, the linear expansion coefficient being determined by measuring change in length under a nitrogen atmosphere under a condition of a rate of temperature rise of 5° C./minute in a temperature range from 50° C. to 200° C.

Moreover, in the polyimide of the present invention, the total amount of the repeating units represented by the general formulae (1) and (2) is preferably 95 to 100% by mole relative to all the repeating units.

Meanwhile, an alicyclic tetracarboxylic dianhydride of the present invention is an alicyclic tetracarboxylic dianhydride used for producing the polyimide of the present invention, the alicyclic tetracarboxylic dianhydride comprising at least one of trans-endo-endo-norbornane-2-spiro-α-cycloalkanone-α'-spiro-2"-norbornane-5,5",6,6"-tetracarboxylic dianhydrides represented by the following general formula (7):

[Chem. 4]

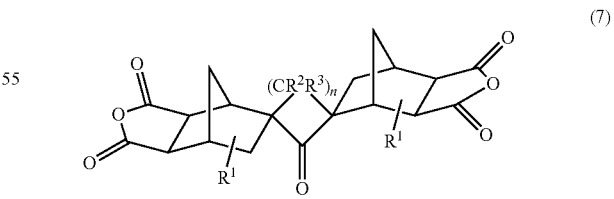

[in the formula (7), $R^1$, $R^2$, $R^3$, and n have the same meanings as those of $R^1$, $R^2$, $R^3$, and n in the general formulae (1) and (2)], and cis-endo-endo-norbornane-2-spiro-α-cycloalkanone-α'-spiro-2"-norbornane-5,5",6,6"-tetracarboxylic dianhydrides represented by the following general formula (8):

[Chem. 5]

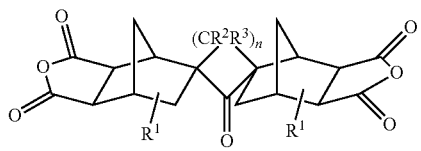

(8)

[in the formula (8), $R^1$, $R^2$, $R^3$, and n have the same meanings as those of $R^1$, $R^2$, $R^3$, and n in the general formulae (1) and (2)], wherein a total amount of the alicyclic tetracarboxylic dianhydrides represented by the general formulae (7) and (8) is 90% by mole or more.

Note that although it is not exactly clear why the polyimide of the present invention has a sufficiently low linear expansion coefficient, the present inventors speculates as follows. Specifically, the polyimide of the present invention comprises the repeating units represented by the general formulae (1) and (2) in an amount of 90% by mole or more in total. By using the repeating units at such a content ratio, the main chain of the polymer takes a so-called planar zigzag structure, and forms a higher-order structure. Actually, a molecular orbital calculation of the main chain structure (conformation) of a polymer carried out by taking as an example a polyimide comprising a repeating unit represented by the general formula (2), where $R^1$, $R^2$, and $R^3$ are each a hydrogen atom, $R^4$ is a group represented by the general formula (6), Q is represented by the formula: —CONH—, and n is 2, in an amount of 100% by mole shows that the higher-order structure of the polymer is a planar zigzag structure as shown in FIGS. 1 and 2. Note that the molecular orbital calculation can be carried out by using a personal computer of FUJITSU, model FMV-B8200, and using the MOPAC software of Chem Bio3D Ultra10. As a method for the calculation, a method can be employed in which a polyimide formed from an alicyclic tetracarboxylic dianhydride and an aromatic diamine used as monomers is drawn on Chem Bio3D Ultra10, followed by the MM2 calculation, and then the AM1 calculation. Thus, the stable structure of the polymer can be simulated by calculation. In addition, it can be seen that, while taking the structure (the planar zigzag structure as shown in FIGS. 1 and 2) determined by the molecular orbital calculation, the polyimide is oriented in-plane. Note that the present inventors speculate that the orientation state of the film is such that the planar portions of the zigzag structures as shown in FIG. 1 are staked on one another in the thickness direction (the Z direction) of the film. In addition, when the polyimide is oriented in-plane as described above, the film has a low linear expansion coefficient in the in-plane direction (XY direction: this direction is defined with the direction perpendicular to the film being defined as the Z direction, one direction perpendicular to the Z direction being defined as the X direction, and the direction perpendicular to the Z direction and the X direction being defined as the Y direction) of the film. The present inventors speculate that, for this reason, the linear expansion coefficient in the XY direction is sufficiently low, and for example when a film is produced, the film has a sufficiently low linear expansion coefficient, in the present invention. The present inventors speculate that since the polyimide comprises the repeating units represented by the general formulae (1) and (2) in an amount of 90% by mole or more, the polyimide has a planar zigzag structure, so that the sufficiently low linear expansion coefficient is exhibited in the present invention, as described above. Note that the present inventors speculate that since the linear expansion coefficient in the in-plane direction is low in the present invention, expansion of the film under a high heating temperature condition is expected to occur in the film thickness direction (the Z direction), and a stress acting in the XY direction between the film and an inorganic material having a low linear expansion coefficient is sufficiently reduced, and formation of cracks and the like are sufficiently suppressed also in stacking the inorganic layer under a high heating temperature condition. The present inventors speculate that, for this reason, the polyimide of the present invention can be suitably used in the applications such as an application where a processing step under a high temperature condition or the like is conducted.

Advantageous Effects of Invention

According to the present invention, it is possible to provide a polyimide which is excellent in light transmittance and heat resistance and which has a sufficiently low linear expansion coefficient, and an alicyclic tetracarboxylic dianhydride used for producing the polyimide.

DESCRIPTION OF EMBODIMENTS

Figure 1:
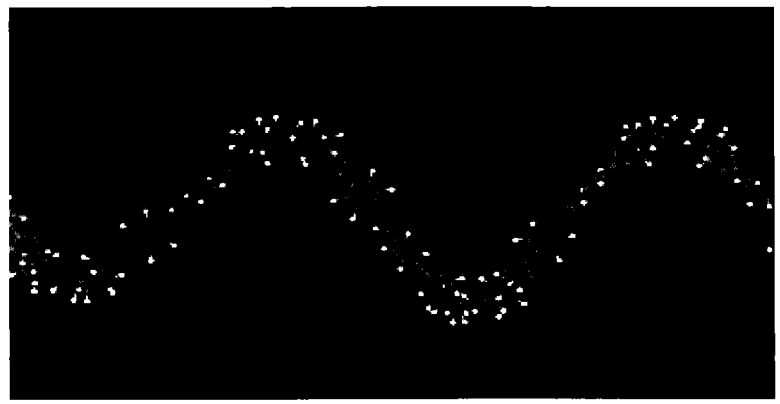
FIG. 1 is a schematic diagram obtained by theoretically calculating a main chain structure of a polyimide in a film obtained by using a preferred embodiment of a polyimide of the present invention and viewed in a direction perpendicular to the film.
Figure 2:
FIG. 2 is a schematic diagram obtained by theoretically calculating the main chain structure of the polyimide in the film obtained by using the preferred embodiment of the polyimide of the present invention and viewed in a transverse direction of the film.

Hereinafter, the present invention will be described in detail based on preferred embodiments thereof.

First, a polyimide of the present invention is described. The polyimide of the present invention is a polyimide comprising at least one of repeating units represented by the following general formulae (1) and (2):

[Chem. 6]

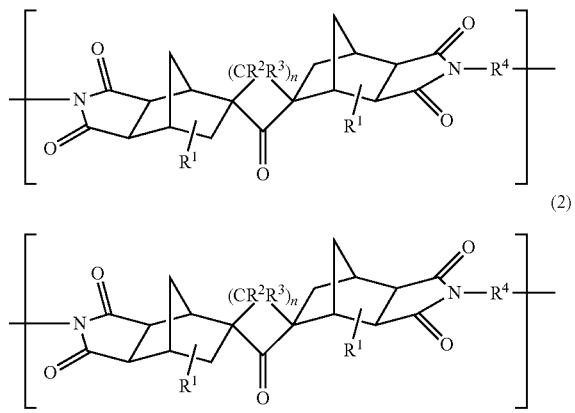

[in the formulae (1) and (2), $R^1$, $R^2$, and $R^3$ each independently represent one selected from the group consisting of a hydrogen atom, alkyl groups having 1 to 10 carbon atoms, and a fluorine atom, $R^4$ represents an aryl group having 6 to 40 carbon atoms, and n represents an integer of 0 to 12], wherein a total amount of the repeating units represented by the general formulae (1) and (2) is 90% by mole or more relative to all repeating units.

The alkyl group which can be selected as any one of $R^1$, $R^2$, and $R^3$ in the general formulae (1) and (2) is an alkyl group having 1 to 10 carbon atoms. If the number of the carbon atoms exceeds 10, the glass transition temperature is lowered, so that a film formed of the obtained polyimide cannot have a sufficient resistance to heat shock (this resistance refers to such a resistance that the quality can be sufficiently maintained even when the surrounding temperature changes to high temperature, and, for example, refers to such a resistance that, in a case where a step of stacking an inorganic layer under a high temperature condition of about 300° C. or above has to be employed, or other cases, occurrence of peeling and fracture can be sufficiently suppressed even under such a temperature condition; hereinafter, this resistance is referred to as "heat shock resistance"). In addition, the number of carbon atoms of the alkyl group which can be selected as any one of $R^1$, $R^2$, and $R^3$ is preferably 1 to 6, more preferably 1 to 5, further preferably 1 to 4, and particularly preferably 1 to 3, from the viewpoint that the purification is easier. In addition, the alkyl group which can be selected as any one of $R^1$, $R^2$, and $R^3$ may be linear or branched. Moreover, the alkyl group is more preferably a methyl group or an ethyl group from the viewpoint of ease of purification.

$R^1$, $R^2$, and $R^3$ in the general formulae (1) and (2) are each independently more preferably a hydrogen atom or an alkyl group having 1 to 10 carbon atoms from the viewpoint that a higher heat resistance can be obtained. Especially, $R^1$, $R^2$, and $R^3$ are each independently more preferably a hydrogen atom, a methyl group, an ethyl group, a n-propyl group, or an isopropyl group, and particularly preferably a hydrogen atom or a methyl group, from the viewpoints that the raw materials are readily available and that the purification is easier. In addition, the multiple $R^1$s, $R^2$s, and $R^3$s in each of the formulae are particularly preferably the same, from the viewpoints of ease of purification and the like.

Meanwhile, the aryl group which can be selected as $R^4$ in the general formulae (1) and (2) is an aryl group having 6 to 40 carbon atoms. In addition, the number of the carbon atoms is preferably 6 to 30, and more preferably 12 to 20. If the number of the carbon atoms exceeds the upper limit, there is a tendency that, since the glass transition temperature is lowered, a sufficient heat resistance cannot be obtained, and there is a tendency that a sufficient heat shock resistance cannot be obtained in the case where a film is formed. Meanwhile, if the number of the carbon atoms is less than the lower limit, there is a tendency that the solubility of the obtained polyimide in a solvent decreases, so that the formability of the polyimide into a film and the like deteriorates.

In addition, from the viewpoints that a sufficiently high glass transition temperature and a sufficiently low linear expansion coefficient are obtained and that these characteristics can be exhibited in a well-balanced manner, $R^4$ in the general formulae (1) and (2) is preferably one of groups represented by the following general formulae (3) to (6):

[Chem. 7]

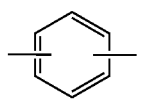

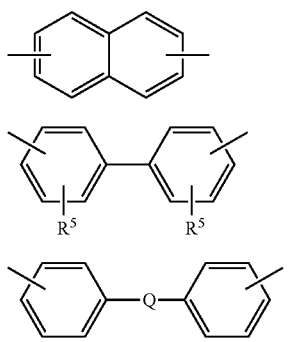

[in the formula (5), $R^5$ represents one selected from the group consisting of a hydrogen atom, a fluorine atom, a methyl group, an ethyl group, and a trifluoromethyl group, and in the formula (6), Q represents one selected from the group consisting of groups represented by the formulae: —O—, —S—, —CO—, —CONH—, —$C_6H_4$—, —COO—, —$SO_2$—, —$C(CF_3)_2$—, —$C(CH_3)_2$—, —$CH_2$—, —O—$C_6H_4$—C$(CH_3)_2$—$C_6H_4$—O—, —O—$C_6H_4$—$SO_2$—$C_6H_4$—O—, —$C(CH_3)_2$—$C_6H_4$—$C(CH_3)_2$—, —O—$C_6H_4$—$C_6H_4$—O—, and —O—$C_6H_4$—O—].

$R^5$ in the general formula (5) is more preferably a hydrogen atom, a fluorine atom, a methyl group, or an ethyl group, and particularly preferably a hydrogen atom, from the viewpoint that the glass transition temperature and the linear expansion coefficient can be achieved in a well-balanced manner at higher levels.

In addition, Q in the general formula (6) is preferably a group represented by the formula: —O—, —S—, —CONH—, —COO—, —CO—, —$C_6H_4$—, —$CH_2$—, or —O—$C_6H_4$—O—, more preferably a group represented by the formula: —O—, —CONH—, —COO—, or —$CH_2$—, and particularly preferably a group represented by the formula: —O— or —CONH—, from the viewpoint that the glass transition temperature and the linear expansion coefficient are achieved in a balanced manner at higher levels.

In addition, the groups which are represented by the general formulae (3) to (6) and which can be selected as $R^4$ are more preferably groups represented by general formulae (5) and (6), from the viewpoints that a sufficiently high glass transition temperature can be achieved, that a more sufficiently low value of the linear expansion coefficient can be achieved, that the balance between these characteristics is improved, and that a higher heat shock resistance can be obtained. In particular, from the viewpoints that a lower linear expansion coefficient can be achieved, and a more advanced heat shock resistance can be obtained in a case where a film is formed, $R^4$ is preferably a group represented by the general formula (5) or a group represented by the general formula (6), where Q is at least one of groups represented by —CONH—, —COO—, —CO—, and —$C_6H_4$— (more preferably a group represented by —CONH— or —COO—, and particularly preferably a group represented by —CONH—). Further, from the viewpoint that when a film is formed by using the obtained polyimide, a higher flexibility can be provided to the film, $R^4$ is preferably the group represented by the general formula (3) or a group represented by the general formula (6), where Q is at least one of groups represented by —O—, —S—, —$CH_2$—, and —O—$C_6H_4$—O— (more preferably a group represented by —O— or —$CH_2$—, and further preferably the group represented by —O—).

In addition, n in the general formulae (1) and (2) represents an integer of 0 to 12. If the value of n exceeds the upper limit, the purification is difficult. In addition, an upper limit value of the numeric value range of n in the general formulae (1) and (2) is more preferably 5, and particularly preferably 3, from the viewpoint that the purification is easier. Meanwhile, a lower limit value of the numeric value range of n in the general formulae (1) and (2) is more preferably 1, and particularly preferably 2, from the viewpoint of the stability of a raw material of a monomer (for example, a tetracarboxylic dianhydride represented by the general formula (7) or (8) described later) used for producing the polyimide. Accordingly, n in the general formulae (1) and (2) is particularly preferably an integer of 2 or 3.

Moreover, the polyimide is preferably a polyimide comprising at least two repeating units selected from repeating units represented by the general formulae (1) and (2) and having different $R^4$s, from the viewpoint that a sufficiently high glass transition temperature, a sufficiently low linear expansion coefficient, and in a case where a film is formed, a sufficient flexibility of the film are exhibited at high levels in a well-balanced manner. In this case, for example, the polyimide comprising repeating units having different $R^4$s may be a polyimide comprising a repeating unit (A) which comprises at least one of repeating units represented by the general formulae (1) and (2), where $R^4$ is a group selected from the group consisting of the groups represented by the general formula (5); and groups represented by the general formula (6), where Q is a group represented by —CONH—, —COO—, —CO—, or —$C_6H_4$— (more preferably a group represented by —CONH— or —COO—, and particularly preferably a group represented by —CONH—), and a repeating unit (B) which comprises at least one of repeating units represented by the general formulae (1) and (2), where $R^4$ is a group selected from the group consisting of the group represented by the general formula (3); and groups represented by the general formula (6), where Q is a group represented by —O—, —S—, —$CH_2$—, or —O—$C_6H_4$—O— (more preferably a group represented by —O— or —$CH_2$—, and further preferably the group represented by —O—). Note that the repeating unit (B) is more preferably one in which $R^4$ is a group represented by the general formula (6), where Q is a group represented by —O—, —$CH_2$—, or —O—$C_6H_4$—O— (more preferably a group represented by —O— or —$CH_2$—, and further preferably a group represented by —O—), from the viewpoint of the availability of the monomer for production.

In the polyimide according to the present invention, the total amount of the repeating units represented by the general formulae (1) and (2) is 90% by mole or more relative to all the repeating units. If the content ratio is less than the lower limit, a sufficiently high level of linear expansion coefficient (lower linear expansion coefficient) cannot be achieved. The content ratio (the total amount) of the repeating units represented by the general formulae (1) and (2) is more preferably 95 to 100% by mole, further preferably 98 to 100% by mole, and particularly preferably 100% by mole, relative to all the repeating units. Note that, without any particularly limitation, other repeating units derived from known monomers can be selected and used, as appropriate, as repeating units other than the repeating units represented by the general formulae (1) and (2) depending on the application and the like.

In addition, the polyimide according to the present invention only needs to comprise at least one of the repeating units represented by the general formulae (1) and (2). However, when the polyimide comprises the both, the ratio of the repeating unit represented by the general formula (1) and the repeating unit represented by the general formula (2) is preferably 1:2 to 2:1, more preferably 1:1.85 to 1.85:1, and further preferably 1:1.7 to 1.7:1 in terms of the mole ratio ([formula (1)]:[formula (2)]). If the content ratio of the repeating unit represented by the general formula (1) is less than the lower limit, the film tends to be brittle. Meanwhile, also if the content ratio exceeds the upper limit, the film tends to be brittle.

In addition, when the polyimide according to the present invention comprises the above-described repeating units (A) and (B) as the repeating units represented by the general formulae (1) and (2), the total amount of the repeating units (A) and (B) is preferably 90% by mole or more, more preferably 95 to 100% by mole, further preferably 98 to 100% by mole, and particularly preferably 100% by mole relative to all the repeating units, from the viewpoint of more sufficiently obtaining an effect achieved by using a combination of these repeating units. In addition, when the repeating units (A) and (B) are contained, the ratio of the content of the repeating unit (A) to the content of the repeating unit (B) is preferably 9:1 to 6:4 (more preferably 8:2 to 7:3) in terms of the mole ratio ((A):(B)). Note that, when the repeating units (A) and (B) are contained, the structures of the substituents other than $R^4$s in the general formulae (1) and (2) are preferably the same, from the viewpoint that the polyimide can be prepared more efficiently.

In addition, the glass transition temperature of the polyimide according to the present invention is preferably 350° C. to 450° C., more preferably 360° C. to 420° C., and further preferably 370 to 410° C. If the glass transition temperature is lower than the lower limit, the heat resistance tends to be insufficient, the heat shock resistance tends to be insufficient in a case where a film is formed, and it tends to be difficult to sufficiently suppress quality deterioration (occurrence of fractures or the like) of the film, for example, in a heating step during production of a solar cell or a liquid crystal display device. Meanwhile, if the glass transition temperature exceeds the upper limit, a film formed therefrom tends to be rather brittle, because the solid-state polymerization reaction does not proceed sufficiently simultaneously with the thermal ring-closure condensation reaction of the polyamic acid in the production of the polyimide. As the glass transition temperature of the polyimide, a value can be employed which is obtained by using a differential scanning calorimeter (for example, one manufactured by SII NanoTechnology Inc. under the trade name of "DSC7020") as a measuring apparatus and scanning a range between 30° C. to 440° C. under conditions of a rate of temperature rise of 10° C./minutes and a rate of temperature drop of 30° C./minutes under a nitrogen atmosphere. Note that, for a polyimide having no glass transition temperature between the scan temperatures of 30° C. to 440° C., the glass transition temperature is measured by changing the above-described scan temperature to a range from 30° C. to 470° C.

In addition, the linear expansion coefficient of the polyimide according to the present invention is preferably 15 ppm/° C. or less, more preferably 12 ppm/° C. or less, and further preferably 10 ppm/° C. or less. If the linear expansion coefficient exceeds the upper limit, there is a tendency that a sufficient heat shock resistance cannot be obtained in a case where a film is formed, and it tends to be difficult to sufficiently suppress the quality deterioration, because a fracture or the like occurs in the thin film. For example, when a film is formed by using a polyimide having a linear expansion coefficient exceeding the upper limit, and the film is used for producing a solar cell or a liquid crystal display device, the film is exposed to high temperature during the production thereof, so that a fracture or the like tend to occur in the film. In addition, although a lower limit value of the linear expansion coefficient varies depending on the application, the lower limit value is preferably 1 ppm/° C., and more preferably 4 ppm/° C. In addition, in the present invention, a method for measuring the linear expansion coefficient of the polyimide is as follows. Specifically, a polyimide film having a size of 20 mm in length, 5 mm in width, and 0.05 mm (50 μm) in thickness is formed. Then, the film is dried in a vacuum (at 120° C. for 1 hour), and subjected to a heat treatment under a nitrogen atmosphere at 200° C. for 1 hour to obtain a measurement sample. By using thus obtained measurement sample and by using a thermomechanical analyzer (manufactured by Rigaku Corporation under the trade name of "TMA8310") as a measuring apparatus, the change in length of the sample in the longitudinal direction is measured from 50° C. to 200° C. under a nitrogen atmosphere by employing conditions of a tensile mode (49 mN) and a rate of temperature rise of 5° C./minutes. Then, an average value of change in length per 1° C. over the temperature range from 50° C. to 200° C. is determined and the thus obtained value can be employed as the linear expansion coefficient of the polyimide. Note that the glass transition temperature and the linear expansion coefficient of the polyimide can be easily set within the numeric value range by changing, as appropriate, the kinds of $R^1$ to $R^4$ in the general formulae (1) and (2) and the like. Moreover, the linear expansion coefficient can be finely adjusted to be within the numeric value range by stretching the polyimide film (by longitudinal stretch, transversal stretch, oblique stretch, press stretch, or the like), by stretching a film of a polyamic acid, which is a precursor of the polyimide, before a heat treatment, or by performing a heat treatment on a film of a polyamic acid, which is a precursor of the polyimide, with the polyamic acid film being fixed.

In addition, the polyimide is preferably one having a 5% weight loss temperature of 450° C. or above, and more preferably 460 to 550° C. If the 5% weight loss temperature is lower than the lower limit, there is a tendency that a sufficient heat shock resistance cannot be obtained in a case where a film is formed. Meanwhile, if the 5% weight loss temperature exceeds the upper limit, it tends to be difficult to produce a polyimide having such a characteristic. Note that the 5% weight loss temperature can be determined by gradually heating a sample from room temperature (25° C.) under a nitrogen gas atmosphere with a nitrogen gas flow, and measuring a temperature at which the weight loss of the sample used reaches 5%.

Moreover, regarding the molecular weight of the polyimide, the molecular weight can be evaluated by measurement using an intrinsic viscosity [η] of the polyamic acid, which is a precursor of the polyimide, because a film after thermal imidization may be hardly soluble in commonly used organic solvents. The intrinsic viscosity [η] of the polyamic acid is preferably 0.1 to 8.0, more preferably 0.1 to 6.0, further preferably 0.1 to 3.0, and particularly preferably 0.4 to 2.0. If the intrinsic viscosity is lower than the lower limit, it tends to be difficult to achieve a sufficient heat shock resistance. Meanwhile, if the intrinsic viscosity exceeds the upper limit, it tends to be difficult to cast a film. The intrinsic viscosity [η] can be measured as follows. Specifically, first, by using N,N-dimethylacetamide as a solvent, a measurement sample (solution) is obtained in which the polyamic acid is dissolved in the N,N-dimethylacetamide at a concentration of 0.5 g/dL. Next, by using the measurement sample, the viscosity of the measurement sample is measured with a kinematic viscometer under a temperature condition of 30° C., and the thus determined value is employed as the intrinsic viscosity [η]. Note that an automatic viscometer manufactured by RIGO CO., LTD. (trade name: "VMC-252") is used as the kinematic viscometer.

In addition, in the polyimide, the polymer chain preferably forms a higher-order structure comprising a planar zigzag structure. By having such a structure, the polyimide can have a more sufficiently low linear expansion coefficient. The structure of the polymer chain of the polyimide can be found by the molecular orbital calculation of the polyimide on the basis of the kinds of the monomers used. For example, by using a personal computer of FUJITSU, Model FMV-B8200, and MOPAC software of Chem Bio3D Ultra10, the polyimide formed is drawn on Chem Bio3D Ultra10, followed by the MM2 calculation and then the AM1 calculation. Thus, the stable structure of the obtained polymer can be found by simulation. Note that the structure of the polymer chain can also be found by measuring the linear expansion coefficient of the polyimide thin film in the Z direction by employing the optical interferometry, and elucidating the relationship between the linear expansion coefficient and the molecular structure.

Moreover, the form of the polyimide is not particularly limited, and can be in various forms (for example, a film shape or the like) depending on the application. As described above, when a film is formed by using the polyimide, the shape and size of the film can be designed, as appropriate, depending on the application and the like, and are not particularly limited. Here, the thickness of the film is preferably 1 to 200 μm, and more preferably 5 to 100 μm. If the thickness of the film is less than the lower limit, the mechanical strength tends to decrease, and the film tends to be weaker in the use for various applications. Meanwhile, if the thickness of the film exceeds the upper limit, a film formation process tends to be difficult.

In addition, when a film is formed from the polyimide, the film is preferably one having a sufficiently high transparency, and more preferably one having a total luminous transmittance of 80% or higher (further preferably 85% or higher, and particularly preferably 87% or higher). Such a total luminous transmittance can be easily achieved by selecting, as appropriate, the kind of the polyimide and the like. Note that a value measured by using a measuring apparatus manufactured by NIPPON DENSHOKU INDUSTRIES CO., LTD. under the trade name of "Haze Meter NDH-5000" can be employed as the total luminous transmittance.

Moreover, when a film is formed from the polyimide, the film has a refractive index of preferably 1.50 to 1.70, and more preferably 1.55 to 1.65. Suppose a case where a laminate of the film with an electro-conductive thin film is formed and used for a transparent application. In such a case or the like, if the refractive index is less than the lower limit, the total luminous transmittance tends to decrease because of the large difference in refractive index between the polyimide and the electro-conductive thin film. Meanwhile, if the refractive index exceeds the upper limit, the polyimide tends to be getting colored, and the synthesis of the polyimide itself tends to be difficult. Note that a value measured by using a refractive index-measuring apparatus (manufactured by Atago Co., Ltd. under the trade name of "NAR-1T SOLID") under a light source of 589 nm and a temperature condition of 23° C. can be employed as the refractive index.

Although the polyimide of the present invention is an aliphatic polyimide obtained by using an aliphatic tetracarboxylic dianhydride, the polyimide is colorless and transparent. Moreover, the polyimide of the present invention has a sufficiently high heat resistance, which is expressed by using the glass transition temperature (Tg) as an index, and can be provided with a sufficiently high Tg, in comparison with polyimides formed from conventionally known aliphatic tetracarboxylic dianhydrides. In addition, the polyimide of the present invention can be provided with a sufficiently high solubility in a solvent. Moreover, since the polyimide of the present invention comprises the repeating units represented by the general formulae (1) and (2) in an amount of 90% by mole or more in total, the polyimide of the present invention has a sufficiently low linear expansion coefficient. For this reason, the polyimide of the present invention is particularly useful as a polyimide for flexible printed wiring boards, a polyimide for heat resistant insulating tapes, a polyimide for enameled wires, a polyimide for protective coatings of semiconductors, a polyimide for liquid crystal orientation films, a polyimide for printable electronics, a polyimide for ITO films, a polyimide for solar cells, a polyimide for organic EL, a polyimide for electronic papers, a polyimide for lithium ion batteries, and the like.

Next, an alicyclic tetracarboxylic dianhydride of the present invention is described. The alicyclic tetracarboxylic dianhydride of the present invention is an alicyclic tetracarboxylic dianhydride used for producing the polyimide of the present invention, and comprises at least one of trans-endo-endo-norbornane-2-spiro-α-cycloalkanone-α'-spiro-2''-norbornane-5,5'',6,6''-tetracarboxylic dianhydrides represented by the following general formula (7):

[Chem. 8]

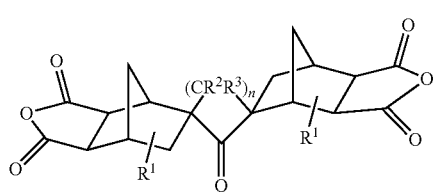

(7)

[in the formula (7), $R^1$, $R^2$, $R^3$, and n have the same meanings as those of $R^1$, $R^2$, $R^3$, and n in the general formulae (1) and (2)] and cis-endo-endo-norbornane-2-spiro-α-cycloalkanone-α'-spiro-2''-norbornane-5,5'',6,6''-tetracarboxylic dianhydrides represented by the following general formula (8):

[Chem. 9]

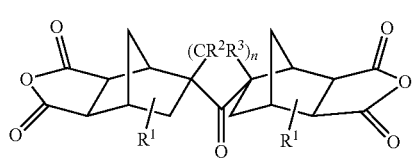

(8)

[in the formula (8), $R^1$, $R^2$, $R^3$, and n have the same meanings as those of $R^1$, $R^2$, $R^3$, and n in the general formulae (1) and (2)], wherein
a total amount of the alicyclic tetracarboxylic dianhydrides represented by the general formulae (7) and (8) is 90% by mole or more.

The trans-endo-endo-norbornane-2-spiro-α-cycloalkanone-α'-spiro-2''-norbornane-5,5'',6,6''-tetracarboxylic dianhydride represented by the general formula (7) (hereinafter, simply referred to as "alicyclic tetracarboxylic dianhydride represented by the general formula (7)" in some cases)

is a compound which can be used as a material (monomer) for forming the polyimide of the present invention, and can be used for forming a repeating unit represented by the general formula (1) (a trans-endo-endo type repeating unit) in the polyimide. Accordingly, $R^1$, $R^2$, $R^3$, and n in the alicyclic tetracarboxylic dianhydride represented by the general formula (7) have the same meanings as those of $R^1$, $R^2$, $R^3$, and n in the general formula (1) (preferred ones thereof are also the same). Note that the alicyclic tetracarboxylic dianhydride represented by the general formula (7) is an isomer of the norbornane-2-spiro-α-cycloalkanone-α'-spiro-2"-norbornane-5,5",6,6"-tetracarboxylic dianhydride in which the conformation of the two norbornane groups is trans, and the configuration of the carbonyl group of the cycloalkanone is endo with respect to each of the two norbornane groups.

Meanwhile, the cis-endo-endo-norbornane-2-spiro-α-cycloalkanone-α'-spiro-2"-norbornane-5,5",6,6"-tetracarboxylic dianhydride represented by the general formula (8) (hereinafter, simply referred to as "alicyclic tetracarboxylic dianhydride represented by the general formula (8)" in some cases) is a compound which can be used as a material (monomer) for forming the polyimide of the present invention and can be used for forming a repeating unit represented by the general formula (2) (a cis-endo-endo type repeating unit) in the polyimide. Accordingly, $R^1$, $R^2$, $R^3$, and n in the alicyclic tetracarboxylic dianhydride represented by the general formula (8) have the same meanings as those of $R^1$, $R^2$, $R^3$, and n in the general formula (2) (preferred ones thereof are also the same). Note that the alicyclic tetracarboxylic dianhydride represented by the general formula (8) is an isomer of the norbornane-2-spiro-α-cycloalkanone-α'-spiro-2"-norbornane-5,5",6,6"-tetracarboxylic dianhydride in which the conformation of the two norbornane groups is cis, and the configuration of the carbonyl group of the cycloalkanone is endo with respect to each of the two norbornane groups.

In addition, in the alicyclic tetracarboxylic dianhydride of the present invention, the total amount (content) of the alicyclic tetracarboxylic dianhydrides represented by the general formulae (7) and (8) is 90% by mole or more relative to all alicyclic tetracarboxylic dianhydrides. Accordingly, the alicyclic tetracarboxylic dianhydride of the present invention is an alicyclic tetracarboxylic dianhydride, in which the purity of the alicyclic tetracarboxylic dianhydrides represented by the general formulae (7) and (8) is 90% by mole or more. When a polyimide is produced by using an alicyclic tetracarboxylic dianhydride in which the total amount (content ratio) of the alicyclic tetracarboxylic dianhydrides represented by the general formulae (7) and (8) is less than the lower limit, the planar zigzag structure of the main chain cannot be formed sufficiently in the produced polyimide, and a sufficiently low linear expansion coefficient cannot be obtained. In addition, from the same viewpoints, the total amount (content ratio) of the alicyclic tetracarboxylic dianhydrides represented by the general formulae (7) and (8) is preferably 95% by mole or more, preferably 98 to 100% by mole, and particularly preferably 100% by mole, relative to all alicyclic tetracarboxylic dianhydrides.

In addition, the alicyclic tetracarboxylic dianhydride of the present invention only need to comprise at least one of the alicyclic tetracarboxylic dianhydrides represented by the general formulae (7) and (8). However, when the both are contained, the ratio between the alicyclic tetracarboxylic dianhydrides represented by the general formula (7) and the general formula (8) is preferably 1:2 to 2:1, more preferably 1:1.85 to 1.85:1, and further preferably 1:1.7 to 1.7:1, in terms of mole ratio ([formula (7)]:[formula (8)]). If the mole ratio is less than the lower limit, the obtained polyimide film tends to be brittle. Meanwhile, if the mole ratio exceeds the upper limit, the obtained polyimide film also tends to be brittle.

Note that the total amount (content) and the mole ratio ([formula (7)]:[formula (8)]) of the alicyclic tetracarboxylic dianhydrides represented by the general formula (7) and the general formula (8) in the alicyclic tetracarboxylic dianhydride of the present invention can be determined by, for example, on the basis of a graph of a spectrum obtained by HPLC measurement, by finding the peak area ratio of each isomer, followed by calculation using a standard curve. Note that the HPLC measurement can be conducted as follows. Specifically, a measuring apparatus manufactured by Agilent Technologies, Inc. under the trade name of "1200 Series" is used, and a column manufactured by Agilent Technologies, Inc. under the trade name of "Eclipse XDB-C18 (5 μm, diameter: 4.6 mm, length: 150 mm)" is used. A mixture of acetonitrile and distilled water (acetonitrile/distilled water=70 ml/30 ml) is used as the solvent. The solvent flow rate is set to 1 ml/min., the detection wavelength of a diode array detector (DAD) is set to 210 nm, and the temperature thereof is set to 35° C. In addition, a sample is prepared by adding 1 mg of an alicyclic tetracarboxylic dianhydride per 1.5 ml of the solvent. Thus, the HPLC measurement can be conducted. Meanwhile, the standard curve can be obtained by obtaining an HPLC spectrum by using dicyclopentadiene, naphthalene, or the like as a standard sample under the same measurement conditions. In addition, the area ratio of the peak attributable to each isomer in a graph of the HPLC spectrum can be determined directly with the above-described measuring apparatus.

In addition, in the alicyclic tetracarboxylic dianhydride of the present invention, the total amount (content) of the alicyclic tetracarboxylic dianhydrides represented by the general formulae (7) and (8) only needs to be 90% by mole or more, and other alicyclic tetracarboxylic dianhydrides may be contained. Examples of the alicyclic tetracarboxylic dianhydrides other than the alicyclic tetracarboxylic dianhydrides represented by the general formulae (7) and (8) include the other isomers of norbornane-2-spiro-α-cycloalkanone-α'-spiro-2"-norbornane-5,5",6,6"-tetracarboxylic dianhydrides (isomers other than the isomers represented by the general formulae (7) and (8)); alicyclic tetracarboxylic dianhydrides such as 1,2,3,4-cyclobutanetetracarboxylic dianhydride, 1,2,3,4-cyclopentanetetracarboxylic dianhydride, 1,2,4,5-cyclohexanetetracarboxylic dianhydride, 2,3,5-tricarboxycyclopentylacetic dianhydride, 3,5,6-tricarboxynorbornane-2-acetic dianhydride, 2,3,4,5-tetrahydrofurantetracarboxylic dianhydride, 1,3,3a,4,5,9b-hexahydro-5-(tetrahydro-2,5-dioxo-3-furanyl)-naphtho[1,2-c]-furan-1,3-dione, 1,3,3a,4,5, 9b-hexahydro-5-methyl-5-(tetrahydro-2,5-dioxo-3-furanyl)-naphtho[1,2-c]-furan-1,3-dione, 1,3,3a,4,5,9b-hexahydro-8-methyl-5-(tetrahydro-2,5-dioxo-3-furanyl)-naphtho[1,2-c]-furan-1,3-dione, 5-(2,5-dioxotetrahydrofural)-3-methyl-3-cyclohexene-1,2-dicarboxylic dianhydride, and bicyclo[2,2,2]-oct-7-ene-2,3,5,6-tetracarboxylic dianhydride; bicyclo[2,2,1]-heptane-2,3,5,6-tetracarboxylic dianhydride; decahydrodimethanonaphthalene-2,3,6,7-tetracarboxylic dianhydride; and the like.

The polyimide and the alicyclic tetracarboxylic dianhydride of the present invention are described above. Next, methods which can be preferably employed as methods for producing the polyimide and the alicyclic tetracarboxylic dianhydride of the present invention are described.

First, the method for producing an alicyclic tetracarboxylic dianhydride of the present invention is described. The method for producing an alicyclic tetracarboxylic dianhydride of the present invention is not particularly limited, and it is possible to employ, as appropriate, any of
a method (first method) in which the alicyclic tetracarboxylic dianhydride of the present invention is obtained by
preparing a 5-norbornene-2-spiro-α-cycloalkanone-α'-spiro-2''-5''-norbornene represented by the following general formula (9) (hereinafter, simply referred to as "compound represented by the general formula (9)" in some cases):

[Chem. 10]

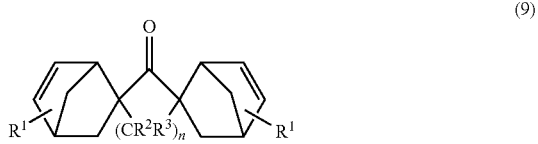

[in the formula (9), $R^1$, $R^2$, $R^3$, and n have the same meanings as those of $R^1$, $R^2$, $R^3$, and n in the general formulae (7) and (8)]; subsequently
converting the compound represented by the general formula (9) to a tetracarboxylic dianhydride to obtain a tetracarboxylic dianhydride represented by the following general formula (10):

[Chem. 11]

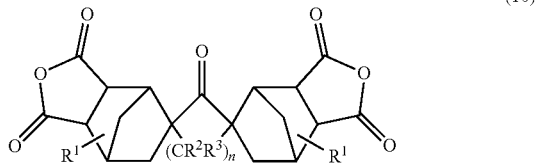

[in the formula (10), $R^1$, $R^2$, $R^3$, and n have the same meanings as those of $R^1$, $R^2$, $R^3$, and n in the general formulae (7) and (8)]; and then
separating and taking out (selecting) the alicyclic tetracarboxylic dianhydrides represented by the general formulae (7) and (8) from the tetracarboxylic dianhydride represented by the general formula (10), so that the purity of the alicyclic tetracarboxylic dianhydrides represented by the general formulae (7) and (8) can be 90% by mole or higher;
a method (second method) in which the above-described alicyclic tetracarboxylic dianhydride of the present invention is obtained by
preparing the compound represented by the general formula (9);
separating and taking out the cis-endo-endo isomer and/or the trans-endo-endo isomer from the compound represented by the general formula (9), so that the purity of the cis-endo-endo isomer and/or the trans-endo-endo isomer can be 90% by mole or higher; and
converting the cis-endo-endo isomer and/or the trans-endo-endo isomer to a tetracarboxylic dianhydride, to obtain an alicyclic tetracarboxylic dianhydride comprising the alicyclic tetracarboxylic dianhydrides represented by the general formulae (7) and (8) in an amount of 90% by mole or more in total, and
a method (third method) in which the above-described alicyclic tetracarboxylic dianhydride of the present invention is obtained by
preparing the compound represented by the general formula (9);
subjecting the compound represented by the general formula (9) to esterification (subsequently, a carboxylic acid may be formed by conducting a hydrolysis treatment or a transesterification reaction with a carboxylic acid); then
separating and taking out the cis-endo-endo isomer and/or the trans-endo-endo isomer from the obtained compound (ester or carboxylic acid), so that the purity of the cis-endo-endo isomer and/or the trans-endo-endo isomer can be 90% by mole or higher;
converting the cis-endo-endo isomer and/or the trans-endo-endo isomer to an acid dianhydride, to obtain an alicyclic tetracarboxylic dianhydride comprising the alicyclic tetracarboxylic dianhydrides represented by the general formulae (7) and (8) in an amount of 90% by mole or more in total, for example.

As described above, as the method for obtaining the alicyclic tetracarboxylic dianhydride of the present invention, it is possible to employ, for example, the method (first method) in which the above-described alicyclic tetracarboxylic dianhydride of the present invention is obtained by separating and taking out the cis-endo-endo isomer and/or the trans-endo-endo isomer at the stage where the tetracarboxylic dianhydride represented by the general formula (10) is obtained by using the compound represented by the general formula (9), so that the purity of the cis-endo-endo isomer and/or the trans-endo-endo isomer can be 90% by mole or higher, the method (second method) in which the above-described alicyclic tetracarboxylic dianhydride of the present invention is obtained by separating and taking out the cis-endo-endo isomer and/or the trans-endo-endo isomer of the compound represented by the general formula (9) at the stage where the compound represented by the general formula (9), which is a material used, is prepared, so that the purity of the cis-endo-endo isomer and/or the trans-endo-endo isomer can be 90% by mole or higher, and converting the cis-endo-endo isomer and/or the trans-endo-endo isomer to a tetracarboxylic dianhydride, or the method (third method) in which the above-described alicyclic tetracarboxylic dianhydride of the present invention is obtained by separating and taking out the cis-endo-endo isomer and/or the trans-endo-endo isomer of the compound (ester or carboxylic acid) obtained at the stage where the compound represented by the general formula (9) is esterified, so that the purity of the cis-endo-endo isomer and/or the trans-endo-endo isomer can be 90% by mole or higher, and converting the cis-endo-endo isomer and/or the trans-endo-endo isomer to an acid dianhydride. Here, a compound represented by the general formula (9) (raw material compound) obtained by employing an ordinary production method is a mixture of six isomers (cis-endo-endo isomer, cis-exo-endo isomer, cis-exo-exo isomer, trans-endo-endo isomer, trans-exo-endo isomer, and trans-exo-exo isomer). Hence, if no separation step or the like is conducted at all, each of the compound (ester or carboxylic acid) which is obtained by esterification of the compound represented by the general formula (9) and which is an intermediate and the finally obtained tetracarboxylic dianhydride represented by the general formula (10) is a mixture containing six isomers (cis-endo-endo isomer, cis-exo-endo isomer, cis-exo-exo isomer, trans-endo-endo isomer, trans-exo-endo isomer, and trans-exo-exo isomer). For this reason, when the alicyclic tetracarboxylic dianhydride of the present invention is produced by employing the above-described method, it is necessary to separate the cis-endo-endo isomer and/or the trans-endo-endo isomer, so that the purity of the cis-endo-endo isomer and/or the trans-endo-endo isomer can be 90% by mole or higher at any one of the raw material compound stage (the stage of the compound represented by the general formula (9)) before the start of the reaction, the reaction intermediate stage (the stage where the compound represented by the general formula (9) is esterified), and the stage of the compound (the tetracarboxylic dianhydride represented by the general formula (10)) obtained after the reaction. In addition, also when the cis-endo-endo isomer and/or the trans-endo-endo isomer of the compound are separated at the above-described raw material compound stage or the above-described reaction intermediate stage, so that the purity of the cis-endo-endo isomer and/or the trans-endo-endo isomer can be 90% by mole or higher, the total amount of the cis-endo-endo isomer and/or the trans-endo-endo isomer in the finally obtained compound is originated from the compound obtained after the separation, and is hence 90% by mole or more. For this reason, the above-described alicyclic tetracarboxylic dianhydride of the present invention can be obtained by employing any of the above-described first to third methods. Note that a method for the esterification, a method for the conversion to an acid dianhydride, and a method for separating the isomers are not particularly limited, and known methods can be employed, as appropriate. First, the method for producing the alicyclic tetracarboxylic dianhydride of the present invention is described below, while the first method is taken as an example.

The first method for producing the alicyclic tetracarboxylic dianhydride of the present invention is a method in which the above-described alicyclic tetracarboxylic dianhydride of the present invention is obtained by preparing the compound represented by the general formula (9), subsequently converting the compound represented by the general formula (9) to a tetracarboxylic dianhydride to obtain the tetracarboxylic dianhydride represented by the general formula (10), and then separating and taking out the alicyclic tetracarboxylic dianhydrides represented by the general formulae (7) and (8) from the tetracarboxylic dianhydride represented by the general formula (10), so that the purity of the alicyclic tetracarboxylic dianhydrides represented by the general formulae (7) and (8) can be 90% by mole or higher.

The compound represented by the general formula (9) may be prepared by employing, for example, a method in which the compound represented by the general formula (9) is produced by utilizing a reaction represented by the following reaction formula (1):

[Chem.12]

[Reaction Formula (I)]

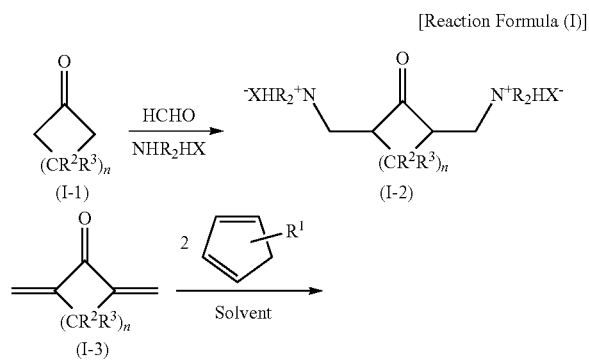

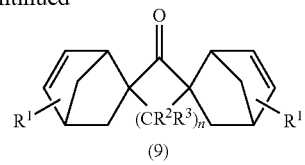

[in the reaction formula (1), $R^1$, $R^2$, $R^3$, and n have the same meanings as those of $R^1$, $R^2$, $R^3$, and n in the general formulae (7) and (8) (preferred ones thereof are also the same), Rs each independently represent a monovalent organic group (for example, a linear saturated hydrocarbon group having 1 to 20 carbon atoms or the like) capable of forming an amine, $X^-$ represents a monovalent ion (for example, a halogen ion, a hydrogen sulfate ion, an acetate ion, or the like) capable of forming an ammonium salt with an amine].

The method represented by the reaction formula (I) proceeds as follows. Specifically, an acidic reaction liquid is obtained by using a cycloalkanone (cyclopentanone, cyclohexanone, or the like) represented by the general formula (I-1), an ammonium salt (for example, a hydrochloric acid salt, a sulfuric acid salt, an acetic acid salt, or the like: a compound represented by the formula: $NHR_2HX$ in the reaction formula (1)) of a secondary amine in an amount of 2 equivalents or more to the cycloalkanone, a formaldehyde derivative, and an acid (hydrochloric acid, sulfuric acid, acetic acid, or the like). Then, the reaction liquid is heated under an inert gas atmosphere at 30 to 180° C. for 0.5 to 10 hours, to thereby allow a Mannich reaction to proceed among the cyclic ketone having active α-hydrogens at both neighboring positions of the carbonyl group, the formaldehyde, and the secondary amine in the reaction liquid. Thus, the Mannich base represented by the general formula (I-2) is synthesized. Subsequently, a mixture is obtained by adding, to the reaction liquid without isolating the obtained Mannich base, an organic solvent (the organic solvent may be any, as long as the organic solvent can be used for a Diels-Alder reaction, and is preferably an organic solvent such as tetrahydrofuran, methanol, ethanol, isopropanol, butanol, acetonitrile, methyl cellosolve, ethyl cellosolve, ethylene glycol, propylene glycol monomethyl ether, or propylene glycol), and a cyclopentadiene which may have, as a substituent, a group which is the same as that selectable as $R^1$ in the general formula (10) (in an amount of 2 equivalents or more relative to the Mannich base). Then, the mixture is adjusted to be neutral or basic by introducing a base thereto, and the mixture is stirred for 0.1 to 48 hours under a condition of 0 to 150° C. (preferably about 60° C.). Thus, a divinyl ketone represented by the general formula (I-3) is synthesized in the mixture from the Mannich base represented by the general formula (I-2), and then the divinyl ketone represented by the general formula (I-3) and the above-described optionally substituted cyclopentadiene are reacted with each other (Diels-Alder reaction). In this manner, the compound represented by the general formula (9) is produced in this method. Note that, as the formaldehyde derivative, any known formaldehyde derivative which is used for producing a Mannich base can be used, as appropriate, and for example, formalin, paraformaldehyde, trioxane, 1,3-dioxolane, or the like can be used, as appropriate. In addition, the divinyl ketone is synthesized when an amine compound is eliminated from the Mannich base during the stirring of the mixture under a condition of 0 to 150° C.

In addition, examples of the cycloalkanone represented by the general formula (I-1) in the reaction formula (I) include cyclopropanone, cyclobutanone, cyclopentanone, cyclohexanone, cycloheptanone, cyclooctanone, cyclononanone, cyclodecanone, cycloundecanone, cyclododecanone, cyclotridecanone, cyclotetradecanone, cyclopentadecanone, 3-methylcyclobutanone, 3-methylcyclopentanone, 3-methylcyclohexanone, 3-methylcycloheptanone, 3-methylcyclooctanone, 3-methylcyclononanone, 3-methylcyclodecanone, 3-methylcycloundecanone, 3-methylcyclododecanone, 3-methylcyclotridecanone, 3-methylcyclotetradecanone, 3-methylcyclopentadecanone, and the like.

Meanwhile, examples of the ammonium salt of the secondary amine include salts (secondary amine salts in which the above-described X⁻ serves as a counter anion) of secondary amines such as dimethylamine, diethylamine, di-n-propylamine, diisopropylamine, di-n-butylamine, diisobutylamine, di-sec-butylamine, di-t-butylamine, dipentylamine, dicyclopentylamine, dihexylamine, dicyclohexylamine, diheptylamine, dioctylamine, di(2-ethylhexyl)amine, dinonylamine, didecylamine, diundecylamine, didodecylamine, ditridecylamine, ditetradecylamine, dipentadecylamine, dihexadecylamine, diheptadecylamine, dioctadecylamine, dinonadecylamine, morpholine, diethanolamine, aziridine, azetidine, pyrrolidine, piperidine, indoline, and isoindoline. In addition, X⁻ in the reaction formula (I) is a so-called counter anion, and examples thereof include F⁻, Cl⁻, Br⁻, I⁻, CH₃COO⁻, CF₃COO⁻, CH₃SO₃⁻, CF₃SO₃⁻, C₆H₅SO₃⁻, CH₃C₆H₄SO₃⁻, HOSO₃⁻, H₂PO₄⁻, and the like. In addition, the divinyl ketone is synthesized when an amine compound is eliminated from the Mannich base during the stirring of the mixture under a condition of 0 to 150° C.

Examples of the thus obtained compound represented by the general formula (9) include 5-norbornene-2-spiro-α-cyclopentanone-α'-spiro-2''-5''-norbornene (also referred to as "5-norbornene-2-spiro-2'-cyclopentanone-5'-spiro-2''-5''-norbornene"), methyl-5-norbornene-2-spiro-α-cyclopentanone-α'-spiro-2''-(methyl-5''-norbornene 5-norbornene-2-spiro-α-cyclohexanone-α'-spiro-2''-5''-norbornene (also referred to as "5-norbornene-2-spiro-2'-cyclohexanone-6'-spiro-2''-5''-norbornene"), methyl-5-norbornene-2-spiro-α-cyclohexanone-α'-spiro-2''-(methyl-5''-norbornene), 5-norbornene-2-spiro-α-cyclopropanone-α'-spiro-2''-5''norbornene, 5-norbornene-2-spiro-α-cyclobutanone-α'-spiro-2''-5''-norbornene, 5-norbornene-2-spiro-α-cycloheptanone-α'-spiro-2''-5''-norbornene, 5-norbornene-2-spiro-α-cyclooctanone-α'-spiro-2''-5''-norbornene, 5-norbornene-2-spiro-α-cyclononanone-α'-spiro-2''-5''-norbornene, 5-norbornene-2-spiro-α-cyclodecanone-α'-spiro-2''-5''-norbornene, 5-norbornene-2-spiro-α-cycloundecanone-α'-spiro-2''-5''-norbornene, 5-norbornene-2-spiro-α-cyclododecanone-α'-spiro-2''-5''-norbornene, 5-norbornene-2-spiro-α-cyclotridecanone-α'-spiro-2''-5''-norbornene, 5-norbornene-2-spiro-α-cyclotetradecanone-α'-spiro-2''-5''-norbornene, 5-norbornene-2-spiro-α-cyclopentadecanone-α'-spiro-2'-5''-norbornene, 5-norbornene-2-spiro-α-(methylcyclopentanone)-α'-spiro-2'-5''-norbornene, 5-norbornene-2-spiro-α-(methylcyclohexanone)-α'-spiro-2''-5''-norbornene, and the like. Note that the thus obtained compound (raw material compound) represented by the general formula (9) is a mixture of six isomers (cis-endo-endo isomer, cis-exo-endo isomer, cis-exo-exo isomer, trans-endo-endo isomer, trans-exo-endo isomer, and trans-exo-exo isomer).

Meanwhile, a preferred method for obtaining the tetracarboxylic dianhydride represented by the general formula (10) by converting the compound represented by the general formula (9) to a tetracarboxylic dianhydride is not particularly limited, and any known method capable of converting a tetracarboxylic acid to a dianhydride can be employed, as appropriate. For example, a method described in Macromolecules (vol. 27), p. 1117 published in 1994 may be employed. Specifically, as the method for conversion to the tetracarboxylic dianhydride, it is possible to employ a method in which the compound represented by the general formula (9) is converted to a tetraester with carbon monoxide and an alcohol such as methanol in the presence of a Pd catalyst, copper(II) chloride, and sodium acetate; the obtained tetramethyl ester is subjected to a transesterification reaction with formic acid in the presence of an acid catalyst such as p-toluenesulfonic acid, to thereby obtain a tetracarboxylic acid; and then by causing acetic anhydride to be coexistent in the reaction system of the transesterification reaction, the tetracarboxylic acid is converted to a tetracarboxylic dianhydride with the acetic anhydride, or a method in which after the tetracarboxylic acid is once isolated, a thermal dehydration reaction is conducted in a sublimation purification apparatus under a vacuum condition.

In addition, as a preferred method for obtaining the tetracarboxylic dianhydride represented by the general formula (10) by converting the compound represented by the general formula (9) to a tetracarboxylic dianhydride, for example, a method may be used which comprises:

a step (first step) of reacting the compound represented by the general formula (9) with an alcohol and carbon monoxide in the presence of a palladium catalyst and an oxidizing agent, to thereby obtain at least one compound of norbornane-2-spiro-α-cycloalkanone-α'-spiro-2''-norbornane-5,5',6,6''-tetracarboxylic acids and esters thereof represented by the following general formula (11) (hereinafter, simply referred to as "compound represented by the general formula (11)" in some cases):

[Chem. 13]

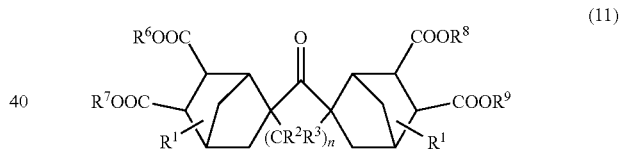

(11)

[in the formula (11), R¹, R², R³, and n have the same meanings as those of R¹, R², R³, and n in the general formulae (7) and (8), R⁶, R⁷, R⁸, and R⁹ each independently represent one selected from the group consisting of a hydrogen atom, alkyl groups having 1 to 10 carbon atoms, cycloalkyl groups having 3 to 10 carbon atoms, alkenyl groups having 2 to 10 carbon atoms, aryl groups having 6 to 20 carbon atoms, and aralkyl groups having 7 to 20 carbon atoms, and n represents an integer of 0 to 12]; and a step (second step) of obtaining, from the compound, the tetracarboxylic dianhydride represented by the general formula (10) (a norbornane-2-spiro-α-cycloalkanone-α'-spiro-2''-norbornane-5,5'',6,6''-tetracarboxylic dianhydride) by using a lower carboxylic acid (such as formic acid, acetic acid, or propionic acid), an acid catalyst, and acetic anhydride (hereinafter, this method being referred to as "method (i) for producing the tetracarboxylic dianhydride represented by the general formula (10)" in some cases). Note that, in the compound represented by the general formula (11), R¹, R², R³, and n in the general formula (11) have the same meanings as those of R¹, R², R³, and n in the general formulae (7) and (8) (preferred ones thereof are also the same).

Meanwhile, the alkyl group which can be selected as each of R⁶, R⁷, R⁸, and R⁹ in the general formula (11) is an alkyl group having 1 to 10 carbon atoms. If the number of carbon atoms of the alkyl group exceeds 10, purification is difficult. In addition, the number of carbon atoms of the alkyl group which can be selected as each of $R^6$, $R^7$, $R^8$, and $R^9$ is more preferably 1 to 5, and further preferably 1 to 3, from the viewpoint that the purification is easier. In addition, the alkyl group which can be selected as each of $R^6$, $R^7$, $R^8$, and $R^9$ may be linear or branched.

Meanwhile, the cycloalkyl group which can be selected as each of $R^6$, $R^7$, $R^8$, and $R^9$ in the general formula (11) is a cycloalkyl group having 3 to 10 carbon atoms. If the number of carbon atoms of the cycloalkyl group exceeds 10, purification is difficult. In addition, the number of carbon atoms of the cycloalkyl group which can be selected as each of $R^6$, $R^7$, $R^8$, and $R^9$ is more preferably 3 to 8, and further preferably 5 to 6, from the viewpoint that the purification is easier.

Moreover, the alkenyl group which can be selected as each of $R^6$, $R^7$, $R^8$, and $R^9$ in the general formula (11) is an alkenyl group having 2 to 10 carbon atoms. If the number of carbon atoms of the alkenyl group exceeds 10, purification is difficult. In addition, the number of carbon atoms of the alkenyl group which can be selected as each of $R^6$, $R^7$, $R^8$, and $R^9$ is more preferably 2 to 5, and further preferably 2 to 3, from the viewpoint that the purification is easier.

Meanwhile, the aryl group which can be selected as each of $R^6$, $R^7$, $R^8$, and $R^9$ in the general formula (11) is an aryl group having 6 to 20 carbon atoms. If the number of carbon atoms of the aryl group exceeds 20, purification is difficult. In addition, the number of carbon atoms of the aryl group which can be selected as each of $R^6$, $R^7$, $R^8$, and $R^9$ is more preferably 6 to 10, and further preferably 6 to 8, from the viewpoint that the purification is easier.

Meanwhile, the aralkyl group which can be selected as each of $R^6$, $R^7$, $R^8$, and $R^9$ in the general formula (11) is an aralkyl group having 7 to 20 carbon atoms. If the number of carbon atoms of the aralkyl group exceeds 20, purification is difficult. In addition, the number of carbon atoms of the aralkyl group which can be selected as each of $R^6$, $R^7$, $R^8$, and $R^9$ is more preferably 7 to 10, and further preferably 7 to 9, from the viewpoint that the purification is easier.

Moreover, from the viewpoint that the purification is easier, $R^6$, $R^7$, $R^8$, and $R^9$ in the general formula (11) are each independently preferably a hydrogen atom, a methyl group, an ethyl group, a n-propyl group, an isopropyl group, a n-butyl group, an isobutyl group, a sec-butyl, a t-butyl, a 2-ethylhexyl group, a cyclohexyl group, an allyl group, a phenyl group, or a benzyl group, and particularly preferably a methyl group. Note that $R^6$, $R^7$, $R^8$, and $R^9$ in the general formula (11) may be the same or different, and are more preferably the same from the viewpoint of synthesis.

Examples of the compound represented by the general formula (11) include norbornane-2-spiro-α-cyclopentanone-α'-spiro-2"-norbornane-5,5",6,6"-tetracarboxylic acid tetramethyl ester, norbornane-2-spiro-α-cyclopentanone-α'-spiro-2"-norbornane-5,5"6,6"-tetracarboxylic acid tetraethyl ester, norbornane-2-spiro-α-cyclopentanone-α'-spiro-2"-norbornane-5,5",6,6"-tetracarboxylic acid tetrapropyl ester, norbornane-2-spiro-α-cyclopentanone-α'-spiro-2"-norbornane-5,5",6,6"-tetracarboxylic acid tetrabutyl ester, norbornane-2-spiro-α-cyclopentanone-α'-spiro-2"-norbornane-5,5",6,6"-tetracarboxylic acid tetra(2-ethylhexyl)ester, norbornane-2-spiro-α-cyclopentanone-α'-spiro-2"-norbornane-5,5",6,6"-tetracarboxylic acid tetraallyl ester, norbornane-2-spiro-α-cyclopentanone-α'-spiro-2"-norbornane-5,5",6,6"-tetracarboxylic acid tetracyclohexyl ester, norbornane-2-spiro-α-cyclopentanone-α'-spiro-2"-norbornane-5,5",6,6"-tetracarboxylic acid tetraphenyl ester, norbornane-2-spiro-α-cyclopentanone-α'-spiro-2"-norbornane-5,5",6,6"-tetracarboxylic acid tetrabenzyl ester, norbornane-2-spiro-α-cyclopentanone-α'-spiro-2"-norbornane-5,5",6,6"-tetracarboxylic acid, methylnorbornane-2-spiro-α-cyclopentanone-α'-spiro-2"-(methylnorbornane)-5,5",6,6"-tetracarboxylic acid tetramethyl ester, norbornane-2-spiro-α-cyclohexanone-α'-spiro-2"-norbornane-5,5",6,6"-tetracarboxylic acid tetramethyl ester, norbornane-2-spiro-α-cyclohexanone-α'-spiro-2"-norbornane-5,5",6,6"-tetracarboxylic acid tetraethyl ester, norbornane-2-spiro-α-cyclohexanone-α'-spiro-2"-norbornane-5,5",6,6"-tetracarboxylic acid tetrapropyl ester, norbornane-2-spiro-α-cyclohexanone-α'-spiro-2"-norbornane-5,5",6,6"-tetracarboxylic acid tetrabutyl ester, norbornane-2-spiro-α-cyclohexanone-α'-spiro-2"-norbornane-5,5",6,6"-tetracarboxylic acid tetra(2-ethylhexyl)ester, norbornane-2-spiro-α-cyclohexanone-α'-spiro-2"-norbornane-5,5",6,6"-tetracarboxylic acid tetraallyl ester, norbornane-2-spiro-α-cyclohexanone-α'-spiro-2"-norbornane-5,5",6,6"-tetracarboxylic acid tetracyclohexyl ester, norbornane-2-spiro-α-cyclohexanone-α'-spiro-2"-norbornane-5,5",6,6"-tetracarboxylic acid tetraphenyl ester, norbornane-2-spiro-α-cyclohexanone-α'-spiro-2"-norbornane-5,5",6,6"-tetracarboxylic acid tetrabenzyl ester, norbornane-2-spiro-α-cyclohexanone-α'-spiro-2"-norbornane-5,5",6,6"-tetracarboxylic acid, methylnorbornane-2-spiro-α-cyclohexanone-α'-spiro-2"-(methylnorbornane)-5,5",6,6"-tetracarboxylic acid tetramethyl ester, norbornane-2-spiro-α-cyclopropanone-α'-spiro-2"-norbornane-5,5",6,6"-tetracarboxylic acid tetramethyl ester, norbornane-2-spiro-α-cyclobutanone-α'-spiro-2"-norbornane-5,5",6,6"-tetracarboxylic acid tetramethyl ester, norbornane-2-spiro-α-cycloheptanone-α'-spiro-2"-norbornane-5,5",6,6"-tetracarboxylic acid tetramethyl ester, norbornane-2-spiro-α-cyclooctanone-α'-spiro-2"-norbornane-5,5",6,6"-tetracarboxylic acid tetramethyl ester, norbornane-2-spiro-α-cyclononanone-α'-spiro-2"-norbornane-5,5",6,6"-tetracarboxylic acid tetramethyl ester, norbornane-2-spiro-α-cyclodecanone-α'-spiro-2"-norbornane-5,5",6,6"-tetracarboxylic acid tetramethyl ester, norbornane-2-spiro-α-cycloundecanone-α'-spiro-2"-norbornane-5,5",6,6"-tetracarboxylic acid tetramethyl ester, norbornane-2-spiro-α-cyclododecanone-α'-spiro-2"-norbornane-5,5",6,6"-tetracarboxylic acid tetramethyl ester, norbornane-2-spiro-α-cyclotridecanone-α'-spiro-2"-norbornane-5,5",6,6"-tetracarboxylic acid tetramethyl ester, norbornane-2-spiro-α-cyclotetradecanone-α'-spiro-2"-norbornane-5,5",6,6"-tetracarboxylic acid tetramethyl ester, norbornane-2-spiro-α-cyclopentadecanone-α'-spiro-2"-norbornane-5,5",6,6"-tetracarboxylic acid tetramethyl ester, norbornane-2-spiro-α-cyclopentanone-α'-spiro-2"-norbornane-5,5",6,6"-tetracarboxylic acid, norbornane-2-spiro-α-cyclohexanone-α'-spiro-2"-norbornane-5,5",6,6"-tetracarboxylic acid, and the like.

In addition, the alcohol used in the first step is preferably an alcohol represented by the following general formula (12):

$$R^{10}OH \qquad (12)$$

[in the formula (12), $R^{10}$ is an atom or group which can be selected as $R^6$, $R^7$, $R^8$, or $R^9$ in the general formula (11) but which is not a hydrogen atom]. Specifically, as the alcohol, it is preferable to use an alkyl alcohol having 1 to 10 carbon atoms, a cycloalkyl alcohol having 3 to 10 carbon atoms, an alkenyl alcohol having 2 to 10 carbon atoms, an aryl alcohol having 6 to 20 carbon atoms, or an aralkyl alcohol having 7 to 20 carbon atoms. Specific examples of the alcohol include methanol, ethanol, butanol, allyl alcohol, cyclohexanol, benzyl alcohol, and the like. Of these alcohols, methanol and ethanol are more preferable, and methanol is particularly preferable, from the viewpoint that the obtained compound is easier to purify. In addition, one of these alcohols may be used alone, or two or more thereof may be used as a mixture.

The reaction in the first step using the alcohol is a reaction (esterification reaction) in which the compound represented by the general formula (9) is reacted with the alcohol ($R^{10}OH$) and carbon monoxide (CO) in the presence of a palladium catalyst and an oxidizing agent, and thereby ester groups each represented by the following general formula (13):

$$—COOR^{10} \qquad (13)$$

[in the formula (13), $R^{10}$ is an atom or a group which can be selected as $R^6$, $R^7$, $R^8$, or $R^9$ in the general formula (11), but which is not a hydrogen atom]
(in each position in which the ester group is introduced, each of $R^{10}$s may be the same or different) are introduced at olefinic positions in the compound represented by the general formula (9), so that the norbornane-2-spiro-α-cycloalkanone-α'-spiro-2"-norbornane-5,5",6,6"-tetracarboxylic acid ester represented by the general formula (11) is obtained.

The amount of the alcohol used in the esterification reaction is not particularly limited, as long as the compound represented by the general formula (11) can be obtained. For example, it is possible to add the alcohol in an amount more than the amount (theoretical amount) theoretically necessary to obtain the compound represented by the general formula (11), and use the excessive alcohol as a solvent, as it is.

In addition, in the esterification reaction, it is only necessary to supply a necessary amount of carbon monoxide to the reaction system. Accordingly, it is unnecessary to use high-purity carbon monoxide gas as the gas for supplying the carbon monoxide, but it is possible to use a mixture gas obtained by mixing carbon monoxide with a gas (for example, nitrogen) inactive in the esterification reaction. It is also possible to use synthetic gas, coal gas, or the like. In addition, the pressure of the carbon monoxide is not particularly limited, and is preferably not lower than normal pressure (approximately 0.1 MPa [1 atm]) but not higher than 10 MPa.

In addition, the palladium catalyst used in the first step is not particularly limited, and a known catalyst containing palladium can be used, as appropriate. Examples thereof include palladium inorganic acid salts, palladium organic acid salts, catalysts in which palladium is supported on a support, and the like. Specific examples of the palladium catalyst include palladium chloride, palladium nitrate, palladium sulfate, palladium acetate, palladium acetate trimer, palladium propionate, palladium carbon, palladium alumina, palladium black, Pd complexes having various ligands, and the like. The amount of the palladium catalyst used is preferably set such that the amount of moles of palladium in the palladium catalyst can be 0.001 to 0.1 times the amount of moles of the compound represented by the general formula (9).

Moreover, the oxidizing agent used in the first step is not particularly limited, as long as the oxidizing agent can oxidize $Pd^0$ to $Pd^{2+}$, when $Pd^{2+}$ in the palladium catalyst is reduced to $Pd^0$ in the esterification reaction. Examples of the oxidizing agent include copper compounds, iron compounds, oxygen, air, hydrogen peroxide, and the like. Specific examples of the oxidizing agent include copper(II) chloride, copper(II) nitrate, copper(II) sulfate, copper(II) acetate, iron(III) chloride, iron(III) nitrate, iron(III) sulfate, iron(III) acetate, manganese dioxide, manganese acetate, and the like. The amount of moles of the oxidizing agent used is preferably 2 to 16 times (more preferably about 8 times) the amount of moles of the 5-norbornene-2-spiro-α-cycloalkanone-α'-spiro-2'-5'-norbornene represented by the general formula (9).

In addition, it is preferable to use a solvent in the reaction (esterification reaction) of the compound represented by the general formula (9) with the alcohol and carbon monoxide. The solvent is not particularly limited, and examples thereof include hydrocarbon-based solvents such as n-hexane, cyclohexane, heptane, pentane, and toluene.

Moreover, since an acid is by-produced from the oxidizing agent or the like in the esterification reaction, a base may be added to remove the acid. The base is preferably a fatty acid salt such as sodium acetate, sodium propionate, or sodium butyrate. In addition, the amount of the base used may be adjusted, as appropriate, depending on the amount of the acid generated and the like.

In addition, a reaction temperature condition in the esterification reaction is not particularly limited, and is preferably 0° C. to 100° C. {more preferably about normal temperature (25° C.)}. If the reaction temperature exceeds the upper limit, the yield tends to decrease. If the reaction temperature is lower than the lower limit, the reaction rate tends to decrease. In addition, a reaction time of the esterification reaction is not particularly limited, and is preferably about 30 minutes to 24 hours.

In addition, in order to convert $R^6$, $R^7$, $R^8$, or $R^9$ in the general formula (11) to a hydrogen atom, a hydrolysis treatment or a transesterification reaction with a carboxylic acid may be conducted, after the introduction of the group represented by the above-described formula: $—COOR^{10}$ by the esterification reaction. A method for the reaction is not particularly limited, and a known method capable of converting the groups represented by the formula: $—COOR^{10}$ to those represented by the formula: —COOH can be employed, as appropriate.

In addition, after the esterification reaction, the hydrolysis, or the like is conducted as described above, a purification step such as recrystallization may be conducted, as appropriate, in order to obtain a compound with a higher purity. A method for the purification is not particularly limited, and a known method can be employed, as appropriate. Thus, the compound (norbornane-2-spiro-α-cycloalkanone-α'-spiro-2"-norbornane-5,5",6,6"-tetracarboxylic acid ester) represented by the general formula (11) can be obtained efficiently by the first step as described above. Note that the compound represented by the general formula (11) obtained by the first step in this manner contains six isomers (cis-endo-endo isomer, cis-exo-endo isomer, cis-exo-exo isomer, trans-endo-endo isomer, trans-exo-endo isomer, and trans-exo-exo isomer).

Subsequently, the second step of the method (i) for producing the tetracarboxylic dianhydride represented by the general formula (10) is described. The second step is a step of obtaining the tetracarboxylic dianhydride represented by the general formula (10) (norbornane-2-spiro-α-cycloalkanone-α'-spiro-2"-norbornane-5,5",6,6"-tetracarboxylic dianhydride) from the compound represented by the general formula (11) by using a lower carboxylic acid (formic acid, acetic acid, propionic acid, or the like), an acid catalyst, and acetic anhydride.

The acid catalyst used in the second step is not particularly limited, and is preferably p-toluenesulfonic acid, benzenesulfonic acid, hydrochloric acid, nitric acid, sulfuric acid, phosphoric acid, methanesulfonic acid, trifluoroacetic acid, Amberlyst, or Amberlite, and more preferably p-toluenesulfonic acid, from the viewpoint of acid strength. The amount of moles of the acid catalyst used in the second step is preferably 0.01 to 2.0 times (more preferably 0.01 to 0.2 times) the amount of moles of the compound represented by the general formula (11). If the amount of the acid catalyst used is less than the lower limit, the reaction rate tends to decrease. Meanwhile, if the amount of the acid catalyst exceeds the upper limit, the yield tends to decrease.

In addition, the lower carboxylic acid used in the second step is preferably formic acid, acetic acid, or propionic acid, and more preferably acetic acid or propionic acid, from the viewpoint of the removability of the lower carboxylic acid ester formed by the transesterification and water formed by the dehydrative ring-closure. The amount of the lower carboxylic acid (for example, formic acid, acetic acid, or propionic acid) used in the second step is not particularly limited, and is preferably such that the amount of moles of the lower carboxylic acid is 4 to 1000 times (more preferably 4 to 100 times) the amount of moles of the compound represented by the general formula (11). If the amount of the lower carboxylic acid (formic acid, acetic acid, propionic acid, or the like) used is less than the lower limit, the reaction rate tends to decrease. Meanwhile, if the amount of the lower carboxylic acid used exceeds the upper limit, the yield tends to decrease.

Moreover, the amount of acetic anhydride used in the second step is not particularly limited, and is preferably such that the amount of moles of the acetic anhydride is 4 to 1000 times (more preferably 4 to 100 times) the amount of moles of the compound represented by the general formula (11). If the amount of acetic anhydride used is less than the lower limit, the reaction rate tends to decrease. Meanwhile, if the amount of acetic anhydride used exceeds the upper limit, the yield tends to decrease.

In addition, the second step is not particularly limited, but preferably comprises the following steps (2-a) to (2-c), for example. Specifically, the second step preferably comprises: a step (2-a) of preparing a mixture liquid of the compound represented by the general formula (11) with the lower carboxylic acid (formic acid, acetic acid, propionic acid, or the like) and the acid catalyst, and heating the mixture liquid under reflux; a step (2-b) of obtaining a liquid concentrate by concentrating the mixture liquid by distilling off a portion of the liquid in the mixture liquid under reduced pressure, adding again the lower carboxylic acid (formic acid or the like) to the obtained liquid concentrate, heating again the mixture under reflux, and then concentrating again the mixture by distilling off a portion of the liquid in the obtained mixture liquid under reduced pressure; and a step (2-c) of adding the lower carboxylic acid (formic acid, acetic acid, propionic acid, or the like) and acetic anhydride to the liquid concentrate, and heating the mixture under reflux, to thereby obtain the compound represented by the general formula (10). The employment of this method makes it possible to more efficiently obtain the compound represented by the general formula (10) from the compound represented by the general formula (11).

The amount of the lower carboxylic acid (formic acid, acetic acid, propionic acid, or the like) used in the preparation of the mixture liquid in the step (2-a) is preferably such that the amount of moles of the lower carboxylic acid is 4 to 1000 times (particularly preferably about 50 times) the amount of moles of the compound represented by the general formula (11).

In addition, when such a method is employed, the step of performing the addition of the lower carboxylic acid such as formic acid, acetic acid, or propionic acid to the liquid concentrate and the concentrating of the liquid concentrate is preferably conducted repeatedly (preferably conducted 1 to 5 times repeatedly) in the step (2-b). Alternatively, it is also preferable to distill off the produced carboxylic acid ester and water with the lower carboxylic acid, and then continuously add the lower carboxylic acid, in the step (2-b). By repeatedly conducting the step of performing the addition of the lower carboxylic acid such as formic acid, acetic acid, or propionic acid to the liquid concentrate and the concentrating of the liquid concentrate in the step (2-b), a tetraester can be completely converted to a tetracarboxylic acid, when any one of $R^6$, $R^7$, $R^8$, and $R^9$ in the general formula (11) is a group other than a hydrogen atom. Hence, the compound represented by the general formula (10) can be obtained more efficiently in the step (2-c) conducted later. In addition, the amount of the lower carboxylic acid (formic acid, acetic acid, propionic acid, or the like) used in the production of the mixture liquid in the step (2-a) is preferably such that the amount of moles of the lower carboxylic acid is about 50 times the amount of moles of the compound represented by the general formula (11). In addition, the amount of the lower carboxylic acid (formic acid or the like) added to the liquid concentrate in each of the steps (2-b) and (2-c) is preferably approximately equal to the amount of the liquid distilled off during the concentration.

In addition, a method for the concentration (the distilling-off under reduced pressure) of the mixture liquid in the step (2-b) is not particularly limited, and a known method can be employed, as appropriate. Meanwhile, a temperature condition of the heating under reflux in each of the steps (2-a) to (2-c) is preferably 100° C. to 180° C., and more preferably 100° C. to 140° C. If the temperature of the heating under reflux is lower than the lower limit, the yield tends to decrease. Meanwhile, if the temperature of the heating under reflux exceeds the upper limit, by-products tend to increase, and the transparency tends to decrease because of coloring. In addition, a time of the heating under reflux is preferably about 30 minutes to 50 hours (more preferably about 30 minutes to 24 hours).

Moreover, after a crude product of the compound represented by the general formula (10) is obtained from the compound represented by the general formula (11) in the second step, the crude product may be subjected, as appropriate, to a purification step such as recrystallization or sublimation. This purification step makes it possible to obtain the compound represented by the general formula (10) with a higher purity. A method for the purification is not particularly limited, and a known method can be employed, as appropriate. Note that when a solid acid such as Amberlite is used as the acid catalyst, purification by recrystallization can be conducted simultaneously with concentration by removing the acid catalyst only by filtration, and concentrating the obtained filtrate. Thus, the compound (tetracarboxylic dianhydride) represented by the general formula (10) can be obtained in a high yield.

Note that, regarding the thus obtained tetracarboxylic dianhydride represented by the general formula (10), $R^1$, $R^2$, $R^3$, and n in the formula (10) are the same as $R^1$, $R^2$, and $R^3$, and n in the general formulae (7) and (8) (accordingly, in the general formulae (1) and (2)), and preferred $R^1$, $R^2$, $R^3$, and n are the same as the preferred $R^1$, $R^2$, and $R^3$, and n in the general formula (1). In addition, examples of the thus obtained tetracarboxylic dianhydride represented by the general formula (10) include norbornane-2-spiro-α-cyclopentanone-α'-spiro-2''-norbornane-5,5'',6,6''-tetracarboxylic dianhydride (also referred to as "norbornane-2-spiro-2'-cyclopentanone-5'-spiro-2''-norbornane-5,5'',6,6''-tetracarboxylic dianhydride"), methylnorbornane-2-spiro-α-cyclopentanone-α'-spiro-2''-(methylnorbornane)-5,5''',6,6''-tetracarboxylic dianhydride, norbornane-2-spiro-α-cyclohexanone-α'-spiro-2''-norbornane-5,5'',6,6''-tetracarboxylic dianhydride (also referred to as "norbornane- 2-spiro-2'-cyclohexanone-6'-spiro-2"-norbornane-5,5",6,6"-tetracarboxylic dianhydride"), methylnorbornane-2-spiro-α-cyclohexanone-α'-spiro-2"-(methylnorbornane)-5,5",6,6"-tetracarboxylic dianhydride, norbornane-2-spiro-α-cyclopropanone-α'-spiro-2"-norbornane-5,5",6,6"-tetracarboxylic dianhydride, norbornane-2-spiro-α-cyclobutanone-α'-spiro-2"-norbornane-5,5",6,6"-tetracarboxylic dianhydride, norbornane-2-spiro-α-cycloheptanone-α'-spiro-2"-norbornane-5,5",6,6"-tetracarboxylic dianhydride, norbornane-2-spiro-α-cyclooctanone-α'-spiro-2"-norbornane-5,5",6,6"-tetracarboxylic dianhydride, norbornane-2-spiro-α-cyclononanone-α'-spiro-2"-norbornane-5,5",6,6"-tetracarboxylic dianhydride, norbornane-2-spiro-α-cyclodecanone-α'-spiro-2"-norbornane-5,5",6,6"-tetracarboxylic dianhydride, norbornane-2-spiro-α-cycloundecanone-α'-spiro-2"-norbornane-5,5",6,6"-tetracarboxylic dianhydride, norbornane-2-spiro-α-cyclododecanone-α'-spiro-2"-norbornane-5,5",6,6"-tetracarboxylic dianhydride, norbornane-2-spiro-α-cyclotridecanone-α'-spiro-2"-norbornane-5,5",6,6"-tetracarboxylic dianhydride, norbornane-2-spiro-α-cyclotetradecanone-α'-spiro-2"-norbornane-5,5",6,6"-tetracarboxylic dianhydride, norbornane-2-spiro-α-cyclopentadecanone-α'-spiro-2"-norbornane-5,5",6,6"-tetracarboxylic dianhydride, norbornane-2-spiro-α-(methylcyclopentanone)-α'-spiro-2"-norbornane-5,5",6,6"-tetracarboxylic dianhydride, norbornane-2-spiro-α-(methylcyclohexanone)-α'-spiro-2"-norbornane-5,5",6,6"-tetracarboxylic dianhydride, and the like.

Note that "the method (i) for producing the tetracarboxylic dianhydride represented by the general formula (10)" described as a preferred method for obtaining the tetracarboxylic dianhydride represented by the general formula (10) by converting the compound represented by the general formula (9) to a tetracarboxylic dianhydride is a method utilizing a reaction schematically represented by the following reaction formula (II):

[Chem.14]

[Reaction Formula (II)]

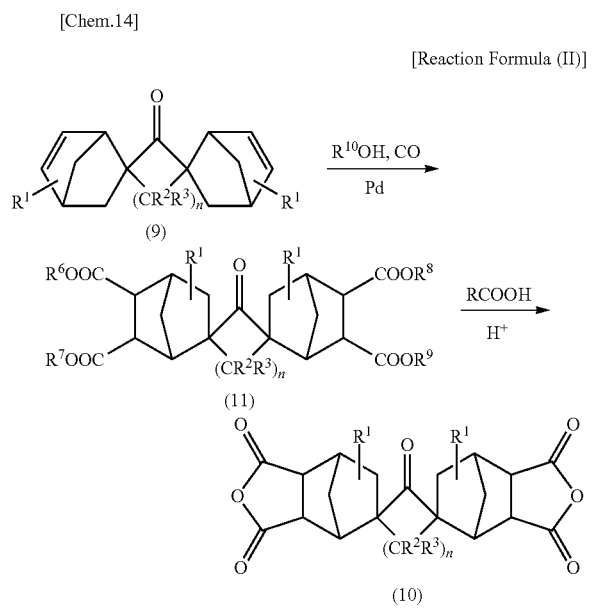

[in the reaction formula (II), $R^1$, $R^2$, $R^3$, and n have the same meanings as those of $R^1$, $R^2$, $R^3$, and n in the general formulae (7) and (8), $R^6$, $R^7$, $R^8$, and $R^9$ each independently represent one selected from the group consisting of a hydrogen atom, alkyl groups having 1 to 10 carbon atoms, cycloalkyl groups having 3 to 10 carbon atoms, alkenyl groups having 2 to 10 carbon atoms, aryl groups having 6 to 20 carbon atoms, and aralkyl groups having 7 to 20 carbon atoms, and $R^{10}$ has the same meaning as that of $R^{10}$ in the general formula (12)]. However, the preferred method for obtaining the tetracarboxylic dianhydride represented by the general formula (10) is not limited thereto.

Another preferred method for obtaining the tetracarboxylic dianhydride represented by the general formula (10) is, for example, a method in which after the compound represented by the general formula (11) is obtained by conducting the first step, the compound represented by the general formula (11) is hydrolyzed in the presence of an acid catalyst or a base catalyst, to thereby produce a norbornane-2-spiro-α-cycloalkanone-α'-spiro-2"-norbornane-5,5",6,6"-tetracarboxylic acid; and after that, the obtained norbornane-2-spiro-α-cycloalkanone-α'-spiro-2"-norbornane-5,5",6,6"-tetracarboxylic acid is subjected to dehydrative ring-closure by heating or by use of a dehydrating agent, to thereby produce the tetracarboxylic dianhydride represented by the general formula (10).

As another preferred method for obtaining the tetracarboxylic dianhydride represented by the general formula (10), for example, a method may be employed in which after the compound represented by the general formula (11) is obtained by conducting the first step, a mixture liquid of the compound represented by the general formula (11) with a lower carboxylic acid (formic acid, acetic acid, propionic acid, or the like) and an acid catalyst is prepared; and the mixture is heated under reflux, to thereby obtain the compound represented by the general formula (10) from the compound represented by the general formula (11). In the step of heating under reflux, it is preferable to conduct the heating under reflux, while distilling off the produced carboxylic acid ester and water from the mixture liquid together with the lower carboxylic acid during the heating under reflux, and while continuously adding the lower carboxylic acid so that the amount of lower carboxylic acid can be constant. Note that the amount of the lower carboxylic acid (formic acid, acetic acid, propionic acid, or the like) used in the method is preferably such that the amount of moles of the lower carboxylic acid is 4 to 1000 times (particularly preferably about 50 times) the amount of moles of the compound represented by the general formula (11). In addition, a temperature condition of the heating under reflux is preferably 100° C. to 180° C., and more preferably 100° C. to 140° C. Moreover, a time of the heating under reflux is preferably about 5 to 50 hours. Note that after the reaction is allowed to proceed by the heating under reflux as described above, the compound represented by the general formula (10) can be precipitated by allowing the mixture liquid to stand at about room temperature (25° C.).

Note that the thus obtained tetracarboxylic dianhydride represented by the general formula (10) contains six stereoisomers (cis-endo-endo isomer, cis-exo-endo isomer, cis-exo-exo isomer, trans-endo-endo isomer, trans-exo-endo isomer, and trans-exo-exo isomer), including the alicyclic tetracarboxylic dianhydrides represented by the general formulae (7) and (8). For this reason, in the first method for producing the alicyclic tetracarboxylic dianhydride of the present invention, the tetracarboxylic dianhydride represented by the general formula (10) is produced, and then the alicyclic tetracarboxylic dianhydrides represented by the general formulae (7) and (8) are separated and taken out from the compound represented by the general formula (10), so that the purity of the alicyclic tetracarboxylic dianhydrides represented by the general formulae (7) and (8) can be 90% by mole or higher. Thus, the above-described alicyclic tetracarboxylic dianhydride of the present invention is obtained.

A method for separating and taking out the alicyclic tetracarboxylic dianhydrides represented by the general formulae (7) and (8) from the compound represented by the general formula (10) as described above is not particularly limited, and a known method capable of separating a desired isomer from a group of compounds can be employed, as appropriate. For example, a recrystallization method (including a crystallization method) or an adsorptive separation method may be employed.

The recrystallization method which can be employed for separating and taking out the alicyclic tetracarboxylic dianhydrides represented by the general formulae (7) and (8) from the compound represented by the general formula (10) is not particularly limited, and conditions of the recrystallization method may be set, as appropriate, depending on the kind of the alicyclic tetracarboxylic dianhydride represented by the general formula (7) and/or the general formula (8). For example, a method can be employed in which the compound represented by the general formula (10) dissolved in a solvent under a temperature condition of $-40°$ C. to $200°$ C., and then recrystallized at a temperature lower than the dissolving temperature, so that the alicyclic tetracarboxylic dianhydrides represented by the general formulae (7) and (8) are selectively separated.

The solvent which can be used in the recrystallization method is not particularly limited, and examples thereof include hydrocarbon-based solvents such as pentane, hexane, heptane, and petroleum ether; aromatic solvents such as benzene, toluene, and xylene; ester-based solvents such as ethyl acetate; ether-based solvents such as ethyl ether, isopropyl ether, THF, and dioxane; nitrile-based solvents such as acetonitrile and propionitrile; polar solvents such as DMF, DMAc, NMP, and DMSO; halogen-containing solvents such as methylene chloride, chloroform, and chlorobenzene; carboxylic acid-based solvents such as formic acid, acetic acid, propionic acid, and acetic anhydride; and the like.

In addition, a temperature condition for dissolving the compound represented by the general formula (10) in the solvent is preferably $-40°$ C. to $200°$ C., and more preferably 0 to $150°$ C. If the temperature exceeds the upper limit, there is a tendency that the compound represented by the general formula (10) is decomposed by impurities such as water, alcohol, or amine, so that the alicyclic tetracarboxylic dianhydrides represented by the general formulae (7) and (8) cannot be obtained. Meanwhile, if the temperature is lower than the lower limit, the alicyclic tetracarboxylic dianhydride tends to be insufficiently dissolved in the solvent.

In addition, when such a recrystallization method is employed, the amount of the solvent used is such that the volume of the solvent is preferably 0.5 to 500 times (V/V), and more preferably 1 to 100 times (V/V) the volume of the compound represented by the general formula (10). If the amount (ratio) of the solvent used is less than the lower limit, the alicyclic tetracarboxylic dianhydride tends to be insufficiently dissolved in the solvent. Meanwhile, if the amount (ratio) of the solvent used exceeds the upper limit, the alicyclic tetracarboxylic dianhydrides represented by the general formulae (7) and (8) tend to be insufficiently precipitated, and the percentage yield thereof tends to decrease.

Meanwhile, as the adsorptive separation method which can be employed for separating and taking out the alicyclic tetracarboxylic dianhydrides represented by the general formulae (7) and (8) from the compound represented by the general formula (10), it is possible to employ, for example, a method in which a solution is obtained by dissolving the compound represented by the general formula (10) in a solvent and then the alicyclic tetracarboxylic dianhydrides represented by the general formulae (7) and (8) are selectively separated by using a known adsorbent, as appropriate, and by employing a known adsorptive separation technique such as adsorbent addition, column chromatography, HPLC, filtration, or solid-liquid extraction, depending on the target alicyclic tetracarboxylic dianhydrides represented by the general formulae (7) and (8), or the like. Note that when the filtration using an adsorbent is employed, a method may be employed in which, after the solution is obtained by dissolving the compound represented by the general formula (10) in a solvent as described above, recrystallization is conducted and the precipitated alicyclic tetracarboxylic dianhydrides represented by the general formulae (7) and (8) are filtered, and the remaining portion dissolved in the solvent is adsorbed onto the adsorbent, and the alicyclic tetracarboxylic dianhydrides represented by the general formulae (7) and (8) are obtained.

Adsorbents which can be used for the adsorptive separation are not particularly limited, and include Celite, silica gel, alumina, activated clay, silica alumina, zeolite, activated carbon, carbon nanotube, charcoal, ion-exchange resins, and the like.

Meanwhile, examples of the solvent used for the adsorptive separation method include hydrocarbon-based solvents such as pentane, hexane, heptane, and petroleum ether; aromatic solvents such as benzene, toluene, and xylene; ester-based solvents such as ethyl acetate; ether-based solvents such as ethyl ether, isopropyl ether, THF, and dioxane; nitrile-based solvents such as acetonitrile and propionitrile; halogen-containing solvents such as methylene chloride, chloroform, and chlorobenzene; and the like.

Moreover, when the alicyclic tetracarboxylic dianhydrides represented by the general formulae (7) and (8) are selectively separated by the above-described separation technique, it is possible to employ, for example, a method in which specific isomers are adsorbed onto and desorbed from the adsorbent by utilizing the polarity of the solvent in the solution, or a method in which the alicyclic tetracarboxylic dianhydrides represented by the general formulae (7) and (8) are adsorbed onto and desorbed from the adsorbent by changing the temperature. The separation method can be changed, as appropriate, depending on the kind of the alicyclic tetracarboxylic dianhydride represented by the general formula (7) and/or the general formula (8) to be separated.

In addition, a temperature condition for separating the compound by the adsorptive separation method is preferably $-40°$ C. to $200°$ C., and more preferably 0 to $100°$ C. If the temperature exceeds the upper limit, there is a tendency that the compound represented by the general formula (10) is decomposed by impurities such as water, an alcohol, an amine, or the like, and the alicyclic tetracarboxylic dianhydrides represented by the general formulae (7) and (8) cannot be obtained. Meanwhile, if the temperature is lower than the lower limit, the alicyclic tetracarboxylic dianhydride tends to be insufficiently dissolved in the solvent.

In addition, when the adsorptive separation method is employed, the amount of the solvent used is such that the volume of the solvent is preferably 0.5 to 500 times (V/V), and more preferably 2 to 100 times (V/V) the volume of the compound represented by the general formula (10). If the amount (ratio) of the solvent used is less than the lower limit, the alicyclic tetracarboxylic dianhydride tends to be insufficiently dissolved in the solvent. Meanwhile, if the amount (ratio) of the solvent used exceeds the upper limit, there is a tendency that the obtained solution of the alicyclic tetracarboxylic dianhydride become thin, and that the operation efficiency and the recovery ratio are lowered.

By separating the alicyclic tetracarboxylic dianhydrides represented by the general formulae (7) and (8), while changing the separation conditions, as appropriate, depending on the kind of the target compound as described above, the purity of the alicyclic tetracarboxylic dianhydrides represented by the general formulae (7) and (8) can be 90% by mole or higher in the compound after the separation. Thus, the alicyclic tetracarboxylic dianhydride of the present invention can be obtained.

Hereinabove, a description is given of the first method preferable as the method for producing the alicyclic tetracarboxylic dianhydride of the present invention (the method in which the alicyclic tetracarboxylic dianhydride of the present invention is obtained by producing the compound represented by the general formula (9), then converting the compound represented by the general formula (9) to a tetracarboxylic dianhydride to obtain the tetracarboxylic dianhydride represented by the following general formula (10), and then separating and taking out the alicyclic tetracarboxylic dianhydrides represented by the general formulae (7) and (8) from the tetracarboxylic dianhydride represented by the general formula (10)). Hereinafter, the above-mentioned second and third methods are described.

The second method for producing the alicyclic tetracarboxylic dianhydride of the present invention is a method in which the alicyclic tetracarboxylic dianhydride of the present invention is obtained by preparing the compound represented by the general formula (9), separating and taking out the cis-endo-endo isomer and/or the trans-endo-endo isomer of the compound represented by the general formula (9), so that the purity of the cis-endo-endo isomer and/or the trans-endo-endo isomer can be 90% by mole or higher, and converting the cis-endo-endo isomer and/or the trans-endo-endo isomer to a tetracarboxylic dianhydride, to thereby obtain an alicyclic tetracarboxylic dianhydride comprising the alicyclic tetracarboxylic dianhydrides represented by the general formulae (7) and (8) in an amount of 90% by mole or more in total. As the method for converting the cis-endo-endo isomer and/or the trans-endo-endo isomer of the compound represented by the general formula (9) to a tetracarboxylic dianhydride in the second method, it is possible to employ the same method as the method for converting the compound represented by the general formula (9) to a tetracarboxylic dianhydride described above in the first method.

Meanwhile, the method for separating and taking out, from the compound represented by the general formula (9), the cis-endo-endo isomer and/or the trans-endo-endo isomer of the compound is not particularly limited, and a known method can be employed, as appropriate. For example, a recrystallization method or an adsorptive separation method can be employed, as appropriate.

The method for the recrystallization method is not particularly limited, and conditions thereof can be changed, as appropriate, depending on the kinds of the compound represented by the general formula (9) and the target isomer, and the like. For example, a method can be employed in which the compound represented by the general formula (9) is dissolved in a solvent under a temperature condition of −40° C. to 120° C., and then recrystallized at a temperature lower than the dissolving temperature, so that the cis-endo-endo isomer and/or the trans-endo-endo isomer of the compound represented by the general formula (9) is selectively separated.

In addition, when the recrystallization method is employed as the method for separating and taking out, from the compound represented by the general formula (9), the cis-endo-endo isomer and/or the trans-endo-endo isomer of the compound, solvents which can be preferably used for the recrystallization method include alcohol-based solvents such as methanol, ethanol, and propanol; and hydrocarbon-based solvents such as pentane, hexane, heptane, and petroleum ether.

In addition, a temperature condition for dissolving the compound represented by the general formula (9) in the solvent is preferably −40° C. to 120° C., and more preferably 0 to 100° C. If the temperature exceeds the upper limit, there is a tendency that the compound represented by the general formula (9) is decomposed by the retro-Diels-Alder reaction, and the alicyclic tetracarboxylic dianhydrides represented by the general formulae (7) and (8) cannot be obtained. Meanwhile, if the temperature is lower than the lower limit, the compound represented by the general formula (9) tends to be dissolved insufficiently.

Moreover, when such a recrystallization method is employed, the amount of the solvent used is such that the volume of the solvent used is preferably 0.5 to 100 times (V/V), and more preferably 1 to 50 times (V/V) the volume of the compound represented by the general formula (9). If the amount (ratio) of the solvent used is less than the lower limit, the compound represented by the general formula (9) tends to be insufficiently dissolved in the solvent. Meanwhile, if the amount (ratio) of the solvent used exceeds the upper limit, there is a tendency that the compound represented by the general formula (9) is insufficiently precipitated, so that the percentage yield decreases.

In addition, when the adsorptive separation method is employed as the method for separating and taking out, from the compound represented by the general formula (9), the cis-endo-endo isomer and/or the trans-endo-endo isomer of the compound, the adsorptive separation method is not particularly limited, and conditions thereof can be changed, as appropriate, depending on the kinds of the compound represented by the general formula (9) and the target isomer and the like. For example, it is possible to employ a method in which, first, a solution is obtained by dissolving the compound represented by the general formula (9) in a solvent, and then the cis-endo-endo isomer and/or the trans-endo-endo isomer is selectively separated by using a known adsorbent, as appropriate, and by employing a known adsorptive separation technique such as adsorbent addition, column chromatography, HPLC, filtration, or solid-liquid extraction, depending on the target cis-endo-endo isomer and/or trans-endo-endo isomer of the compound represented by the general formula (9), or the like. Note that when the filtration using an adsorbent is employed, a method may be employed in which after the solution is obtained by dissolving the compound represented by the general formula (9) in a solvent as mentioned above, the cis-endo-endo isomer and/or the trans-endo-endo isomer of the compound represented by the general formula (9) is precipitated by recrystallization, and then a portion of cis-endo-endo isomer and/or the trans-endo-endo isomer dissolved in the solvent is filtered by using an adsorbent.

When an adsorptive separation method is employed as the method for separating and taking out, from the compound represented by the general formula (9), the cis-endo-endo isomer and/or the trans-endo-endo isomer of the compound, a method can be employed which is basically the same as the adsorptive separation method employable for separating and taking out the alicyclic tetracarboxylic dianhydrides represented by the general formulae (7) and (8) from the compound represented by the general formula (10), except that the temperature condition and the like are changed, as appropriate, depending on the kind of the cis-endo-endo isomer and/or the trans-endo-endo isomer. In addition, when the compound is separated by the adsorptive separation method, the temperature condition is preferably −40° C. to 120° C., and more preferably 0 to 100° C. If the temperature exceeds the upper limit, there is a tendency that the compound represented by the general formula (9) is decomposed by the retro Diels-Alder reaction, and the alicyclic tetracarboxylic dianhydrides represented by the general formulae (7) and (8) cannot be obtained. Meanwhile, if the temperature is lower than the lower limit, the compound represented by the general formula (9) tends to be insufficiently dissolved in the solvent.

Next, the above-mentioned third method for producing the alicyclic tetracarboxylic dianhydride of the present invention is described. The third method is a method in which the alicyclic tetracarboxylic dianhydride of the present invention is obtained by preparing the compound represented by the general formula (9); separating and taking out the cis-endo-endo isomer and/or the trans-endo-endo isomer from a compound (ester or carboxylic acid: the compound represented by the general formula (11)) obtained by subjecting the compound represented by the general formula (9) to esterification (subsequently, the ester may be converted to a carboxylic acid by conducting a hydrolysis treatment or a transesterification reaction with a carboxylic acid), so that the purity of the cis-endo-endo isomer and/or the trans-endo-endo isomer can be 90% by mole or higher; and converting the cis-endo-endo isomer and/or the trans-endo-endo isomer to an acid dianhydride, to thereby obtain an alicyclic tetracarboxylic dianhydride comprising the alicyclic tetracarboxylic dianhydrides represented by the general formulae (7) and (8) in an amount of 90% by mole or more. When this method is carried out, the methods described above in the first method can be used as the method for obtaining the compound represented by the general formula (11) and the subsequent method for converting the tetracarboxylic acid or the ester to an acid dianhydride.

In addition, the method for separating and taking out, from the compound represented by the general formula (11), the cis-endo-endo isomer and/or the trans-endo-endo isomer of the compound is not particularly limited, and a known method can be employed, as appropriate. A recrystallization method or an adsorptive separation method can be employed, as appropriate.

The method for the recrystallization method is not particularly limited, and conditions thereof can be changed, as appropriate, depending on the kinds of the compound represented by the general formula (11) and the target isomer and the like. As the recrystallization method, for example, a method can be employed in which the compound represented by the general formula (11) is dissolved in a solvent under a temperature condition of −40° C. to 200° C., and then recrystallized at a temperature lower than the dissolving temperature, to thereby selectively separate the cis-endo-endo isomer and/or the trans-endo-endo isomer of the compound represented by the general formula (11).

When the recrystallization method is employed as the method for separating and taking out the cis-endo-endo isomer and/or the trans-endo-endo isomer from the compound represented by the general formula (11), solvents which can be preferably used for the recrystallization method include alcohol-based solvents such as methanol, ethanol, and propanol; hydrocarbon-based solvents such as pentane, hexane, heptane, and petroleum ether; aromatic solvents such as benzene, toluene and xylene; ester-based solvents such as ethyl acetate; ether-based solvents such as ethyl ether, isopropyl ether, THF, and dioxane; nitrile-based solvents such as acetonitrile and propionitrile; polar solvents such as DMF, DMAc, NMP, and DMSO; and halogen-containing solvents such as methylene chloride, chloroform, and chlorobenzene.

In addition, a temperature condition for dissolving the compound represented by the general formula (11) in the solvent is preferably −40° C. to 200° C., and more preferably 0 to 150° C. If the temperature exceeds the upper limit, there is a tendency that the compound represented by the general formula (11) is decomposed by water, oxygen, or the like, and the alicyclic tetracarboxylic dianhydrides represented by the general formulae (7) and (8) cannot be obtained. Meanwhile, if the temperature is lower than the lower limit, the compound represented by the general formula (11) tends to be insufficiently dissolved in the solvent.

Moreover, when such a recrystallization method is employed, the amount of the solvent used is such that the volume of the solvent used is preferably 0.5 to 100 times (V/V), and more preferably 1 to 50 times (V/V) the volume of the compound represented by the general formula (11). If the amount (ratio) of the solvent used is less than the lower limit, the compound represented by the general formula (11) tends to be insufficiently dissolved. Meanwhile, if the amount (ratio) of the solvent used exceeds the upper limit, there is a tendency that the compound represented by the general formula (11) is insufficiently precipitated, and the percentage yield decreases.

In addition, when the adsorptive separation method is employed as the method for separating and taking out, from the compound represented by the general formula (11), the cis-endo-endo isomer and/or the trans-endo-endo isomer of the compound, a method can be employed which is basically the same as the adsorptive separation method employable for separating and taking out the alicyclic tetracarboxylic dianhydrides represented by the general formulae (7) and (8) from the compound represented by the general formula (10), except that the temperature condition and the like are changed, as appropriate, depending on the kind of the cis-endo-endo isomer and/or the trans-endo-endo isomer.

Hereinabove, the methods preferable as the method for producing the alicyclic tetracarboxylic dianhydride of the present invention are described. Hereinafter, a method preferable as a method for producing the polyimide of the present invention is described.

The method for producing the polyimide of the present invention is not particularly limited, and for example, a method can be preferably employed which comprises:

a step (Step (I)) of reacting the alicyclic tetracarboxylic dianhydride of the present invention with an aromatic diamine represented by the following general formula (14):

[Chem. 15]

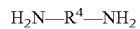 (14)

[in the formula (14), $R^4$ represents an aryl group having 6 to 40 carbon atoms] in the presence of an organic solvent, to thereby prepare a polyamic acid comprising at least one of repeating units represented by the following general formulae (15) and (16):

[Chem. 16]

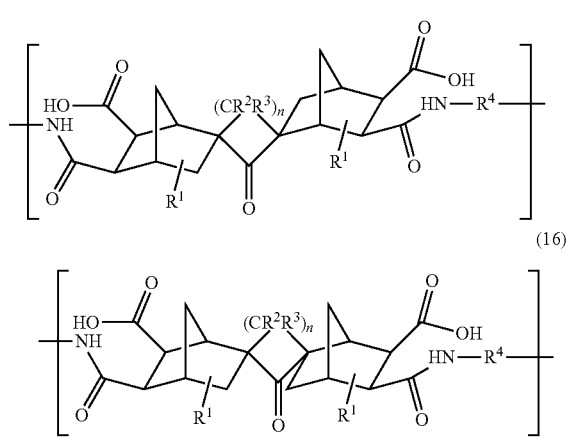

[in the formulae (15) and (16), $R^1$, $R^2$, $R^3$, and n have the same meanings as those of $R^1$, $R^2$, $R^3$, and n in the general formulae (7) and (8), and $R^4$ has the same meaning as that of $R^4$ in the general formula (14)], in which the total amount of the repeating units represented by the general formulae (15) and (16) is 90% by mole or more, and thereby obtain a solution of the polyamic acid; and a step (Step (II)) of subjecting the polyamic acid to imidization, to thereby obtain the polyimide of the present invention. The step (I) and the step (II) are described separately below.

(Step (I))

The step (I) is a step of reacting the above-described alicyclic tetracarboxylic dianhydride of the present invention with an aromatic diamine represented by the general formula (14) in the presence of an organic solvent, to thereby prepare a polyamic acid and obtain a solution of the polyamic acid.

The alicyclic tetracarboxylic dianhydride used in the step (I) is the above-described alicyclic tetracarboxylic dianhydride of the present invention, which comprises the alicyclic tetracarboxylic dianhydrides represented by the general formulae (7) and (8) in an amount of 90% by mole or more in total. Note that when an alicyclic tetracarboxylic dianhydride comprising multiple tetracarboxylic dianhydrides represented by the general formulae (1) and (2) among which the types of any one or more of $R^1$, $R^2$, $R^3$, and n are different is used as the alicyclic tetracarboxylic dianhydride of the present invention, the characteristics (characteristics such as glass transition temperature and linear expansion coefficient) of the obtained polyimide can be changed, as appropriate, by changing the types, as appropriate.

Regarding the diamine compound represented by the general formula (14) used in the step (I), $R^4$ in the general formula (14) is the same as $R^4$ in the general formulae (1) and (2), and preferred ones thereof are the same as those of $R^4$ in the general formulae (1) and (2). $R^4$ in the general formula (14) may be changed, as appropriate, depending on the structure of the target polyimide.

Examples of the aromatic diamine represented by the general formula (14) include-4,4'-diaminodiphenylmethane, 4,4''-diamino-p-terphenyl, 3,3'-diaminodiphenylmethane, 4,4'-diaminodiphenylethane, 3,3'-diaminodiphenylethane, 4,4'-diaminobiphenyl, 3,3'-diaminobiphenyl, 4,4'-diaminodiphenyl ether, 3,3'-diaminodiphenyl ether, 2,2-bis(4-aminophenoxyphenyl)propane, 1,3-bis(4-aminophenoxy)benzene, 1,3-bis(3-aminophenoxy)benzene, bis[4-(4-aminophenoxy)phenyl]sulfone, bis[4-(3-aminophenoxy)phenyl]sulfone, 2,2'-bis(trifluoromethyl)-4,4'-diaminobiphenyl, 3,4'-diaminodiphenyl ether, 4,4'-diaminobenzophenone, 3,3'-diaminobenzophenone, 9,9-bis(4-aminophenyl)fluorene, p-diaminobenzene (also referred to as p-phenylenediamine), m-diaminobenzene, o-diaminobenzene, 4,4'-diaminobiphenyl, 3,3'-diaminobiphenyl, 2,2'-diaminobiphenyl, 3,4'-diaminobiphenyl, 2,6-diaminonaphthalene, 1,4-diaminonaphthalene, 1,5-diaminonaphthalene, 4,4'-[1,3-phenylenebis(1-methyl-ethylidene)]bisaniline, 4,4'-[1,4-phenylenebis(1-methyl-ethylidene)]bisaniline, 2,2'-dimethyl-4,4'-diaminobiphenyl (also referred to as o-tolidine), 3,3'-dimethyl-4,4'-diaminobiphenyl, 3,3'-diaminodiphenyl sulfone, 4,4'-diaminodiphenyl sulfone, 4,4'-diaminodiphenyl sulfide, 1,4-bis(4-aminophenoxy)benzene, 4,4'-bis(4-aminophenoxy)biphenyl, 4,4'-diaminobenzanilide, 4,4'-diaminophenyl benzoate (also referred to as 4,4'-diaminodiphenyl ester), 9,9'-bis(4-aminophenyl)fluorene, o-tolidine sulfone, 1,3'-bis(4-aminophenoxy)-2,2-dimethylpropane, 2,3,5,6-tetramethyl-1,4-phenylenediamine, 3,3',5,5'-tetramethylbenzidine, 1,5-bis(4-aminophenoxy)pentane, diethyltoluenediamine, aminobenzylamine, bisaniline M, bisaniline P, and the like. A method for producing such an aromatic diamine is not particularly limited, and a known method can be employed, as appropriate. In addition, as the aromatic diamine, a commercially available aromatic diamine can be used as appropriate.

In addition, from the viewpoint that the linear expansion coefficient of the obtained polyimide can be adjusted to a lower value within the above-described preferred numeric value range, $R^4$ in the aromatic diamine represented by the general formula (14) is more preferably a group represented by the general formula (5) or (6), and especially preferably a group represented by the general formula (5) or a group represented by the general formula (6), where Q is at least one of groups represented by —CONH—, —COO⁻, —CO—, and —$C_6H_4$— (more preferably a group represented by —CONH— or —COO⁻, and particularly preferably a group represented by —CONH—). In addition, from the viewpoint of also providing a higher flexibility in a case where a film is formed from the obtained polyimide, $R^4$ of the aromatic diamine represented by the general formula (14) is preferably a group selected from the group consisting of the group represented by the general formula (3); and groups represented by the general formula (6), where Q is one of the groups represented by —O—, —S—, —$CH_2$—, and —O—$C_6H_4$—O—. In addition, from the viewpoint of availability, $R^4$ in the aromatic diamine represented by the general formula (14) is preferably a group represented by the general formula (6), where Q is one of the groups represented by —O—, —$CH_2$—, and —O—$C_6H_4$—O— (more preferably one of the groups represented by —O— and —$CH_2$—, and further preferably the group represented by —O—).

Moreover, as the aromatic diamine represented by the general formula (14), it is preferable to use a combination of multiple (two or more) aromatic diamines having different kinds of $R^4$ in the general formula (14), from the viewpoints that the glass transition temperature and the linear expansion coefficient of the polyimide can be within the preferred numeric value ranges, and that a polyimide which can achieve the glass transition temperature, the linear expansion coefficient, and, when a film is formed, the flexibility at higher levels in a balanced manner is prepared more reliably. In addition, from the similar viewpoints, the multiple (two or more) aromatic diamines having different kinds of $R^4$ more preferably comprise at least an aromatic diamine represented by the general formula (14), where R⁴ is a group selected from the group consisting of the groups represented by the general formula (5); and the groups represented by the general formula (6), where Q is at least one of the groups represented by —CONH—, —COO—, —CO—, and —C₆H₄— (more preferably a group represented by —CONH— or —COO—, and particularly preferably the group represented by —CONH—), and an aromatic diamine represented by the general formula (14), where R⁴ is a group selected from the group consisting of the group represented by the general formula (3); and the groups represented by the general formula (6), where Q is one of the groups represented by —O—, —S—, —CH₂—, and —O—C₆H₄—O— (more preferably one of the groups represented by —O— and —CH₂—, and further preferably the group represented by —O—), because a higher effect can be obtained.

In addition, the organic solvent used in the step (I) is preferably an organic solvent capable of dissolving both the above-described alicyclic tetracarboxylic dianhydride of the present invention and the aromatic diamine represented by the general formula (14). Examples of such an organic solvent include aprotic polar solvents such as N-methyl-2-pyrrolidone, N,N-dimethylacetamide, N,N-dimethylformamide, N,N'-dimethylimidazole, dimethyl sulfoxide, γ-butyrolactone, propylene carbonate, tetramethylurea, 1,3-dimethyl-2-imidazolidinone, hexamethylphosphoric triamide, and pyridine; phenol-based solvents such as m-cresol, xylenol, phenol, and halogenated phenols; ether-based solvents such as tetrahydrofuran, dioxane, cello solves, and glymes; aromatic solvents such as benzene, toluene, xylene, and 2-chloro-4-hydroxytoluene; and the like. One of these organic solvents may be used alone, or two or more thereof may be used as a mixture.

In addition, the ratio between the above-described alicyclic tetracarboxylic dianhydride of the present invention and the aromatic diamine represented by the general formula (14) used in the step (I) is such that the acid anhydride groups of the alicyclic tetracarboxylic dianhydride of the present invention is preferably 0.2 to 2 equivalents, and more preferably 0.3 to 1.2 equivalents, relative to 1 equivalent of the amino groups of the aromatic diamine represented by the general formula (14). If the ratio of the use is less than the lower limit, there is a tendency that the polymerization reaction proceeds inefficiently, so that a polyamic acid having a high molecular weight cannot be obtained. Meanwhile, if the ratio of the use exceeds the upper limit, there is a tendency that a polyamic acid with a high molecular weight cannot be obtained, as in the above-described case.

Moreover, when the above-described alicyclic tetracarboxylic dianhydride of the present invention and the aromatic diamine represented by the general formula (14) are used, the mole ratio ([the alicyclic tetracarboxylic dianhydride of the present invention]:[the diamine compound]) is preferably 0.5:1.0 to 1.0:0.5 (more preferably 0.9:1.0 to 1.0:0.9). If the amount of the alicyclic tetracarboxylic dianhydride of the present invention used is less than the lower limit, the yield of the polyimide tends to decrease. Meanwhile, also if the amount of the alicyclic tetracarboxylic dianhydride exceeds the upper limit, the yield of the polyimide tends to decrease.

Moreover, the amount of the organic solvent used in the step (I) is preferably such an amount that the total amount of the above-described alicyclic tetracarboxylic dianhydride of the present invention and the aromatic diamine represented by the general formula (14) can be 0.1 to 50% by mass (more preferably 10 to 30% by mass) relative to the total amount of the reaction solution. If the amount of the organic solvent used is less than the lower limit, there is a tendency that the polyamic acid cannot be obtained efficiently. Meanwhile, if the amount of the organic solvent used exceeds the upper limit, stirring tends to be difficult because of the increase in viscosity.

In addition, a base compound may be further added to the organic solvent in reacting the above-described alicyclic tetracarboxylic dianhydride of the present invention with the aromatic diamine represented by the general formula (14) in the step (I), from the viewpoints of improving the reaction rate and obtaining the polyamic acid with a high degree of polymerization. The basic compound is not particularly limited, and examples thereof include triethylamine, tetrabutylamine, tetrahexylamine, 1,8-diazabicyclo[5.4.0]-undecene-7, pyridine, isoquinoline, N-methylpiperidine, α-picoline, and the like. In addition, the amount of the base compound used is preferably 0.001 to 10 equivalents, and more preferably 0.01 to 0.1 equivalents, relative to 1 equivalent of the above-described alicyclic tetracarboxylic dianhydride of the present invention. If the amount of the base compound used is less than the lower limit, there is a tendency that an effect of the addition is not observed. Meanwhile, if the amount of the base compound used exceeds the upper limit, coloring and the like tends to be caused.

In addition, a reaction temperature in reacting the above-described alicyclic tetracarboxylic dianhydride of the present invention with the aromatic diamine represented by the general formula (14) in the step (I) is not particularly limited, and may be adjusted, as appropriate, to a temperature at which these compounds can be reacted with each other. The reaction temperature is preferably 80° C. or below, and preferably −30 to 30° C. In addition, a method for reacting the above-described alicyclic tetracarboxylic dianhydride of the present invention with the aromatic diamine represented by the general formula (14) employable in the step (I) is not particularly limited, and a method capable of conducting a polymerization reaction of a tetracarboxylic dianhydride with an aromatic diamine can be used, as appropriate. For example, a method may be employed in which the aromatic diamine is dissolved in a solvent under an inert atmosphere of nitrogen, helium, argon, or the like under atmospheric pressure; then the alicyclic tetracarboxylic dianhydride of the present invention is added at the above-described reaction temperature; and then the reaction is allowed to proceed for 10 to 48 hours. If any one of the reaction temperature and the reaction time is lower or less than the lower limit, it tends to be difficult to conduct the reaction sufficiently. Meanwhile, if any one of the reaction temperature and the reaction time exceeds the upper limit, there is a tendency that the possibility of inclusion of a substance (oxygen or the like) which degrades the polymerization product is increased, so that the molecular weight is lowered.

By reacting the above-described alicyclic tetracarboxylic dianhydride of the present invention with the aromatic diamine represented by the general formula (14) as described above, a polyamic acid comprising at least one of repeating units represented by the general formulae (15) and (16) in which the total amount of the repeating units represented by the general formulae (15) and (16) is 90% by mole or more can be obtained. In addition, the thus obtained polyamic acid may be isolated, and then a solution of the polyamic acid to be used in the step (II) may be prepared by again dissolving the isolated polyamic acid in a solvent (for example, any of the above-described organic solvents, or the like). Alternatively, without isolating the polyamic acid, the reaction liquid obtained by reacting the above-described alicyclic tetracarboxylic dianhydride of the present invention with the aromatic diamine represented by the general formula (14) in the organic solvent (the above-described reaction liquid containing the polyamic acid) may be directly used as the solution of a polyamic acid used in the step (II). Note that when the polyamic acid is used after being isolated from the reaction liquid, the isolation method is not particularly limited, and a known method capable of isolating the polyamic acid can be employed, as appropriate. For example, a method in which the polyamic acid is isolated as a product of reprecipitation may be employed.

Note that $R^1$, $R^2$, $R^3$, and n in the general formulae (15) and (16) have the same meanings as those of $R^1$, $R^2$, $R^3$, and n in the general formulae (7) and (8), and $R^4$ has the same meaning as that of $R^4$ in the general formula (14). In other words, $R^1$, $R^2$, $R^3$, $R^4$, and n in the general formulae (15) and (16) are the same as $R^1$, $R^2$, $R^3$, $R^4$, and n in the general formulae (1) and (2), and preferred ones thereof are also the same as those of $R^1$, $R^2$, $R^3$, $R^4$ and n in the general formulae (1) and (2).

In the polyamic acid obtained in the step (I), the total amount of the repeating units represented by the general formulae (15) and (16) is 90% by mole or more. The total amount of the repeating units is originated from the total amount of the alicyclic tetracarboxylic dianhydrides represented by the general formulae (7) and (8) in the above-described alicyclic tetracarboxylic dianhydride of the present invention, and a preferred range of the total amount thereof is the same as the preferred range of the total amount of the alicyclic tetracarboxylic dianhydrides represented by the general formulae (7) and (8). Note that if the total amount of the repeating units represented by the general formulae (15) and (16) is less than 90% by mole, the polyimide of the present invention cannot be produced.

In addition, the polyamic acid obtained in the step (I) has an intrinsic viscosity [η] of preferably 0.1 to 8.0 dL/g, more preferably 0.1 to 6.0 dL/g, further preferably 0.1 to 3.0 dL/g, and particularly preferably 0.4 to 2.0 dL/g. If the intrinsic viscosity [η] is lower than 0.1 dL/g, a film obtained when a film-shaped polyimide is produced by using the polyamic acid tends to be brittle. Meanwhile, if the intrinsic viscosity [η] exceeds 8.0 dL/g, the processability deteriorates because of the excessively high viscosity, and when, for example, a film is produced, it is difficult to obtain a uniform film. In addition, the intrinsic viscosity [η] can be measured as follows. Specifically, first, by using N,N-dimethylacetamide as a solvent, a measurement sample (solution) is obtained in which the polyamic acid is dissolved in the N,N-dimethylacetamide at a concentration of 0.5 g/dL. Next, by using the measurement sample, the viscosity of the measurement sample is measured with a kinematic viscometer under a temperature condition of 30° C., and the thus determined value is employed as the intrinsic viscosity [η]. Note that an automatic viscometer manufactured by RIGO CO., LTD. (trade name: "VMC-252") is used as the kinematic viscometer.

Moreover, the polyimide obtained by the steps (I) and (II) may comprise another repeating unit in addition to the repeating units represented by the general formulae (1) and (2). In such a case, the other repeating unit may be formed, for example, by introducing a tetracarboxylic dianhydride other than the alicyclic tetracarboxylic dianhydrides represented by the general formulae (7) and (8) into the above-described alicyclic tetracarboxylic dianhydride of the present invention in the above-described step (I), by using another monomer together with the above-described alicyclic tetracarboxylic dianhydride of the present invention in the above-described step (I), by employing a method in which another diamine compound is used together with the aromatic diamine represented by the general formula (14), or even by employing an appropriate combination of any ones of these methods.

Examples of alicyclic tetracarboxylic dianhydrides which are other than the alicyclic tetracarboxylic dianhydrides represented by the general formulae (7) and (8) and which can be introduced into the above-described alicyclic tetracarboxylic dianhydride of the present invention and other monomers usable with the above-described alicyclic tetracarboxylic dianhydride of the present invention include compounds (the other isomers) which are represented by the general formula (10) and are other than the alicyclic tetracarboxylic dianhydrides represented by the general formulae (7) and (8); aliphatic or alicyclic tetracarboxylic dianhydrides such as butanetetracarboxylic dianhydride, 1,2,3,4-cyclobutanetetracarboxylic dianhydride, 1,2,3,4-cyclopentanetetracarboxylic dianhydride, 1,2,4,5-cyclohexanetetracarboxylic dianhydride, 2,3,5-tricarboxycyclopentylacetic dianhydride, 3,5,6-tricarboxynorbornane-2-acetic dianhydride, 2,3,4,5-tetrahydrofurantetracarboxylic dianhydride, 1,3,3a,4,5,9b-hexahydro-5-(tetrahydro-2,5-dioxo-3-furanyl)-naphtho[1,2-c]-furan-1,3-dione, 1,3,3a,4,5,9b-hexahydro-5-methyl-5-(tetrahydro-2,5-dioxo-3-furanyl)-naphtho[1,2-c]-furan-1,3-dione, 1,3,3a,4,5,9b-hexahydro-8-methyl-5-(tetrahydro-2,5-dioxo-3-furanyl)-naphtho[1,2-c]-furan-1,3-dione, 5-(2,5-dioxotetrahydrofural)-3-methyl-3-cyclohexene-1,2-dicarboxylic dianhydride, and bicyclo[2,2,2]-oct-7-ene-2,3,5,6-tetracarboxylic dianhydride; aromatic tetracarboxylic dianhydrides such as pyromellitic dianhydride, 3,3',4,4'-benzophenonetetracarboxylic dianhydride, 3,3',4,4'-biphenylsulfonetetracarboxylic dianhydride, 1,4,5,8-naphthalenetetracarboxylic dianhydride, 2,3,6,7-naphthalenetetracarboxylic dianhydride, 3,3',4,4'-biphenyl ether tetracarboxylic dianhydride, 3,3',4,4'-dimethyldiphenylsilanetetracarboxylic dianhydride, 3,3',4,4'-tetraphenylsilanetetracarboxylic dianhydride, 1,2,3,4-furantetracarboxylic dianhydride, 4,4'-bis(3,4-dicarboxyphenoxy)diphenyl sulfide dianhydride, 4,4'-bis(3,4-dicarboxyphenoxy)diphenyl sulfone dianhydride, 4,4'-bis(3,4-dicarboxyphenoxy)diphenylpropane dianhydride, 3,3',4,4'-perfluoroisopropylidenediphthalic dianhydride, 4,4'-(2,2-hexafluoroisopropylidene)diphthalic dianhydride, 3,3',4,4'-biphenyltetracarboxylic dianhydride, 2,3,3',4'-biphenyltetracarboxylic dianhydride, bis(phthalic acid) phenylphosphine oxide dianhydride, p-phenylene-bis(triphenylphthalic)dianhydride, m-phenylene-bis(triphenylphthalic)dianhydride, bis(triphenylphthalic acid)-4,4'-diphenyl ether dianhydride, and bis(triphenylphthalic acid)-4,4'-diphenylmethane dianhydride; and the like. Note that when an aromatic tetracarboxylic acid is used, the amount of the aromatic tetracarboxylic acid used is preferably changed, as appropriate, within a range in which the obtained polyimide can have a sufficient transparency, in order to prevent coloring due to the intramolecular CT.

Meanwhile, the diamine compound other than the above-described aromatic diamines is not particularly limited, and a known diamine compound which can be used for production of a polyimide or a polyamic acid can be used, as appropriate. For example, aliphatic diamines, alicyclic diamines, and the like can be used, as appropriate. Examples of the aliphatic diamines include ethylenediamine, propylenediamine, trimethylenediamine, tetramethylenediamine, hexamethylenediamine, polyoxyalkylenediamine, and the like. Examples of the alicyclic diamines include 4,4'-diamino-dicyclohexylmethane, 3,3'-dimethyl-4,4'-diamino-dicyclohexylmethane, 3,3'-diethyl-4,4'-diamino-dicyclohexylmethane, 3,3',5,5'-tetramethyl-4,4'-diamino-dicyclohexylmethane 3,3',5,5'-tetraethyl-4,4'-diamino-dicyclohexylmethane, 3,5-diethyl-3',5'- dimethyl-4,4'-diaminodicyclohexylmethane, bis(aminomethyl)cyclohexane, 1,4-diaminocyclohexane, 1,3-diaminocyclohexane, bicyclo[2.2.1]heptanedimethanamine, norbornanediamine, and the like.

(Step (II))

Next, the step (II) is described. The step (II) is a step of subjecting the polyamic acid obtained in the step (I) to imidization, to thereby obtain the polyimide of the present invention.

A method for the imidization of the polyamic acid obtained in the step (I) is not particularly limited, as long as the imidization of the polyamic acid can be conducted by this method, and a known method can be employed, as appropriate. For example, it is preferable to employ a method in which the polyamic acid is subjected to imidization by performing a heat treatment for dehydration reaction, or a method in which the imidization is conducted by using a so-called "imidization agent."

When the method in which dehydration reaction is conducted by performing a heat treatment (the method for the imidization by performing a heat treatment) is employed as the method for the imidization of the polyamic acid, the heat treatment is preferably conducted under a temperature condition of 200 to 450° C. (preferably 250 to 440° C., more preferably 300 to 430° C., further preferably 350 to 420° C., and particularly preferably 360° C. to 410° C.). If the heating temperature is lower than 200° C. in a case where the imidization method by performing a heat treatment and thereby performing the dehydration reaction is employed, the equilibrium tends to favor the reaction in which the polyamic acid is decomposed to the acid dianhydride and the amine over the reaction in which the polyamic acid is converted to the polyimide by dehydrative ring-closure. Meanwhile, if the heating temperature exceeds the upper limit, coloring, decrease in molecular weight due to thermal decomposition, or the like tends to occur.

In addition, when the method for the imidization by performing the heat treatment is employed, the following method for the imidization is preferably employed. Specifically, as the solution of the polyamic acid for the imidization, the reaction liquid (the reaction liquid containing the polyamic acid) obtained by reacting the above-described alicyclic tetracarboxylic dianhydride of the present invention with the aromatic diamine represented by the general formula (14) in the organic solvent in the step (I) is used, as it is, without isolating the polyamic acid. The solution of the polyamic acid (the reaction liquid) is subjected to a drying treatment to remove the solvent, and then to a heat treatment in the above-described temperature range to conduct the imidization.

A temperature condition in the method for the drying treatment method is preferably 0 to 100° C., and more preferably 20 to 80° C. If the temperature condition in the drying treatment is lower than the lower limit, there is a tendency that the solvent is not removed by the drying. Meanwhile, if the temperature condition exceeds the upper limit, there is a tendency that the solvent boils, so that the obtained polyimide contains babbles and voids. In addition, an atmosphere in the method for the drying treatment is preferably an inert gas atmosphere (for example, a nitrogen atmosphere). In addition, a pressure condition in the drying treatment is preferably 1 to 200 mmHg, from the viewpoint of carrying out the drying more efficiently. The drying treatment enables isolation of the polyamic acid in the form of a film or the like, a subsequent heat treatment thereon, and the like.

Meanwhile, when the method for the imidization using a so-called "imidization agent" is employed, the imidization is preferably conducted in the solution of the polyamic acid in the presence of the imidization agent. As the solvent of the solution, the organic solvents described for the step (I) can be used preferably. For this reason, when the method for the imidization using an imidization agent is employed, it is more preferable to employ a method in which the reaction liquid (the reaction liquid containing the polyamic acid) obtained by reacting the above-described alicyclic tetracarboxylic dianhydride of the present invention with the aromatic diamine represented by the general formula (14) in the organic solvent, as it is, is used without isolating the polyamic acid obtained in the step (I) as the solution of the polyamic acid for the imidization, and the imidization is conducted by adding an imidization agent to the solution (reaction liquid) of the polyamic acid.

As the imidization agent, a known imidization agent can be used, as appropriate, and examples thereof include acid anhydrides such as acetic anhydride, propionic anhydride, and trifluoroacetic anhydride; tertiary amines such as pyridine, collidine, lutidine, triethylamine, N-methylpiperidine, and β-picoline; and the like.

In addition, a reaction temperature of the imidization in a case where the imidization is conducted by adding the imidization agent is preferably 0 to 180° C., and more preferably 60 to 150° C. In addition, the reaction time is preferably 0.1 to 48 hours. If any one of the reaction temperature and the reaction time is lower or less than the lower limit, it tends to be difficult to perform the imidization sufficiently. Meanwhile, if any one of the reaction temperature and the reaction time exceeds the upper limit, there is a tendency that the possibility of inclusion of a substance (oxygen or the like) which degrades the polymerization product is increased, so that the molecular weight is lowered. In addition, the amount of the imidization agent used is not particularly limited, and may be several millimoles to several moles (preferably about 0.05 to 1.0 mol) relative to 1 mol of the repeating units represented by the general formulae (15) and (16) in the polyamic acid.

By conducting the imidization of the polyamic acid as described above, it is possible to obtain the polyimide comprising at least one of repeating units represented by the general formulae (1) and (2), wherein a total amount of the repeating units represented by the general formulae (1) and (2) is 90% by mole or more relative to all repeating units.

In addition, the shape of the polyimide is not particularly limited, and may be a film-like shape. As a method for obtaining such a film, it is possible to employ the following method (a) or (b), for example. Specifically, in the method (a), a film made of the polyimide of the present invention is obtained by forming a coating film of the polyamic acid on a substrate, then subjecting the coating film to a drying treatment to remove the solvent, and subjecting the obtained polyamic acid in the form of the dry coating film to imidization and thermal curing. Meanwhile, in the method (b), a film made of the polyimide of the present invention is obtained by using the polyimide obtained in the form of a dry coating film on the substrate as described above or the polyimide solution obtained by the imidization by adding the imidization agent as described above, adding the polyimide or the polyimide solution to a poor solvent of the polyimide, isolating the polyimide of the present invention by conducting filtration, washing, drying, or the like, as appropriate, dissolving the isolated polyimide in an organic solvent to prepare a solution of the polyimide, applying the solution of the polyimide onto a substrate, drying the coating film, and thermally curing the dry coating film of the polyimide.

The substrate used in the methods (a) and (b) is not particularly limited, and a substrate (for example, a glass plate or a metal plate) made of a known material which can be used for film formation can be used, as appropriate, according to the shape of the desired film made of a polyimide and the like.

In addition, a method for applying the solution of the polyamic acid or the like onto the substrate is not particularly limited. For example, it is possible to employ, as appropriate, a known method such as a spin coating method, a spray coating method, a dip coating method, a dropping method, a gravure printing method, a screen printing method, a relief printing method, a die coating method, a curtain coating method, or an inkjet method.

In addition, regarding the thickness of the coating film of the polyamic acid formed on the substrate by the method (a), the thickness of the coating film after drying is preferably 1 to 200 μm, and more preferably 5 to 100 μm. If the thickness is less than the lower limit, the mechanical strength of the obtained film tends to decrease. Meanwhile, if the thickness exceeds the upper limit, the film formation processing tends to be difficult.

When a drying treatment is conducted on the coating film in the method (a), a temperature condition is preferably 0 to 100° C., and more preferably 20 to 80° C. If the temperature condition in the drying treatment is lower than the lower limit, there is a tendency that the solvent is not dried. Meanwhile, if temperature condition exceeds the upper limit, there is a tendency that the solvent boils, so that the film contains babbles and voids. In addition, an atmosphere in the drying treatment method is preferably an inert gas atmosphere (for example, a nitrogen atmosphere). Meanwhile, a pressure condition in the drying treatment is preferably 1 to 200 mmHg, from the viewpoint of carrying out the drying more efficiently. This drying treatment enables isolation of the polyamic acid in the form of a film or the like, a subsequent heat treatment, and the like.

Moreover, a method for thermally curing the dry coating film of the polyimide in the methods (a) and (b) is not particularly limited, and it is preferable to employ a method in which the dry coating film is heated at a temperature around the glass transition temperature of the polyimide (more preferably at the glass transition temperature ±40° C., further preferably at the glass transition temperature ±20° C., and particularly preferably at the glass transition temperature ±10° C.) for 0.1 to 10 hours (preferably 0.5 to 2 hours). If any of the heating temperature and the heating time is lower or less than the lower limit, there is a tendency that the solid-state polymerization reaction does not proceed sufficiently, so that the resultant film is brittle and weak. Meanwhile, if any of the heating temperature and the heating time exceeds the upper limit, coloring, decrease in molecular weight due to thermal decomposition, or the like tends to occur. In addition, an atmosphere during the thermal curing of the dry coating film is preferably an inert gas atmosphere (for example, a nitrogen atmosphere). A pressure condition during the thermal curing is preferably 0.01 to 760 mmHg, and more preferably 0.01 to 200 mmHg. Note that when the method (a) is employed, the heat treatment for the imidization and the subsequent heat treatment for the thermal curing may be conducted at once as a serial heat treatment. In such a case, it is preferable to continuously conduct the heat treatment at a constant temperature by employing a temperature within the temperature range employed for the thermal curing as the heating temperature for the imidization. In other words, when the method (a) is employed, it is possible to obtain the film by the serial heat treatment (the imidization and the thermal curing are conducted in a single heat treatment) in which the coating film is cured directly after the imidization. In addition, when the method in which the reaction liquid obtained in the step (I) is directly applied onto a substrate (for example, a glass plate), and subjected to the drying treatment and the heat treatment is employed as the method (a), a film made of a polyimide can be produced by a simple method.

In addition, the poor solvent of the polyimide used for isolating the above-described polyimide of the present invention in the method (b) is not particularly limited, and methanol, ethanol, isopropanol, acetone, ethyl acetate, hexane, toluene, or the like can be used, for example. In addition, as the solvent of the polyimide solution in the method (b), the same solvents as those described for the solution of a polyamic acid can be used. Moreover, as the method for drying the coating film of the polyimide solution employed in the method (b), the same method as the method for performing the drying treatment on the coating film of the solution of the polyamic acid described above can be employed.

By conducting the method (a) or the method (b) as described above, the film of the polyimide of the present invention can be obtained. The thus obtained film made of the polyimide has a sufficiently high heat resistance and a sufficiently low linear expansion coefficient, and hence has a sufficiently high resistance to heat shock (change in surrounding temperature). As described above, the transparent film made of the polyimide of the present invention has not only a sufficiently high transparency, but also a sufficiently high heat resistance and an extremely low linear expansion coefficient. Hence, occurrence of fractures and cracks in the film can be sufficiently suppressed at a high level, even when the film is exposed to a high temperature during production (for example, a matching process of a solar cell, a display device, or the like). Accordingly, the film made of the polyimide of the present invention is particularly useful as, for example, a substrate film on which a transparent electrode of a touch panel or a solar cell is to be stacked, and a substrate film on which a transparent electrode of a display device (an organic EL display device, a liquid crystal display device, or the like) is to be stacked, as well as a film used in the applications such as FPCs, optical waveguides, image sensors, reflection plates for LEDs, covers for LED illumination, skeleton-type FPCs, coverlay films, chip-on-films, high-ductility composite substrates, liquid crystal orientation films, polyimide coating materials (buffer coating materials for DRAMs, flash memories, next generation LSIs, and the like), resists for semiconductors, lithium ion batteries, and various electrical materials, or the like.

EXAMPLES

Hereinafter, the present invention will be described more specifically based on Examples and Comparative Examples. However, the present invention is not limited to Examples below.

First, methods for evaluating characteristics of compounds, films, and the like obtained in Synthesis Examples, Examples, and Comparative Examples are described.

<Identification of Molecular Structure>

The molecular structures of the compounds obtained in Synthesis Examples, Examples, and the like were identified by measuring IR and NMR spectra with infrared spectrometers (FT/IR-460 and FT/IR-4100 manufactured by JASCO Corporation, and NICOLET380FT-IR manufactured by ThermoFisherScientific K.K.) and NMRspectrometers (trade name: UNITY INOVA-600 manufactured by VARIAN, and JNM-Lambda500 manufactured by JEOL Ltd.).

<HPLC Analysis>

The types of the isomers of the compound obtained in each of Synthesis Examples, Examples, and the like were identified by HPLC measurement. Specifically, HPLC measurement of each compound was conducted by using a measuring apparatus manufactured by Agilent Technologies, Inc. under the trade name of "1200 Series," a column manufactured by Agilent Technologies, Inc. under the trade name of "Eclipse XDB-C18 (5 μm, diameter: 4.6 mm, length: 150 mm)," and a solvent which was a mixture of acetonitrile and distilled water (acetonitrile/distilled water=70 ml/30 ml) as follows. The flow rate of the solvent was set to 1 ml/min, the detection wavelength of a diode array detector (DAD) was set to 210 nm, the temperature was set to 35° C., and samples were prepared by adding 1 mg of each of the compounds to 1.5 ml of the solvent. In addition, the total amount (content ratio: purity) of the trans-endo-endo isomer and the cis-endo-endo isomer in the compound obtained in each of Synthesis Examples, Examples, and the like and the mole ratio of the trans-endo-endo isomer to the cis-endo-endo isomer were determined from the area ratio of HPLC by calculation using a standard curve (the standard samples used are shown in description of Synthesis Examples and Examples). Note that, for 5-norbornene-2-spiro-α-cyclopentanone-α'-spiro-2"-5"-norbornene, the total amount (purity) of the trans-endo-endo isomer and the cis-endo-endo isomer was determined form the ratio of integrated values of $^1$H-NMR.

<Measurement of Glass Transition Temperatures (Tg)>

The glass transition temperatures (Tg) of the compounds obtained in Examples 1 to 4 and Comparative Example 1 were each measured by scanning the range from 30° C. to 440° C. by using a differential scanning calorimeter (manufactured by SII NanoTechnology Inc. under the trade name of "DSC7020"), in which five film-shaped samples with 2 mm in length, 2 mm in width, and 50 μm in thickness were placed in an aluminum sample pan, under conditions of a rate of temperature rise of 10° C./minutes and a rate of temperature drop of 30° C./minutes under a nitrogen atmosphere.

<Measurement of 5% Weight Loss Temperature>

The 5% weight loss temperature of each of the compounds obtained in Examples 1 to 4 and Comparative Example 1 was determined as follows. Specifically, five film-shaped samples with 2 mm in length, 2 mm in width, and 50 μm in thickness were placed in an aluminum sample pan, and a TG/DTA7200 thermogravimetric analyzer (manufactured by SIINanoTechnologyInc.) was used as a measuring apparatus. The samples were heated under a nitrogen gas flow in a range from room temperature (25° C.) to 600° C. under a condition of 10° C./minutes, and the temperature at which the weight of the sample used reached 5% was measured. Thus, the 5% weight loss temperature was determined.

<Measurement of Intrinsic Viscosity [η]>

The intrinsic viscosity [η] of the polyamic acid obtained as an intermediate at the production of a film or the like in each of Examples 1 to 4 and Comparative Example 1 was determined by using an automatic viscometer (trade name: "VMC-252") manufactured by RIGO CO., LTD. as follows. Specifically, a measurement sample of the polyamic acid at a concentration of 0.5 g/dL was prepared by using N,N-dimethylacetamide as a solvent, and measured under a temperature condition of 30° C.

<Measurement of Linear Expansion Coefficients>

The linear expansion coefficients were measured as follows. Specifically, a film having a size of 20 mm in length, 5 mm in width, and 0.05 mm (50 μm) in thickness was formed from each of the polyimides (film-shaped polyimides) obtained in Examples 1 to 4 and Comparative Example 1. Then, the film was dried in a vacuum (120° C., 1 hour (Hr)), and subjected to a heat treatment under a nitrogen atmosphere at 200° C. for 1 hour (Hr). The change in length of each of the thus obtained samples (dry films) was measured from 50° C. to 200° C. by using a thermomechanical analyzer (manufactured by Rigaku Corporation under the trade name of "TMA8310") as a measuring apparatus and by employing conditions of a tensile mode (49 mN) and a rate of temperature rise of 5° C./minutes under a nitrogen atmosphere. Then, the average value of the change in length per 1° C. over the temperature range from 50° C. to 200° C. was determined.

<Measurement of Refractive Indices>

The refractive indices were determined as follows. Specifically, a film-shaped sample with 5 mm in length, 5 mm in width, and 50 μm in thickness was formed from each of the polyimides (film-shaped polyimides) obtained in Examples 1 to 4 and Comparative Example 1. The sample was measured by using a refractive index-measuring apparatus (manufactured by Atago Co., Ltd. under the trade name of "NAR-1T SOLID") as a measuring apparatus under a light source of 589 nm and a temperature condition of 23° C.

<Measurement of Total Luminous Transmittance>

The total luminous transmittance was determined as follows. Specifically, a film-shaped sample with 20 mm in length, 20 mm in width, and 50 μm in thickness was formed from each of the polyimides (film-shaped polyimides) obtained in Examples 1 to 4 and Comparative Example 1. The sample was measured by using a measuring apparatus manufactured by NIPPON DENSHOKU INDUSTRIES CO., LTD. under the trade name of "Haze Meter NDH-5000" according to JIS K7361-1.

Synthesis Example 1

Preparation of 5-Norbornene-2-spiro-α-cyclopentanone-α'-spiro-2"-5"-norbornene

First, to a 2-L three-necked flask, 61.7 g (0.757 mol) of dimethylamine hydrochloride, 182 g (2.46 mol) of 1,3-dioxolane, 25.9 g (0.308 mol) of cyclopentanone, and 4.0 g (38 mmol) of 35% hydrochloric acid were added. Subsequently, a bulb condenser was set to the three-necked flask, and then the atmospheric gas inside the three-necked flask was replaced with nitrogen. After that, the three-necked flask was immersed in an oil bath of 90° C., and heated for 5 hours with stirring. Thus, a reaction liquid was obtained which contained a Mannich base (a compound represented by the general formula (I-2) shown in the above-described reaction formula (1) [a compound of general formula (I-2), where n was 2, $R^2$ and $R^3$ were each a hydrogen atom, Rs was each a methyl group, and $X^-$ was a chlorine ion]). Note that the thus obtained reaction liquid was subjected to a gas chromatography analysis (GC analysis: a detector manufactured by Agilent Technologies under the trade name of "6890N" was used). As a result, it was found that the conversion of cyclopentanone was 99.9% or higher.

Next, the reaction liquid in the three-necked flask was heated to 60° C. While the reaction liquid was kept at this temperature (60° C.), methanol (1000 ml) was added to the reaction liquid to disperse the content. Subsequently, the reaction liquid in which the content was dispersed was cooled to 30° C., and then 4.28 g (47.5 mmol) of a 50% by mass aqueous dimethylamine solution and 61.0 g (1.0 mol) of cyclopentadiene were added to the reaction liquid to obtain a mixture liquid. Subsequently, the atmospheric gas inside the three-necked flask was again replaced with nitrogen, and the three-necked flask was immersed in an oil bath of 80° C. After the mixture liquid was heated for 5 hours, the mixture liquid was cooled to room temperature (25° C.). Next, the mixture liquid was transferred to a 2-L evaporating flask, and then methanol was distilled off by using an evaporator. Subsequently, toluene (200 ml) was added to the residual black viscous liquid, followed by stirring. From the mixture liquid, the toluene layer was recovered to conduct a first extraction operation. Next, toluene (200 ml) was again added to the black viscous liquid remaining after the toluene layer was recovered from the mixture liquid. Then, the toluene layer was recovered to conduct a second extraction operation. Then, the toluene layers obtained by the first and second extraction operations were mixed together to obtain a toluene extraction liquid.

Next, the toluene extraction liquid was washed once with 5% by mass aqueous NaOH (100 ml), and then washed once with 5% by mass aqueous hydrochloric acid (100 ml). Subsequently, the toluene extraction liquid washed with the aqueous hydrochloric acid was washed once with saturated aqueous sodium hydrogen carbonate (100 ml). Subsequently, the thus washed toluene extraction liquid was dehydrated and dried by azeotropic distillation with toluene. Subsequently, the obtained liquid thus dehydrated and dried was filtered and then concentrated using an evaporator to distill off the toluene. Thus, a product (5-norbornene-2-spiro-α-cyclopentanone-α'-spiro-2"-5"-norbornene) was obtained (Yield: 58.9 g, Percentage Yield: 80%).

Figure 3:
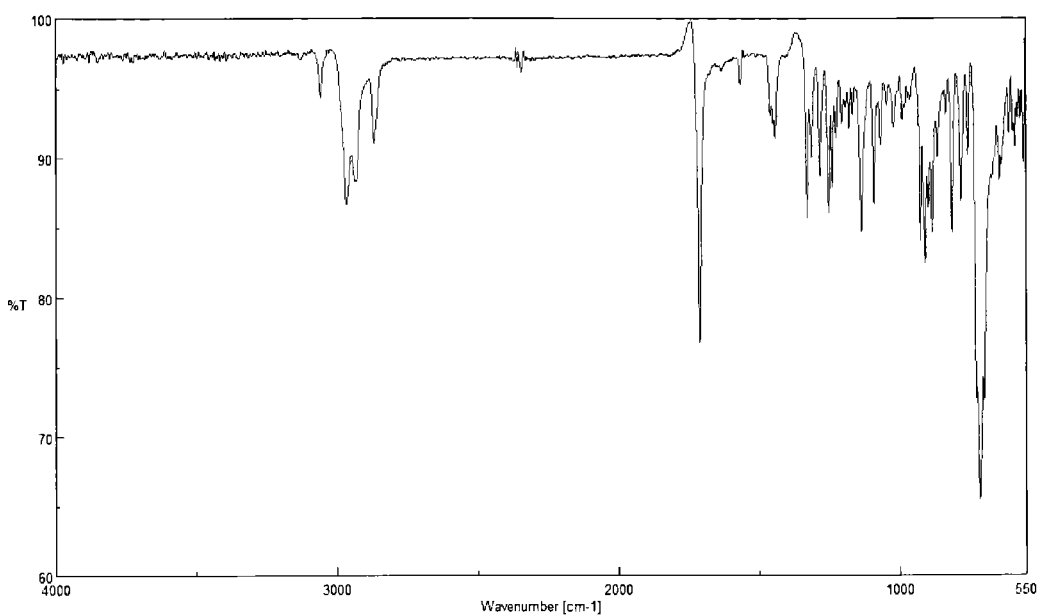
FIG. 3 is a graph showing an IR spectrum of a compound obtained in Synthesis Example 1.
Figure 4:
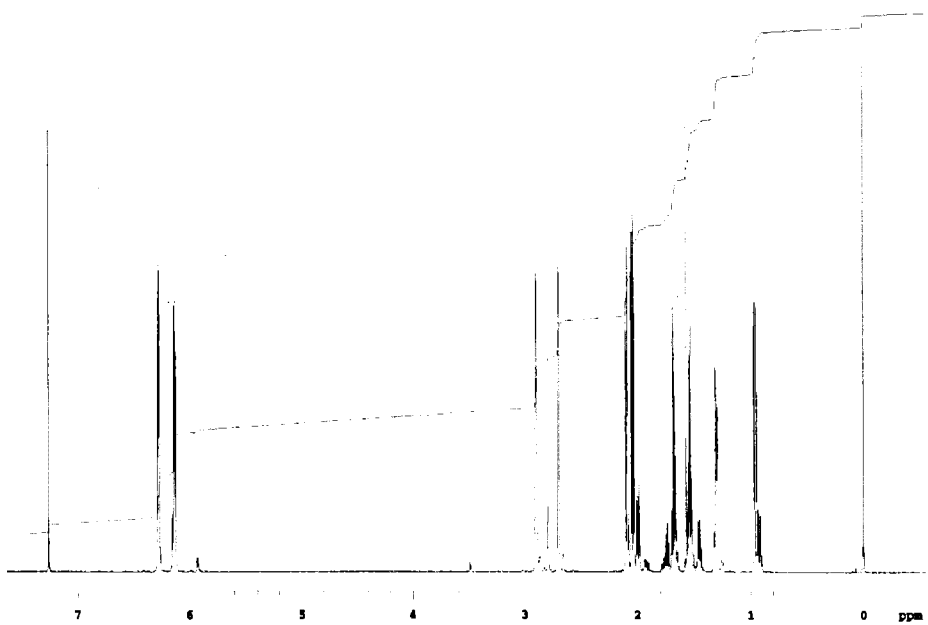
FIG. 4 is a graph showing a $^1$H-NMR (CDCl$_3$) spectrum of the compound obtained in Synthesis Example 1.
Figure 5:
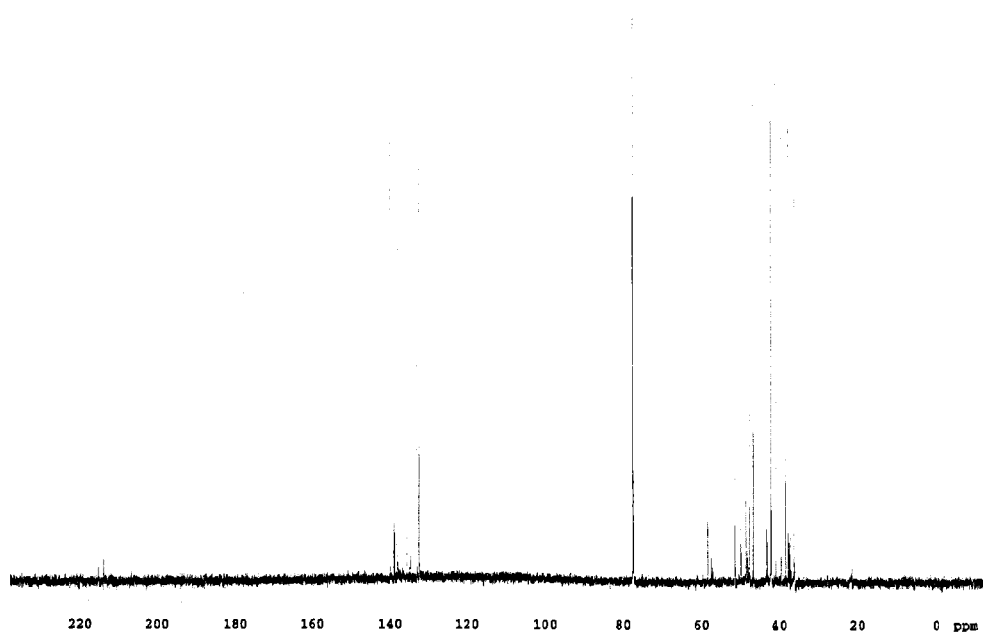
FIG. 5 is a graph showing a $^{13}$C-NMR (CDCl$_3$) spectrum of the compound obtained in Synthesis Example 1.
Figure 6:
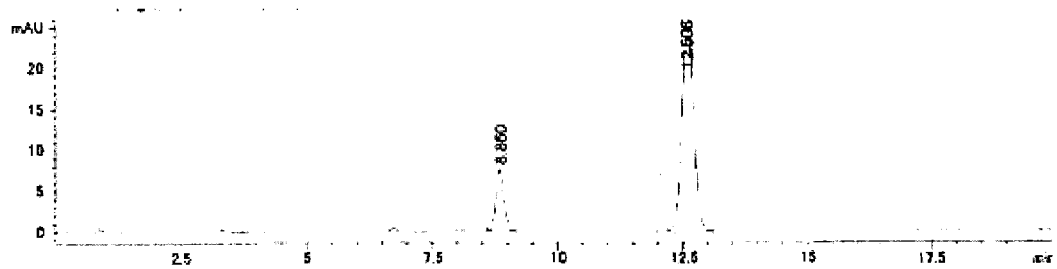
FIG. 6 is a graph showing an HPLC spectrum of the compound obtained in Synthesis Example 1.

To determine the structure of the thus obtained compound, IR measurement, NMR ($^1$H-NMR and $^{13}$C-NMR) measurement, and HPLC measurement were conducted. FIG. 3 shows an IR spectrum of the thus obtained compound, FIG. 4 shows a $^1$H-NMR (CDCl$_3$) spectrum thereof, FIG. 5 shows a $^{13}$C-NMR (CDCl$_3$) spectrum thereof, and FIG. 6 shows an HPLC spectrum thereof. From the results shown in FIGS. 3 to 6, the obtained compound was identified as 5-norbornene-2-spiro-α-cyclopentanone-α'-spiro-2"-5"-norbornene represented by the following general formula (17):

[Chem. 17]

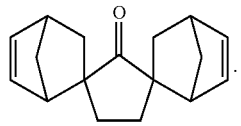

(17)

In addition, from the results shown in FIGS. 3 to 5, it was also found that the 5-norbornene-2-spiro-α-cyclopentanone-α'-spiro-2"-5"-norbornene was a mixture of six isomers on the basis of the number of olefins in $^1$H-NMR. Likewise, also from the result of the HPLC measurement shown in FIG. 6, the 5-norbornene-2-spiro-α-cyclopentanone-α'-spiro-2"-5"-norbornene was found to be a mixture of isomers. Note that, in FIG. 6, the peak at the position of 8.86 minutes on the horizontal axis is attributable to the cis isomers, and the peak at the position of 12.61 minutes is attributable to the trans isomers. Note that, among the six isomers, the content ratio of the trans-endo-endo isomer and the cis-endo-endo isomer was found to be 79% by mole from the results determined on the basis of the ratio of integrated values of $^1$H-NMR.

Synthesis Example 2

Preparation of Norbornane-2-spiro-α-cyclopentanone-α'-spiro-2"-norbornane-5,5",6,6"-tetracarboxylic Acid Tetramethyl Ester To a 1000 ml glass autoclave vessel (manufactured by Taiatsu Techno Corporation under the tradename of "Hyper Glasstor, model TEM-V"), methanol (600 ml), 61.1 g (454 mmol) of CuCl$_2$(II), 26.0 g (108 mmol) of the 5-norbornene-2-spiro-α-cyclopentanone-α'-spiro-2"-5"-norbornene obtained in Synthesis Example 1, and 243 mg (1.08 mmol) of Pd(OAc)$_2$ were added to obtain a mixture liquid. Then, the vessel was hermetically-sealed, and the atmospheric gas inside the vessel was replaced with nitrogen. Next, while carbon monoxide was being introduced into the vessel, the mixture liquid was stirred for 5 hours under conditions of 20° C. and 0.9 MPa to obtain a reaction liquid. Subsequently, carbon monoxide was removed from the inside of the vessel, and the reaction liquid was concentrated using an evaporator to remove methanol from the reaction liquid. Thus, a reaction product was obtained. After that, toluene (900 ml) and 5% by mass hydrochloric acid (900 ml) were added to the reaction product, and the mixture was vigorously stirred under a temperature condition of 80° C. for 1 hour. Thus, a reaction mixture liquid was obtained. Subsequently, the aqueous layer in the reaction mixture liquid was discarded to obtain a toluene extraction liquid, and then the toluene extraction liquid was washed with 5% by mass hydrochloric acid (450 ml) under a temperature condition of 80° C. Subsequently, the toluene extraction liquid thus washed with hydrochloric acid was washed twice with a saturated aqueous sodium hydrogen carbonate solution (450 ml) under a temperature condition of 80° C. Subsequently, the thus obtained toluene extraction liquid was dehydrated and dried by azeotropic distillation with toluene. Next, the obtained liquid dehydrated and dried was filtered and then concentrated using an evaporator to distill off the toluene. Thus, a product (norbornane-2-spiro-α-cyclopentanone-α'-spiro-2"-norbornane-5,5",6,6"-tetracarboxylic acid tetramethyl ester) was obtained (Yield: 49.8 g, Percentage Yield: 95.4%).

Figure 7:
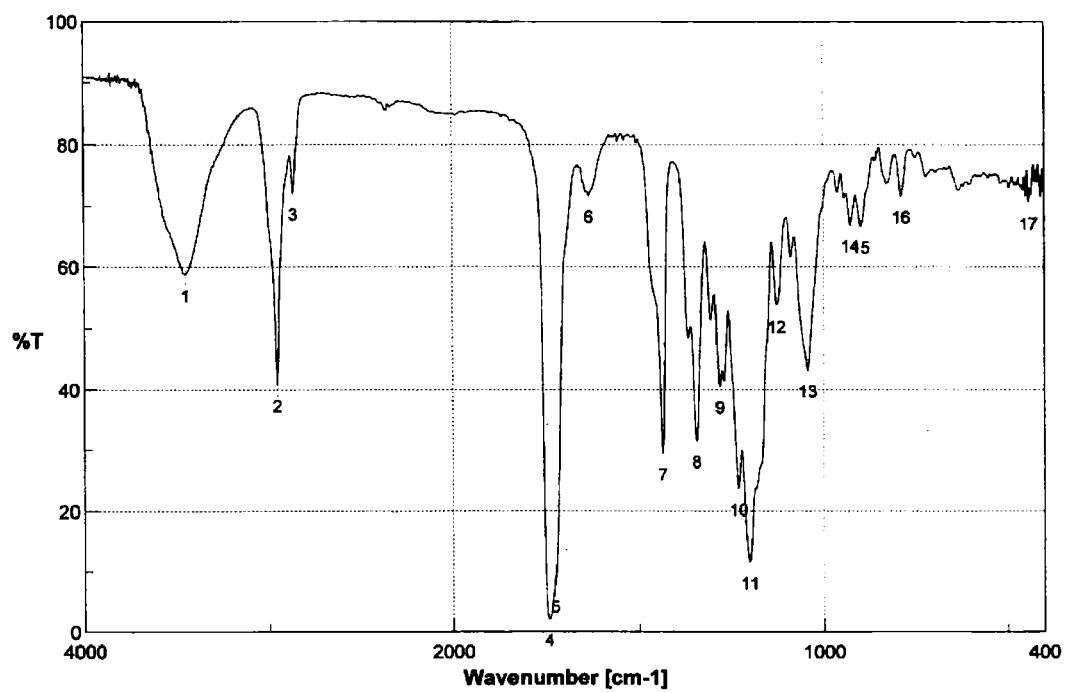
FIG. 7 is a graph showing an IR spectrum of a compound obtained in Synthesis Example 2.
Figure 8:
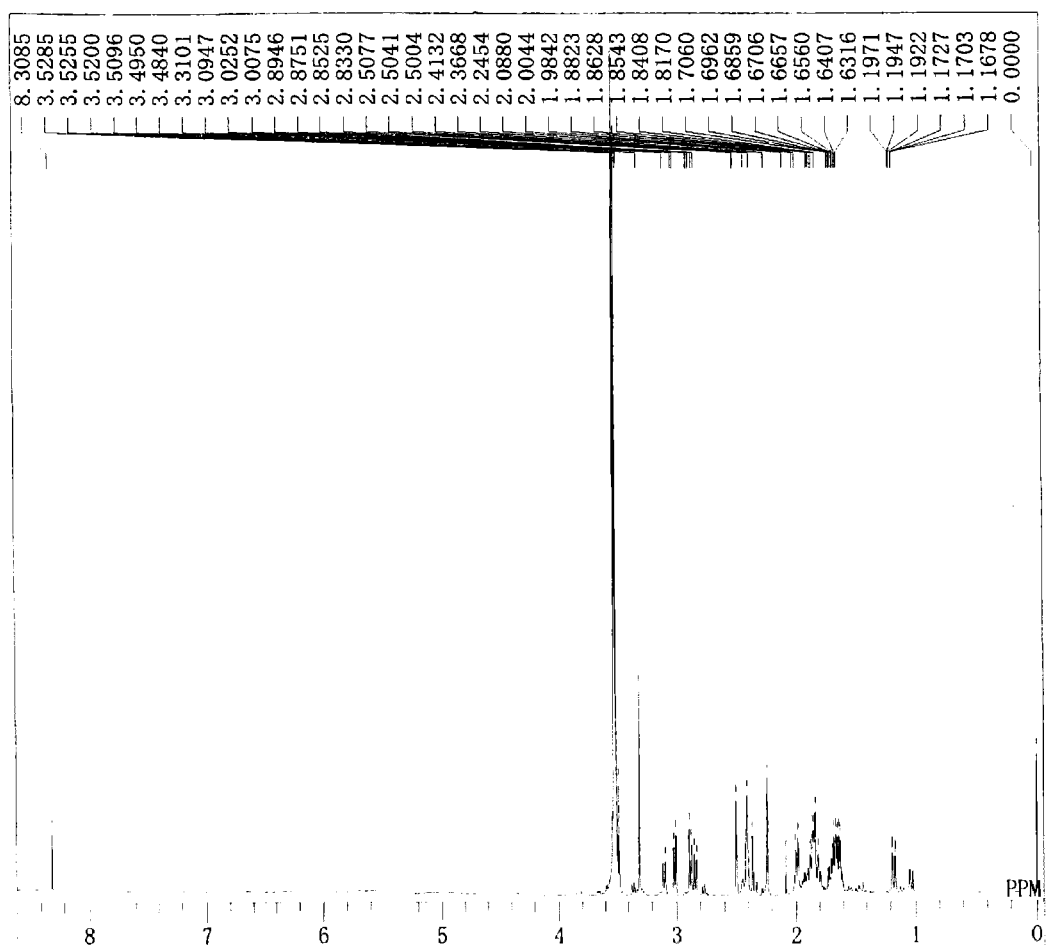
FIG. 8 is a graph showing a $^1$H-NMR (DMSO-d$^6$) spectrum of the compound obtained in Synthesis Example 2.
Figure 9:
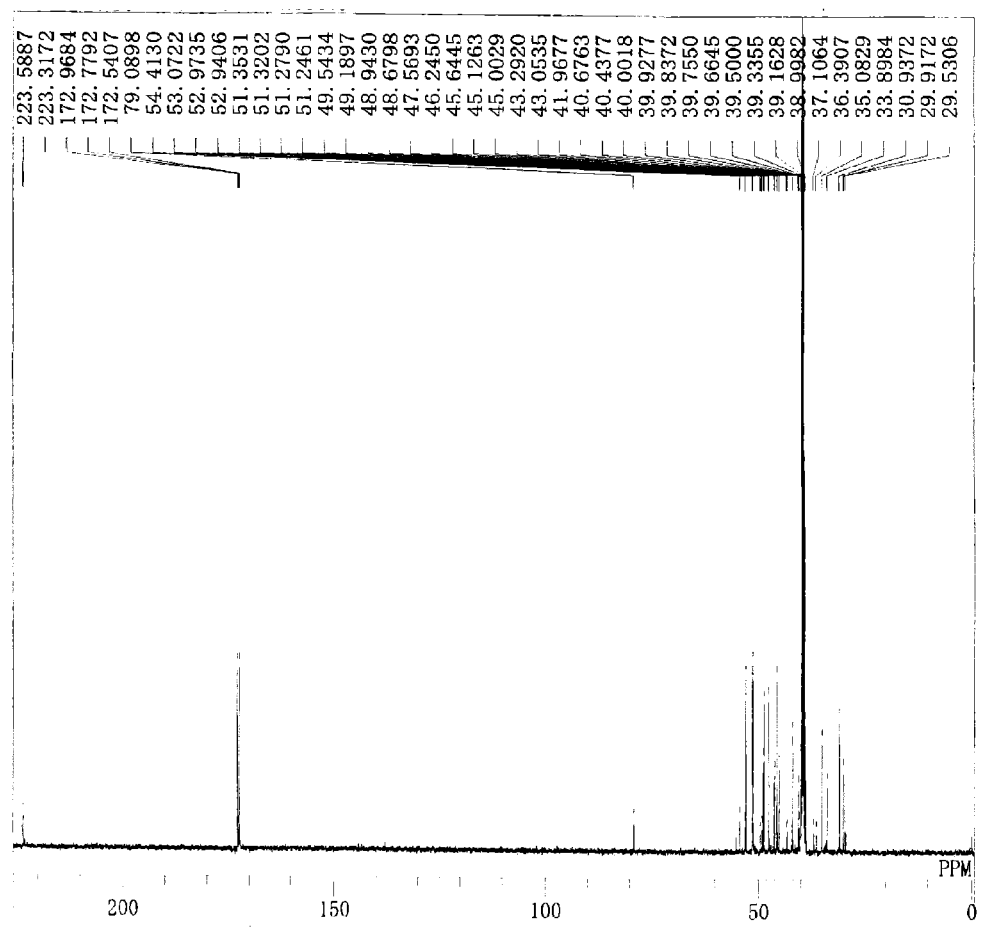
FIG. 9 is a graph showing a $^{13}$C-NMR (DMSO-d$^6$) spectrum of the compound obtained in Synthesis Example 2.
Figure 10:
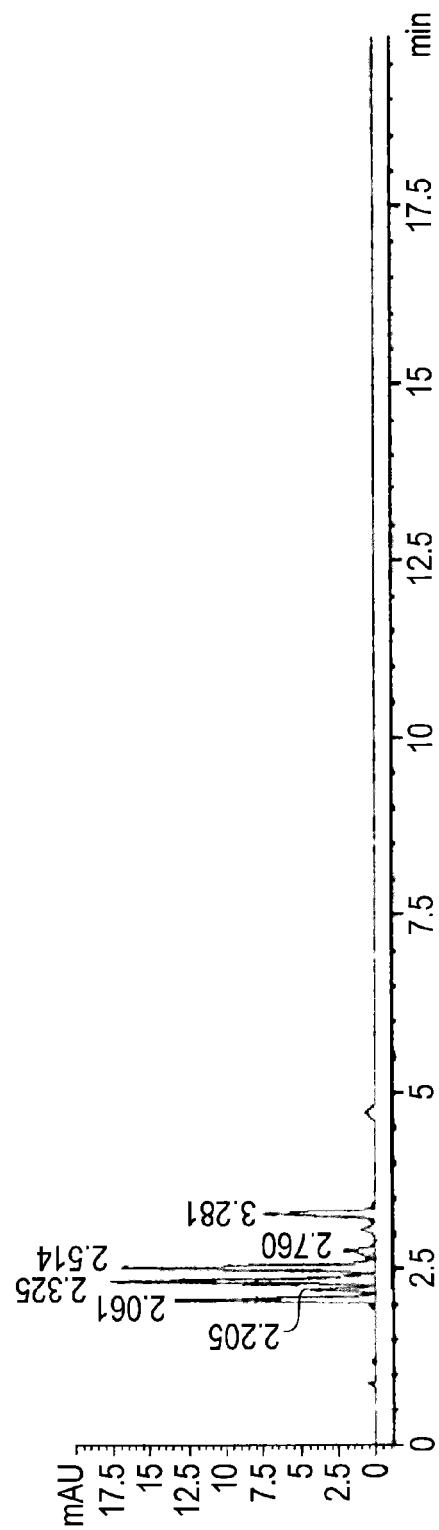
FIG. 10 is a graph showing an HPLC spectrum of the compound obtained in Synthesis Example 2.

To determine the structure of the thus obtained compound, IR measurement, NMR ($^1$H-NMR and $^{13}$C-NMR) measurement, and HPLC measurement were conducted. FIG. 7 shows an IR spectrum of the thus obtained compound, FIG. 8 shows a $^1$H-NMR (DMSO-d$^6$) spectrum thereof, and FIG. 9 shows a $^{13}$C-NMR (DMSO-d$^6$) spectrum thereof. FIG. 10 shows a spectrum of the HPLC measurement. As is apparent from the results shown in FIGS. 7 to 10, the obtained compound was identified as norbornane-2-spiro-α-cyclopentanone-α'-spiro-2"-norbornane-5,5",6,6"-tetracarboxylic acid tetramethyl ester represented by the following general formula (18):

[Chem. 18]

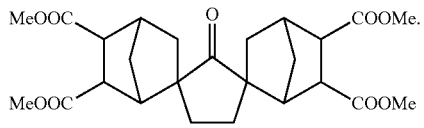

(18)

In addition, as is apparent from the results of the HPLC measurement shown in FIG. 10, the norbornane-2-spiro-α-cyclopentanone-α'-spiro-2"-norbornane-5,5",6,6"-tetracarboxylic acid tetramethyl ester was found to be a mixture of multiple isomers. Note that, in the HPLC shown in FIG. 10, the peak at the position of approximately 3.2 minutes on the horizontal axis is attributable to toluene. Note that, among the multiple isomers, the content ratio of the trans-endo-endo isomer and the cis-endo-endo isomer was found to be 79% by mole from the results determined on the basis of the area ratio in HPLC by using a standard curve (standard sample: dicyclopentadiene).

Synthesis Example 3

Preparation of Norbornane-2-spiro-α-cyclopentanone-α'-spiro-2"-norbornane-5,5",6,6"-tetracarboxylic Dianhydride To a 200 ml three-necked flask equipped with a distillation apparatus, 17.8 g (37.4 mmol) of the norbornane-2-spiro-α-cyclopentanone-α'-spiro-2"-norbornane-5,5",6,6'-tetracarboxylic acid tetramethyl ester obtained in Synthesis Example 2, 113 g (1.88 mol) of acetic acid, and 1.78 g (9.4 mmol) of p-toluenesulfonic acid monohydrate were added to obtain a mixture liquid. Next, the three-necked flask was immersed in an oil bath of 135° C., and the mixture liquid was heated under reflux under an inner temperature condition of 113 to 121° C. for 20 hours (reflux step). Note that, in the reflux step, the reflux was continued, while the produced methyl acetate and water were distilled off with acetic acid. In addition, in the reflux step, the reflux was conducted, while acetic acid was added, as needed, using a dropping funnel to keep the amount of acetic acid in the flask constant. After the reaction was caused to proceed in the mixture liquid by conducting the reflux step, the mixture liquid was allowed to stand at room temperature (25° C.) overnight (for 15 hours) to precipitate a gray solid. Subsequently, after the obtained gray solid was filtered, the obtained gray solid was washed twice with acetic acid (50 ml), and then washed once with toluene (50 ml). The thus washed gray solid was dried by using a vacuum dryer under conditions of 80° C. and 1 mm Hg overnight (for 15 hours) to obtain a crude product (Yield: 13.8 g, Percentage Yield: 96%). Subsequently, the obtained crude product (1.0 g) was placed in a sublimation purification apparatus (manufactured by SIBATA SCIENTIFIC TECHNOLOGY LTD. under the product name of "Glass Tube Oven GTO-350RD equipped with sublimation purification apparatus"), and purified by sublimation at 250 to 290° C./0.1 mmHg for 5 hours to obtain a compound (norbornane-2-spiro-α-cyclopentanone-α'-spiro-2"-norbornane-5,5",6,6"-tetracarboxylic dianhydride) in the form of a white solid (Yield: 0.89 g, Percentage Yield: 89%).

Figure 11:
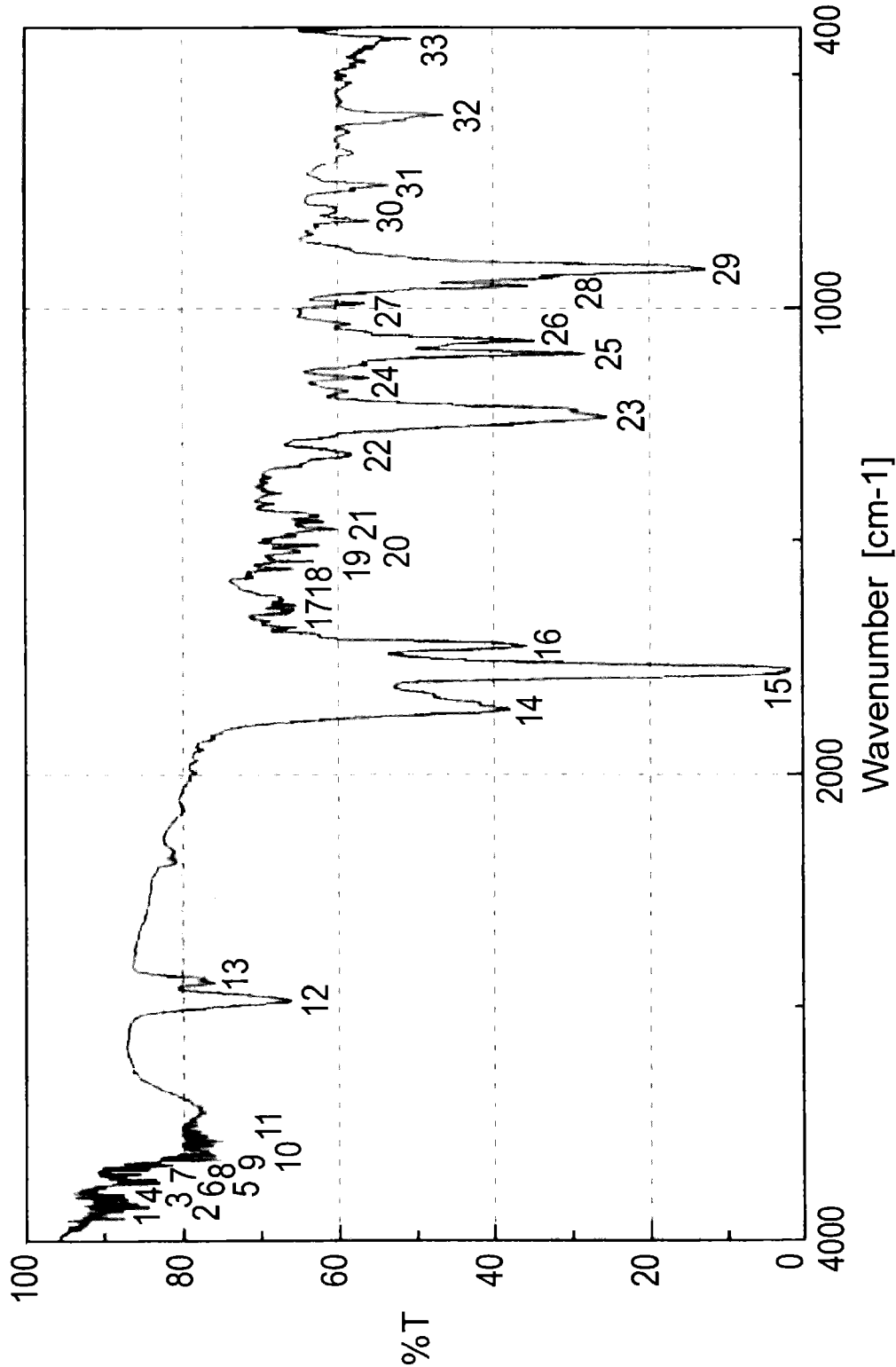
FIG. 11 is a graph showing an IR spectrum of a compound obtained in Synthesis Example 3.
Figure 12:
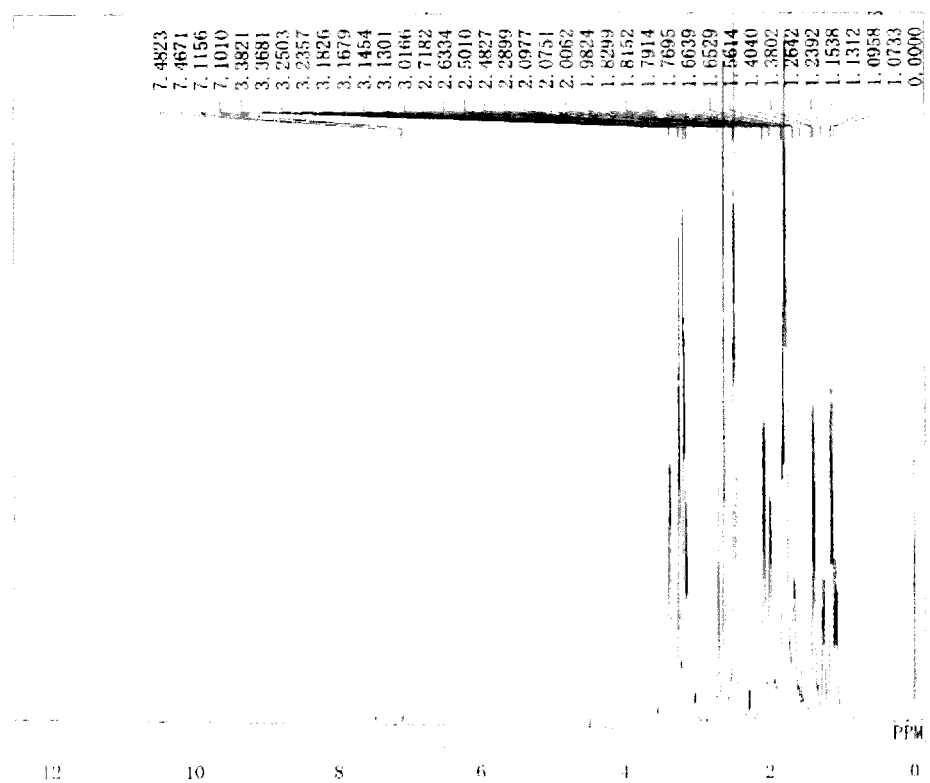
FIG. 12 is a graph showing a $^1$H-NMR (DMSO-d$^6$) spectrum of the compound obtained in Synthesis Example 3.
Figure 13:
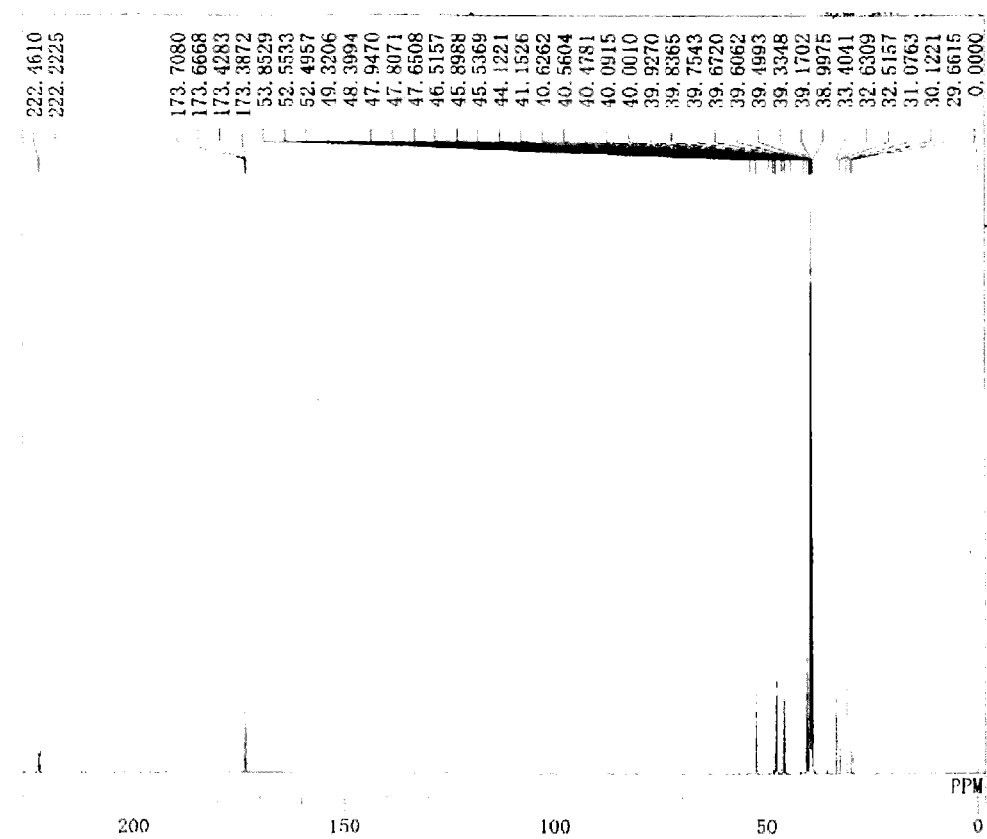
FIG. 13 is a graph showing a $^{13}$C-NMR (DMSO-d$^6$) spectrum of the compound obtained in Synthesis Example 3.
Figure 14:
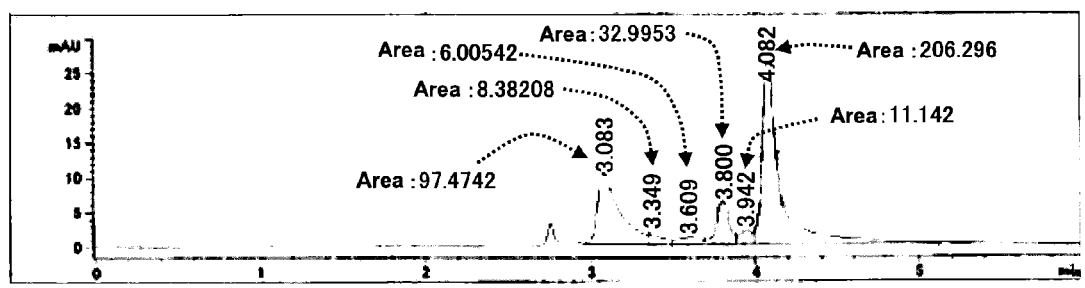
FIG. 14 is a graph showing an HPLC spectrum of the compound obtained in Synthesis Example 3.

To determine the structure of the thus obtained compound, IR measurement, NMR ($^1$H-NMR and $^{13}$C-NMR) measurement, and HPLC measurement were conducted. FIG. 11 shows an IR spectrum of the obtained compound, FIG. 12 shows a $^1$H-NMR (DMSO-d$^6$) spectrum thereof, FIG. 13 shows a $^{13}$C-NMR (DMSO-d$^6$) spectrum thereof, and FIG. 14 shows an HPLC spectrum thereof. As is apparent from the results shown in FIGS. 11 to 14, the obtained compound was identified as norbornane-2-spiro-α-cyclopentanone-α'-spiro-2"-norbornane-5,5",6,6"-tetracarboxylic dianhydride represented by the following general formula (19):

[Chem. 19]

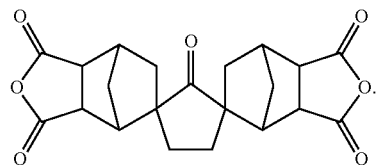

(19)

In addition, as is apparent from the results of the HPLC measurement shown in FIG. 14, the obtained norbornane-2-spiro-α-cyclopentanone-α'-spiro-2"-norbornane-5,5",6,6"-tetracarboxylic dianhydride was found to be a mixture of six isomers, because six peaks (signals) were observed. Note that, among the six isomers, the content ratio of the trans-endo-endo isomer and the cis-endo-endo isomer was found to be 79% by mole from the results determined on the basis of the area ratio in HPLC by using a standard curve (standard sample: naphthalene)

Example 1

Monomer Synthesis Step

To toluene (90 ml), 17.8 g (37.4 mmol) of the norbornane-2-spiro-α-cyclopentanone-α'-spiro-2"-norbornane-5,5",6,6"-tetracarboxylic acid tetramethyl ester obtained in Synthesis Example 2 was added, and then dissolved by heating to 110° C. to obtain a toluene solution. Subsequently, the toluene solution was cooled to room temperature (25° C.) at a rate of temperature drop of 2° C./minutes, and allowed to stand overnight (for 15 hours) to separate white crystals (crystals of the trans-endo-endo isomer and the cis-endo-endo isomer of the norbornane-2-spiro-α-cyclopentanone-α'-spiro-2"-norbornane-5,5",6,6"-tetracarboxylic acid tetramethyl ester obtained in Synthesis Example 2) (recrystallization method). Next, the thus obtained white crystals were filtered and dried in a vacuum to obtain a first compound (white crystals) (Yield: 8.9 g, Percentage Yield: 50%).

Figure 15:
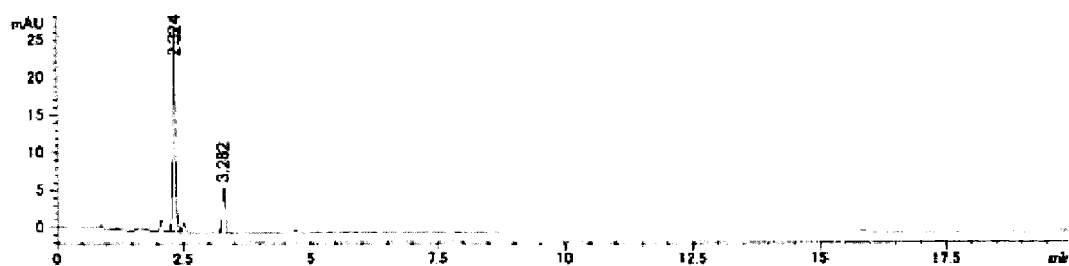
FIG. 15 is a graph showing an HPLC spectrum of a first compound obtained in a monomer synthesis step employed in Example 1.
Figure 16:
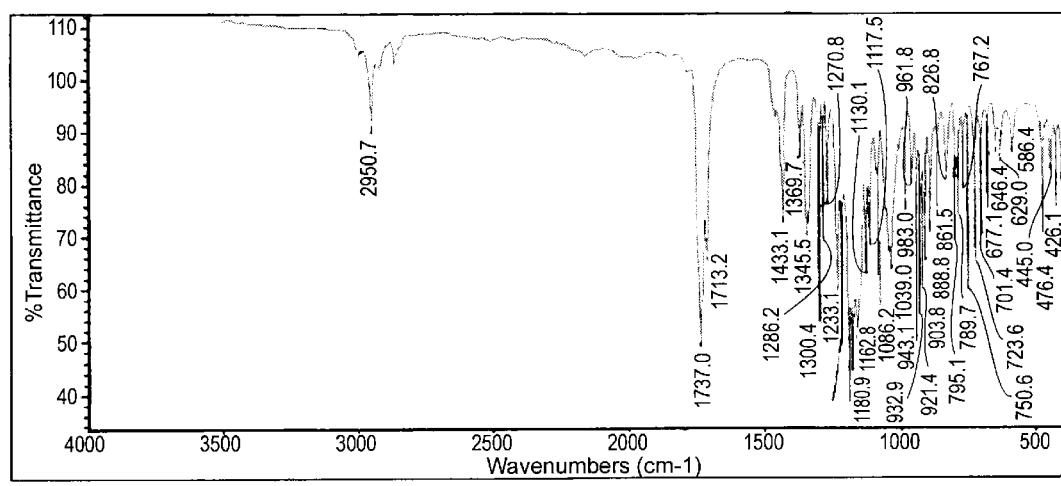
FIG. 16 is a graph showing an IR spectrum of the first compound obtained in the monomer synthesis step employed in Example 1.
Figure 17:
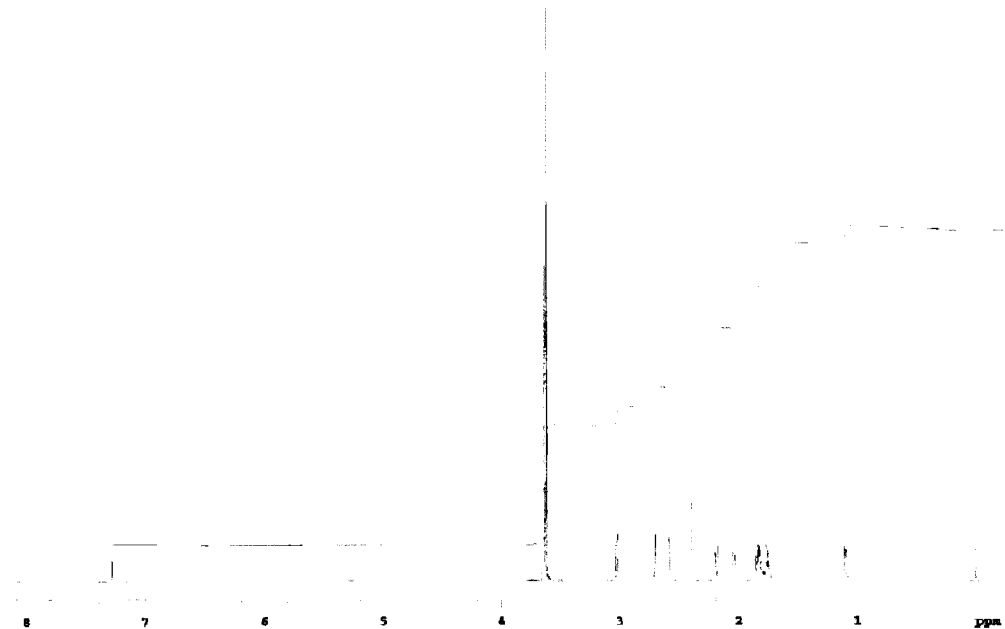
FIG. 17 is a graph showing a $^1$H-NMR (DMSO-d$^6$) spectrum of the first compound obtained in the monomer synthesis step employed in Example 1.
Figure 18:
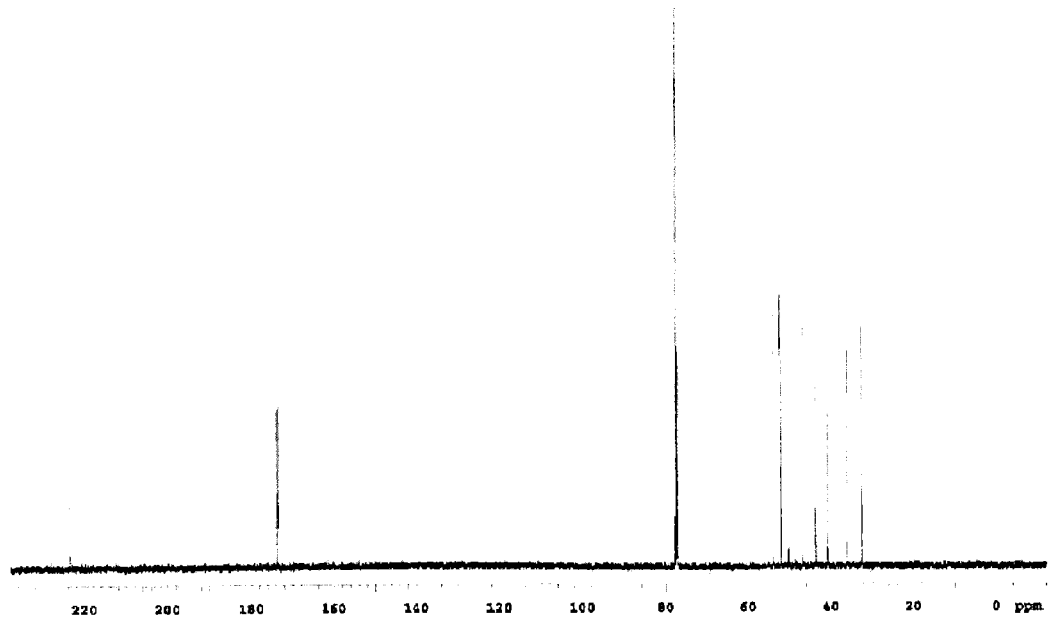
FIG. 18 is a graph showing a $^{13}$C-NMR (DMSO-d$^6$) spectrum of the first compound obtained in the monomer synthesis step employed in Example 1.

The thus obtained first compound (white crystals) was subjected to HPLC measurement. FIG. 15 shows the obtained results. In the result of the HPLC measurement shown in FIG. 15, one peak (signal) was observed, indicating that some specific isomers were selectively separated by the above-described recrystallization method. Subsequently, to determine the structure of the obtained first compound (white crystals), IR measurement and NMR ($^1$H-NMR and $^{13}$C-NMR) measurement were conducted. FIG. 16 shows an IR spectrum of the obtained first compound, FIG. 17 shows a $^1$H-NMR (DMSO-d$^6$) spectrum thereof, and FIG. 18 shows a $^{13}$C-NMR (DMSO-d$^6$) spectrum thereof. As is apparent from the results shown in FIGS. 16 to 18, it was found that two isomers (the trans-endo-endo isomer and the cis-endo-endo isomer in the norbornane-2-spiro-α-cyclopentanone-α'-spiro-2"-norbornane-5,5",6,6"-tetracarboxylic acid tetramethyl ester obtained in Synthesis Example 2) were selectively separated by the recrystallization method. Note that the content ratio (the total amount) of the trans-endo-endo isomer and the cis-endo-endo isomer in the first compound was found to be 99% by mole from the results determined on the basis of the area ratio in HPLC by using a standard curve (standard sample: dicyclopentadiene).

Subsequently, the first compound was converted to an acid dianhydride to obtain a crude product (Yield: 6.9 g, Percentage Yield: 96%) by employing the same method as that employed in Synthesis Example 3, except that the first compound (specific isomers: 8.9 g) was used instead of the norbornane-2-spiro-α-cyclopentanone-α'-spiro-2"-norbornane-5,5",6,6"-tetracarboxylic acid tetramethyl ester obtained in Synthesis Example 2. Subsequently, the obtained crude product (1.0 g) was placed in a sublimation purification apparatus (manufactured by SIBATA SCIENTIFIC TECHNOLOGY LTD. under the product name of "Glass Tube Oven GTO-350RD equipped with sublimation purification apparatus"), and purified by sublimation at 250 to 290° C./0.1 mmHg for 5 hours to obtain a second compound in the form of a white solid (Yield: 0.90 g, Percentage Yield: 90%).

Figure 19:
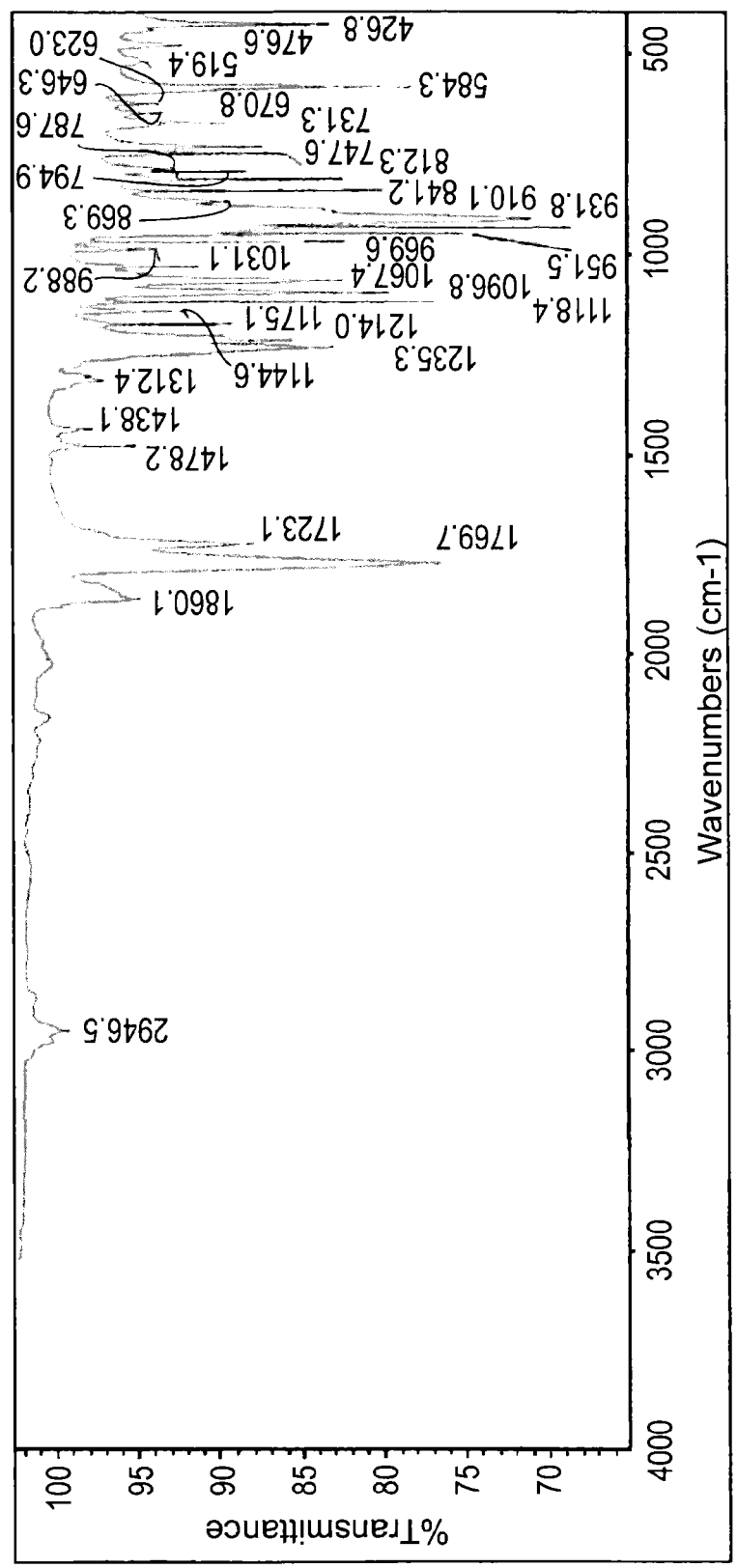
FIG. 19 is a graph showing an IR spectrum of a second compound obtained in the monomer synthesis step employed in Example 1.
Figure 20:
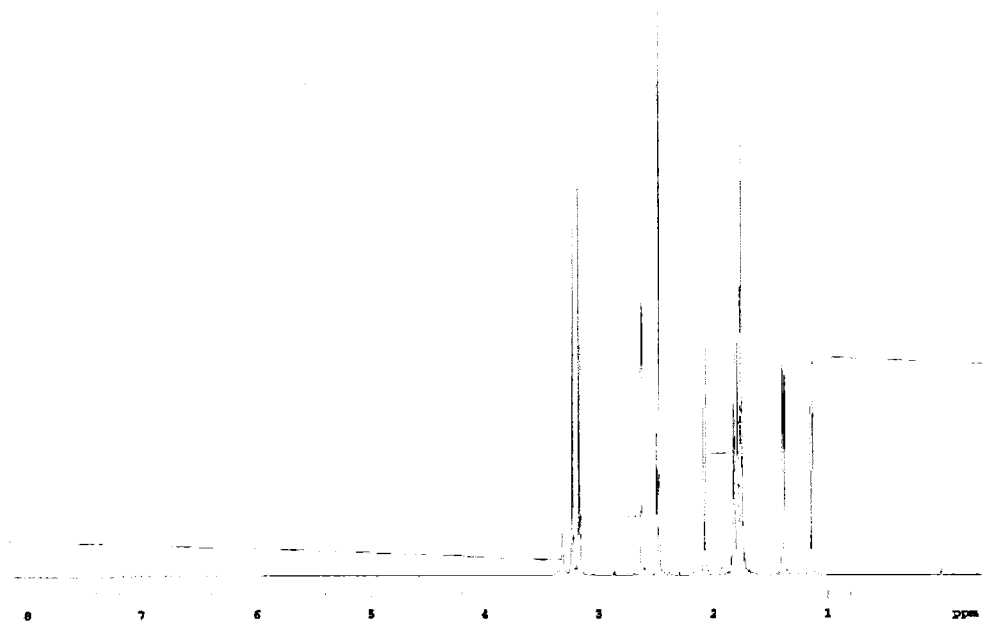
FIG. 20 is a graph showing a $^1$H-NMR (DMSO-d$^6$) spectrum of the second compound obtained in the monomer synthesis step employed in Example 1.
Figure 21:
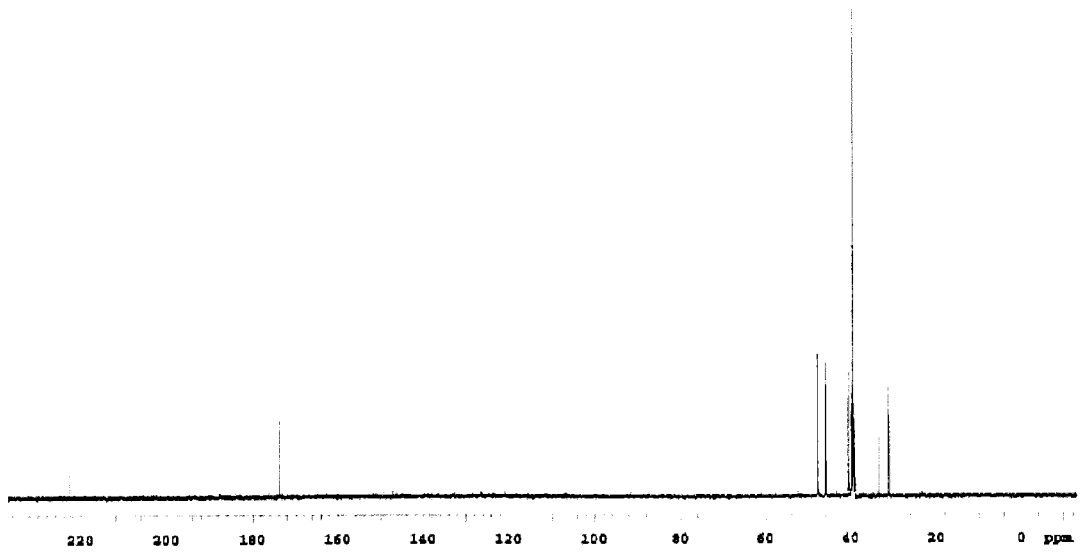
FIG. 21 is a graph showing a $^{13}$C-NMR (DMSO-d$^6$) spectrum of the second compound obtained in the monomer synthesis step employed in Example 1.
Figure 22:
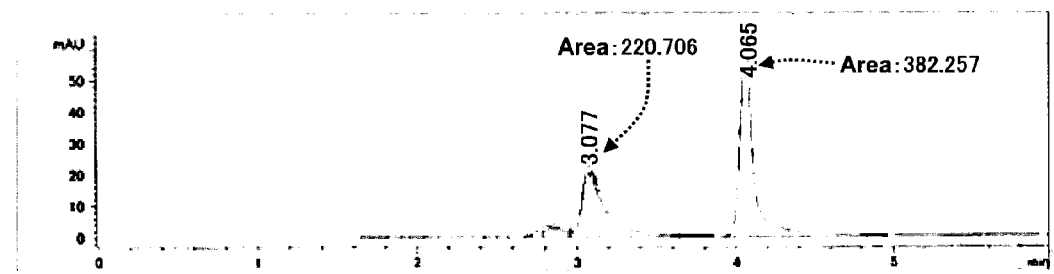
FIG. 22 is a graph showing an HPLC spectrum of the second compound obtained in the monomer synthesis step employed in Example 1.

To determine the structure of the thus obtained second compound, IR measurement, NMR ($^1$H-NMR and $^{13}$C-NMR) measurement, and HPLC measurement were conducted. FIG. 19 shows an IR spectrum of the obtained second compound, FIG. 20 shows a $^1$H-NMR (DMSO-d$^6$) spectrum thereof, FIG. 21 shows a $^{13}$C-NMR (DMSO-d$^6$) spectrum thereof, and FIG. 22 shows an HPLC spectrum thereof. From the results of the HPLC measurement, the second compound was found to be a mixture of two isomers. In addition, as is apparent from the results shown in FIGS. 19 to 22, the obtained second compound was identified as a mixture of trans-endo-endo-norbornane-2-spiro-α-cyclopentanone-α'-spiro-2''-norbornane-5,5'',6,6''-tetracarboxylic dianhydride represented by the following general formula (20):

[Chem. 20]

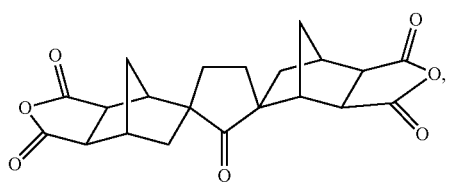

(20)

and cis-endo-endo-norbornane-2-spiro-α-cyclopentanone-α'-spiro-2''-norbornane-5,5'',6,6''-tetracarboxylic dianhydride represented by the following general formula (21):

[Chem. 21]

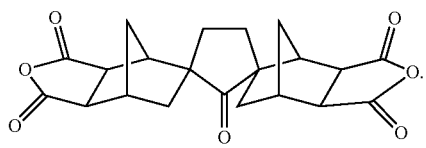

(21)

Note that the content ratio (the total amount) of the compounds represented by the general formulae (20) and (21) in the obtained second compound was found to be 99% by mole from the results determined on the basis of the area ratio in HPLC by using a standard curve (standard sample: naphthalene), and the mole ratio ([formula (20)]:[formula (21)]) of the compound represented by the general formula (20) to the compound represented by the general formula (21) was found to be 63:37 from the results determined on the basis of the area ratio in HPLC by using the standard curve (standard sample: naphthalene)<

<Polyimide Preparation Step>

First, a 30-ml three-necked flask was sufficiently dried by heating with a heat gun. Next, the atmospheric gas in the sufficiently dried three-necked flask was replaced with nitrogen to create a nitrogen atmosphere in the three-necked flask. Subsequently, 0.2045 g (0.90 mmol) of 4,4'-diaminobenzanilide (DABAN manufactured by Tokyo Chemical Industry Co., Ltd.) was added into the three-necked flask, and then 2.7 g of N,N-dimethylacetamide was further added, followed by stirring. Thus, the aromatic diamine compound (4,4'-diaminobenzanilide (DABAN)) was dissolved in N,N-dimethylacetamide to obtain a solution (DABAN was partially dissolved).

Next, to the three-necked flask containing the solution, 0.3459 g (0.90 mmol) of the second compound (the mixture of the compound represented by the general formula (20) and the compound represented by the general formula (21)) obtained in the monomer synthesis step was added under a nitrogen atmosphere, and then the mixture was stirred under a nitrogen atmosphere at room temperature (25° C.) for 12 hours to obtain a reaction liquid. Thus, a polyamic acid was formed in the reaction liquid. Note that, by using a portion of the reaction liquid (a solution of the polyamic acid in dimethylacetamide), a dimethylacetamide solution having a polyamic acid concentration of 0.5 g/dL was prepared, and the intrinsic viscosity [η] of the polyamic acid, which was a reaction intermediate, was measured. The intrinsic viscosity [η] of the polyamic acid was 0.93.

Subsequently, the reaction liquid obtained as described above was cast on a glass plate (Length: 200 mm, Width: 200 mm), so that the coating film had a thickness of 50 μm after being thermally cured. Thus, a coating film was formed on the glass plate. After that, the glass plate on which the coating film was formed was introduced into a vacuum oven, and the coating film was cured by heating under a pressure of 100 mmHg and under a temperature condition of 40° C. for 12 hours, and then further under a pressure of 1 mmHg and under a temperature condition of 400° C. for 1 hour. Thus, a film made of a polyimide was formed on the glass plate. Subsequently, the glass plate on which the film made of the polyimide was formed was taken out of the vacuum oven. The film made of the polyimide was recovered from the glass plate by immersing the glass plate into water of 25° C. for 12 hours, and edge portions of the film were cut off. Thus, a colorless transparent film (100 mm in length, 100 mm in width, and 50 μm in thickness) made of the polyimide was obtained.

Figure 23:
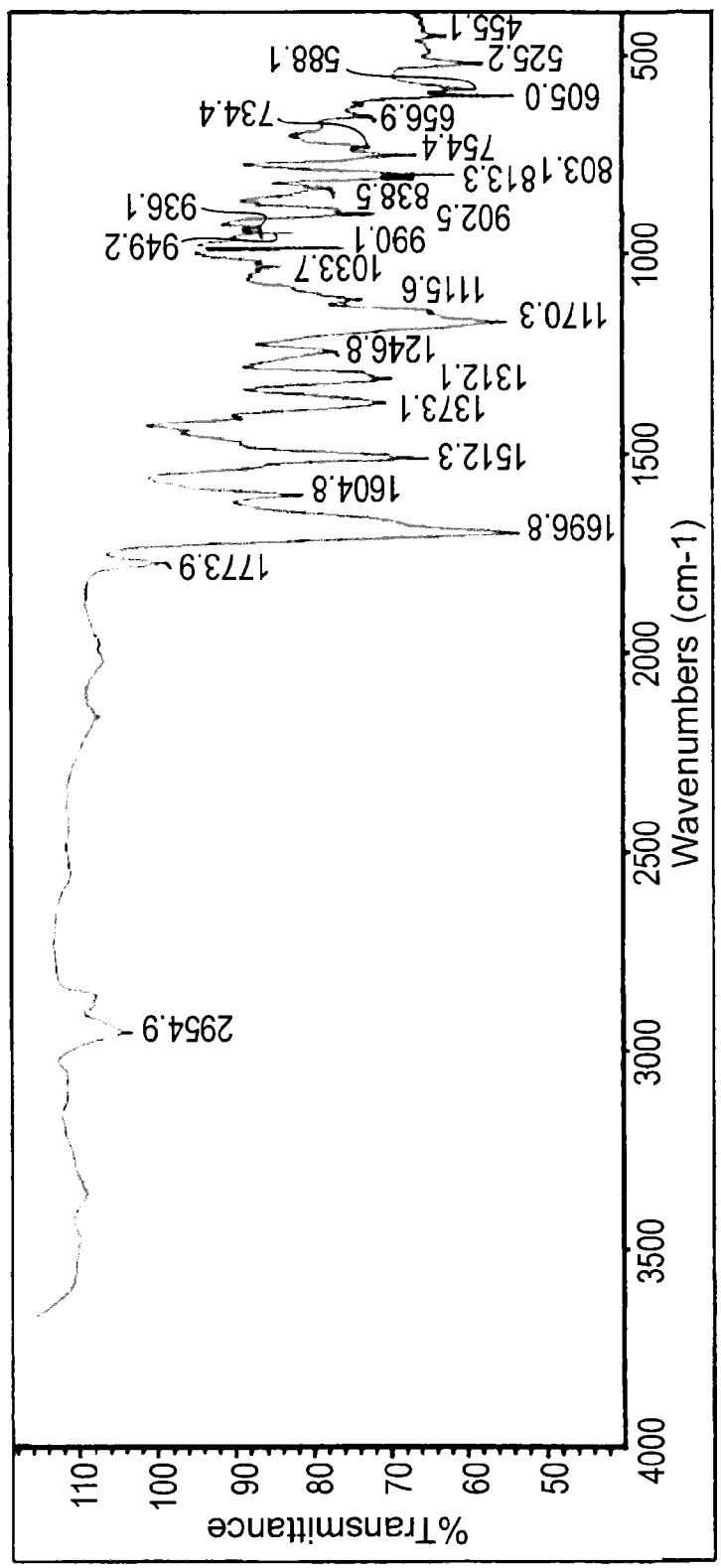
FIG. 23 is a graph showing an IR spectrum of a compound (polyimide) obtained in a polyimide preparation step employed in Example 1.

An IR spectrum of the compound constituting the thus obtained film was measured. FIG. 23 shows the IR spectrum of the obtained compound. As is apparent from the results shown in FIG. 23, C═O stretching vibration of imidocarbonyl was observed at 1696.8 cm$^{-1}$ for the obtained compound, and the obtained compound was confirmed to be a polyimide. In addition, it was found that the polyimide forming the obtained film was a polyimide comprising the repeating units represented by the general formulae (1) and (2) in an amount of 99% by mole relative to all the repeating units on the basis of the kinds of the monomer used (the second compound (the mixture of the compound represented by the general formula (20) and the compound represented by the general formula (21)) and the aromatic diamine compound (4,4'-diaminobenzanilide)), and the measurement results of the IR spectrum. Moreover, the characteristics of the polyimide were evaluated by using the thus obtained film made of the polyimide in the same manner as described above. The results showed that the polyimide had a linear expansion coefficient of 10 ppm/° C., a glass transition temperature of 371° C., and a 5% weight loss temperature of 482° C. Table 1 shows the obtained results.

Example 2

Monomer Synthesis Step

To toluene (90 ml), the norbornane-2-spiro-α-cyclopentanone-α'-spiro-2''-norbornane-5,5'',6,6''-tetracarboxylic acid tetramethyl ester (17.8 g, 37.4 mmol) obtained in Synthesis Example 2 was added, and then dissolved by heating to 110° C. to obtain a toluene solution. Subsequently, the toluene solution was cooled to room temperature (25° C.) to precipitate a solid content in the toluene solution. Then, the liquid was filtered by using Celite (Celite: Standard Super Cell manufactured by Wako Pure Chemical Industries, Ltd.) to separated the solid content by filtration (filtration step: adsorptive separation method). Subsequently, the Celite after the filtration step was washed with toluene under a condition of room temperature (25° C.), and then Soxhlet extraction using toluene as the solvent was conducted by using a Soxhlet extractor and the recovered Celite to obtain white crystals. Next, the thus obtained white crystals were filtered and dried in a vacuum to obtain a third compound (white crystals) (Yield: 7.8 g, Percentage Yield: 44%).

The thus obtained third compound (white crystals) was subjected to HPLC measurement. In the obtained HPLC spectrum, a single peak (signal) was observed as in the case of Example 1, indicating that specific isomers were selectively separated by the adsorptive separation method. Subsequently, to determine the structure of the obtained third compound (white crystals), IR measurement and NMR ($^1$H-NMR and $^{13}$C-NMR) measurement were conducted. In each of the graphs of the spectra obtained by the IR measurement and the NMR ($^1$H-NMR and $^{13}$C-NMR) measurement, peaks (signals) were present at the same positions as those in Example 1. From these measurement results, it has been found that specific isomers can be selectively separated by the adsorptive separation method. In addition, from the measurement results, it was found that two isomers (the trans-endo-endo isomer and the cis-endo-endo isomer in the norbornane-2-spiro-α-cyclopentanone-α'-spiro-2"-norbornane-5,5",6,6"-tetracarboxylic acid tetramethyl ester obtained in Synthesis Example 2) were selectively separated by the adsorptive separation method. Note that the content ratio (the total amount) of the trans-endo-endo isomer and the cis-endo-endo isomer in the third compound was found to be 99% by mole from the results determined on the basis of the area ratio in HPLC by using a standard curve (standard sample: dicyclopentadiene).

Subsequently, the third compound was converted to an acid dianhydride to obtain a crude product (Yield: 6.0 g, Percentage Yield: 96%) by employing the same method as that employed in Synthesis Example 3, except that the third compound (specific isomers: 7.8 g) was used instead of the norbornane-2-spiro-α-cyclopentanone-α'-spiro-2"-norbornane-5,5",6,6"-tetracarboxylic acid tetramethyl ester obtained in Synthesis Example 2. Subsequently, the obtained crude product (1.0 g) was placed in a sublimation purification apparatus (manufactured by SIBATA SCIENTIFIC TECHNOLOGY LTD. under the product name of "Glass Tube Oven GTO-350RD equipped with sublimation purification apparatus"), and purified by sublimation at 250 to 290° C./0.1 mmHg for 5 hours. Thus, a fourth compound was obtained in the form of a white solid (Yield: 0.89 g, Percentage Yield: 89%).

To determine the structure of the thus obtained fourth compound, IR measurement, NMR ($^1$H-NMR and $^{13}$C-NMR) measurement, and HPLC measurement were conducted. Spectra having peaks at the same positions as those in Example 1 were obtained. From these measurement results, the obtained fourth compound was found to be a mixture of the compound represented by the general formula (20) and the compound represented by the general formula (21) (a mixture of trans-endo-endo- and cis-endo-endo-norbornane-2-spiro-α-cyclopentanone-α'-spiro-2"-norbornane-5,5",6,6"-tetracarboxylic dianhydrides). Note that the content ratio (the total amount) of the compounds represented by the general formulae (20) and (21) in the obtained fourth compound was found to be 99% by mole from the results determined on the basis of the area ratio in HPLC by using a standard curve (standard sample: naphthalene), and the mole ratio ([formula (20)]:[formula (21)]) of the compound represented by the general formula (20) to the compound represented by the general formula (21) was found to be 64:36 from the results determined on the basis of the area ratio in HPLC by using a standard curve (standard sample: naphthalene).

<Polyimide Preparation Step>

A colorless transparent film made of a polyimide (100 mm in length, 100 mm in width, and 50 μm in thickness) was obtained by employing the same method as that in the polyimide preparation step employed in Example 1, except that the fourth compound obtained in the monomer synthesis step was used instead of the second compound. Note that the intrinsic viscosity [η] of a polyamic acid which was a reaction intermediate obtained in conducting the polyimide preparation step was 0.94.

Figure 24:
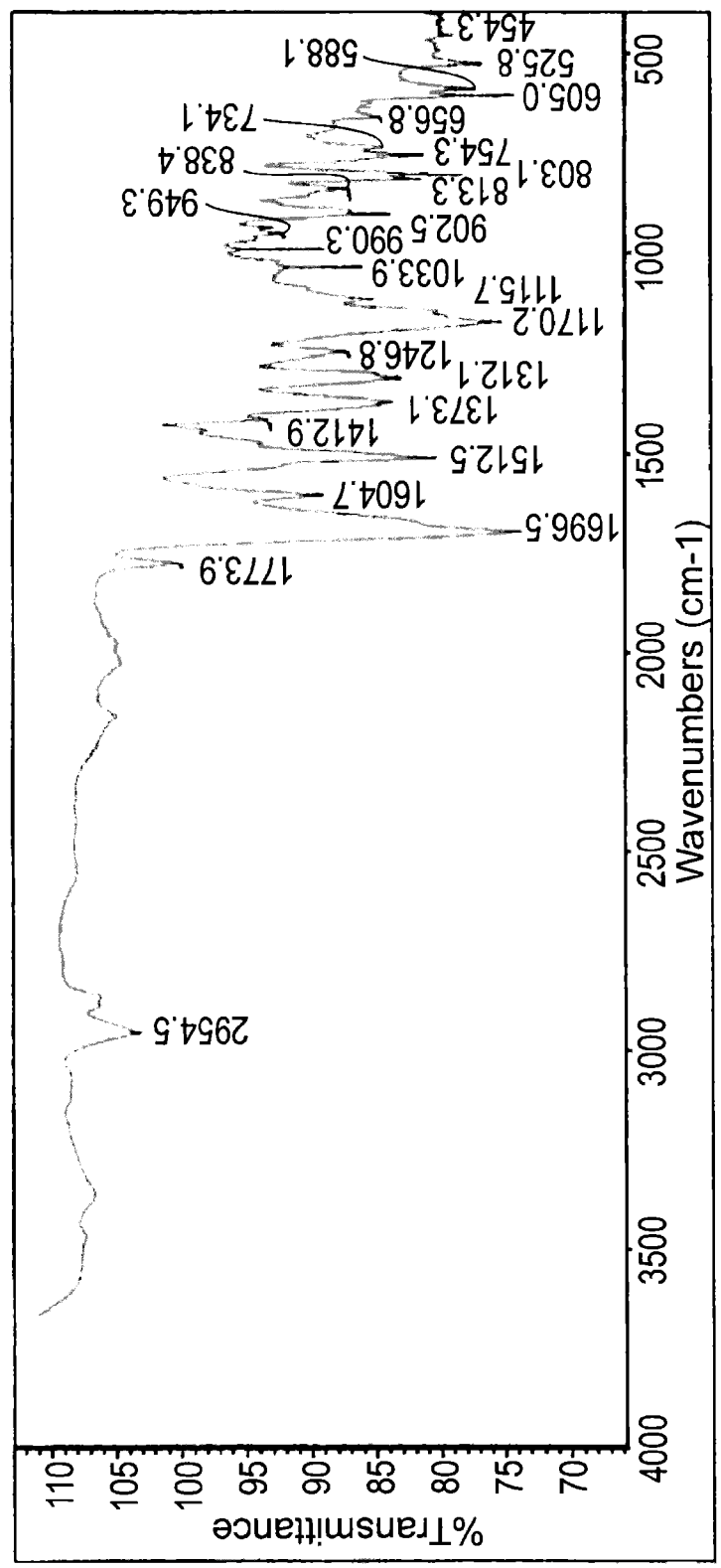
FIG. 24 is a graph showing an IR spectrum of a compound (polyimide) obtained in a polyimide preparation step employed in Example 2.

An IR spectrum of the compound constituting the thus obtained film was measured. FIG. 24 shows the IR spectrum of the obtained compound. As is apparent from the results shown in FIG. 24, C=O stretching vibration of imidocarbonyl was observed at 1696.5 cm$^{-1}$ for the obtained compound, and the obtained compound was confirmed to be a polyimide. In addition, the polyimide forming the obtained film was found to be a polyimide comprising the repeating units represented by the general formulae (1) and (2) in an amount of 99% by mole relative to all the repeating units, on the basis of the kinds of the monomer used (the fourth compound (the mixture of the compound represented by the general formula (20) and the compound represented by the general formula (21)) and the aromatic diamine compound (4,4'-diaminobenzanilide)), and the measurement results of the IR spectrum. Moreover, the characteristics of the polyimide were evaluated by using the thus obtained film made of the polyimide in the same manner as described above. The results showed that the polyimide had a linear expansion coefficient of 9 ppm/° C., a glass transition temperature of 372° C., and a 5% weight loss temperature of 483° C. Table 1 shows the obtained results.

Example 3

Monomer Preparation Step

A fifth compound in which the content ratio (the total amount) of the compounds represented by the general formulae (20) and (21) was 95% by mole was prepared by mixing (blending) the second compound obtained in Example 1 (0.39 g, content ratio in fifth compound: 78% by mass) and the norbornane-2-spiro-α-cyclopentanone-α'-spiro-2'-norbornane-5,5",6,6"-tetracarboxylic dianhydride obtained in Synthesis Example 3 (0.11 g, content ratio in fifth compound: 22% by mass).

<Polyimide Preparation Step>

A colorless transparent film made of a polyimide (100 mm in length, 100 mm in width, and 50 μm in thickness) was obtained by employing the same method as that in the polyimide preparation step employed in Example 1, except that the fifth compound obtained in the monomer preparation step was used instead of the second compound. The characteristics of the polyimide were evaluated by using the thus obtained film made of the polyimide in the same manner as described above. The results showed that the polyimide had a linear expansion coefficient of 12 ppm/° C., a glass transition temperature of 370° C., and a 5% weight loss temperature of 482° C. Table 1 shows the obtained results.

Example 4

Monomer Preparation Step

A sixth compound in which the content ratio (the total amount) of the compounds represented by the general formulae (20) and (21) was 90% by mole was prepared by mixing (blending) the second compound obtained in Example 1 (0.28 g, content ratio in sixth compound: 56% by mass) and the norbornane-2-spiro-α-cyclopentanone-α'-spiro-2'-norbornane-5,5",6,6'-tetracarboxylic dianhydride obtained in Synthesis Example 3 (0.22 g, content ratio in sixth compound: 44% by mass).

<Polyimide Preparation Step>

A colorless transparent film made of a polyimide (100 mm in length, 100 mm in width, and 50 μm in thickness) was obtained by employing the same method as that in the polyimide preparation step employed in Example 1, except that the sixth compound obtained in the monomer preparation step was used instead of the second compound. The characteristics of the polyimide were evaluated by using the thus obtained film made of the polyimide in the same manner as described above. The results showed that the polyimide had a linear expansion coefficient of 14 ppm/° C., a glass transition temperature of 370° C., and a 5% weight loss temperature of 482° C. Table 1 shows the obtained results.

Comparative Example 1

Preparation of Polyimide

A colorless transparent film made of a polyimide (100 mm in length, 100 mm in width, and 50 μm in thickness) was obtained by employing the same method as that in the polyimide preparation step employed in Example 1, except that the norbornane-2-spiro-α-cyclopentanone-α'-spiro-2"-norbornane-5,5",6,6'-tetracarboxylic dianhydride (the mixture of six isomers) obtained in Synthesis Example 3, as it was, was used instead of the second compound. Note that the intrinsic viscosity [η] of a polyamic acid, which was a reaction intermediate obtained in conducting the polyimide preparation step, was 0.67.

Figure 25:
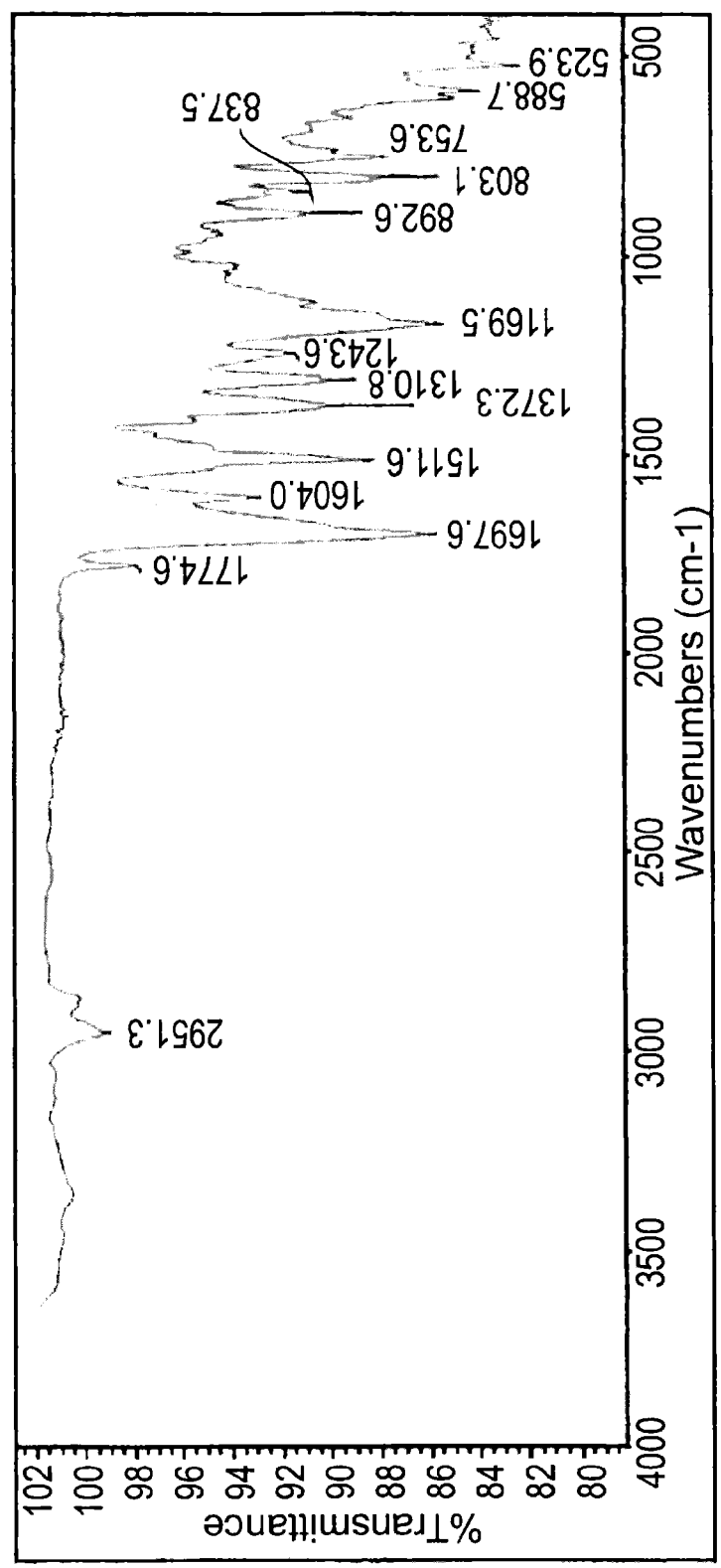
FIG. 25 is a graph showing an IR spectrum of a compound (polyimide) obtained in a polyimide preparation step employed in Comparative Example 1.

An IR spectrum of the compound constituting the thus obtained film was measured. FIG. 25 shows the IR spectrum of the obtained compound. As is apparent from the results shown in FIG. 25, C=O stretching vibration of imidocarbonyl was observed at 1697.6 cm$^{-1}$ for the obtained compound, and the obtained compound was confirmed to be a polyimide. In addition, the polyimide forming the obtained film was found to be a polyimide comprising the repeating units represented by the general formulae (1) and (2) in an amount of 79% by mole relative to all the repeating units on the basis of the kinds of the monomer used (the norbornane-2-spiro-α-cyclopentanone-α'-spiro-2"-norbornane-5,5',6,6'-tetracarboxylic dianhydride obtained in Synthesis Example 3 (the mixture of six isomers) and the aromatic diamine compound (4,4'-diaminobenzanilide)). Moreover, the characteristics of the polyimide were evaluated by using the thus obtained film made of the polyimide in the same manner as described above. The results showed that the polyimide had a linear expansion coefficient of 19 ppm/° C., a glass transition temperature of 369° C., and a 5% weight loss temperature of 481° C. Table 1 shows the obtained results.

TABLE 1

|  | Example 1 | Example 2 | Example 3 | Example 4 | Comparative Example 1 |
|---|---|---|---|---|---|
| Type of tetracarboxylic dianhydride | Mixture of two isomers | Mixture of two isomers | Mixture of six isomers | Mixture of six isomers | Mixture of six isomers |
| Content ratio of trans-endo-endo-isomer and cis-endo-endo-isomer in tetracarboxylic dianhydride | 99% by mole | 99% by mole | 95% by mole | 90% by mole | 79% by mole |
| Mole ratio of trans-endo-endo-isomer and cis-endo-endo-isomer ([trans-isomer]:[cis-isomer]) | 63:37 | 64:36 | 63:37 | 63:37 | 63:37 |
| Intrinsic viscosity (η) of polyamic acid (unit: dL/g) | 0.93 | 0.94 | 0.88 | 0.82 | 0.67 |
| Total luminous transmittance (unit: %) | 87.4 | 87.5 | 87.3 | 87.2 | 87.1 |
| Refractive index | 1.631 | 1.631 | 1.632 | 1.632 | 1.632 |
| Glass transition temperature (unit: ° C.) | 371 | 372 | 370 | 370 | 369 |
| 5% weight loss temperature (unit: ° C.) | 482 | 483 | 482 | 482 | 481 |
| Linear expansion coefficient (unit: ppm/° C.) | 10 | 9 | 12 | 14 | 19 |
| Film thickness (unit: μm) | 50 | 50 | 50 | 50 | 50 |

As is apparent from the results shown in Table 1, it was found that each of the polyimides of the present invention obtained in Examples 1 to 4 had a linear expansion coefficient of 15 ppm/° C. or less and a glass transition temperature (Tg) of 350° C. or above, and also that the film formed of each of the polyimides obtained in Examples 1 to 4 had a sufficiently high transparency. Note that, as is apparent from the description of the production method and the like shown above, it was also found that the polyimides of the present invention obtained in Examples 1 to 4 were produced under generally employable polymerization conditions, and were sufficiently highly practical from the industrial viewpoint and the like. From these results, it was found that each of the polyimides of the present invention (Examples 1 to 4) was capable of exhibiting characteristics such as the sufficiently low linear expansion coefficient and the sufficiently high glass transition temperature (Tg) at sufficiently high levels in a well-balanced manner, and thereby it is found that each of the polyimides of the present invention (Examples 1 to 4) has sufficiently excellent heat shock resistance (resistance to change in the surrounding temperature).

INDUSTRIAL APPLICABILITY

As described above, according to the present invention, it is possible to provide a polyimide which is excellent in light transmittance and heat resistance and has a sufficiently low linear expansion coefficient, as well as an alicyclic tetracarboxylic dianhydride used for producing the polyimide.

Accordingly, the polyimide of the present invention has a sufficiently high heat resistance and an extremely low linear expansion coefficient, and hence is particularly useful as, for example, a material for forming a substrate film on which a transparent electrode of a touch panel or a solar cell is to be stacked and a material for forming a substrate film on which a transparent electrode of a display device (an organic EL display device, a liquid crystal display device, or the like) is to be stacked, as well as a material for forming films used in the applications such as FPCs, optical waveguides, image sensors, reflection plates for LEDs, covers for LED illumination, skeleton-type FPCs, coverlay films, chip-on-films, high-ductility composite substrates, liquid crystal orientation films, polyimide coating materials (buffer coating materials for DRAMs, flash memories, next generation LSIs, and the like), resists for semiconductors, and various electrical materials, a material for various batteries such as lithium ion batteries, and the like.

The invention claimed is:

1. A polyimide comprising at least one of repeating units represented by the following general formulae (1) and (2):

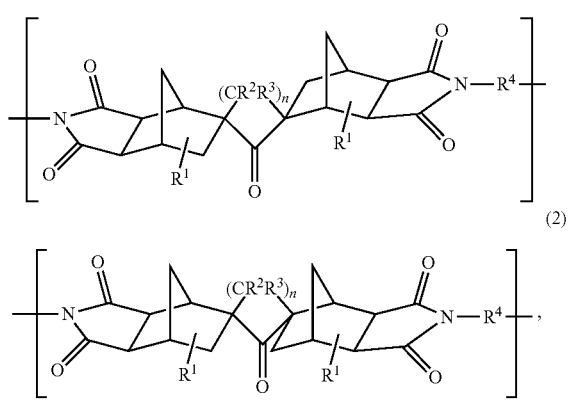

wherein
the formulae (1) and (2), $R^1$, $R^2$, and $R^3$ each independently represent one selected from the group consisting of a hydrogen atom, alkyl groups having 1 to 10 carbon atoms, and a fluorine atom, $R^4$ represents an aryl group having 6 to 40 carbon atoms, and n represents an integer of 0 to 12, and
wherein as to the polyimide comprising at least one of repeating cis-endo-endo and trans-endo-endo units, a total amount of those repeating units represented by the general formulae (1) and (2) is 90% by mole or more relative to all repeating units.

2. The polyimide according to claim 1, wherein $R^4$ in the general formulae (1) and (2) is one of groups represented by the following general formulae (3) to (6):

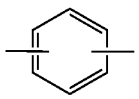

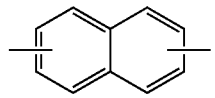

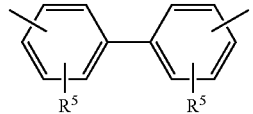

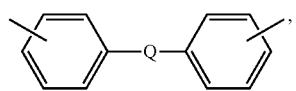

wherein the formula (5), $R^5$ represents one selected from the group consisting of a hydrogen atom, a fluorine atom, a methyl group, an ethyl group, and a trifluoromethyl group, and in the formula (6), Q represents one selected from the group consisting of groups represented by the formulae: —O—, —S—, —CO—, —CONH—, —$C_6H_4$—, —COO—, —$SO_2$—, —$C(CF_3)_2$—, —$C(CH_3)_2$—, —$CH_2$—, —O—$C_6H_4$—$C(CH_3)_2$—$C_6H_4$—O—, —O—$C_6H_4$—$SO_2$—$C_6H_4$—O—, —$C(CH_3)_2$—$C_6H_4$—$C(CH_3)_2$—, —O—$C_6H_4$—$C_6H_4$—O—, and —O—$C_6H_4$—O—.

3. The polyimide according to claim 1, wherein the polyimide has a linear expansion coefficient of 15 ppm/° C. or less, the linear expansion coefficient being determined by measuring change in length under a nitrogen atmosphere under a condition of a rate of temperature rise of 5° C./minute in a temperature range from 50° C. to 200° C.

4. The polyimide according to claim 1, wherein the total amount of the repeating units represented by the general formulae (1) and (2) is 95 to 100% by mole relative to all the repeating units.

5. An alicyclic tetracarboxylic dianhydride used for production of the polyimide according to claim 1, the alicyclic tetracarboxylic dianhydride comprising at least one of trans-endo-endo-norbornane-2-spiro-α-cycloalkanone-α'-spiro-2''-norbornane-5,5'',6,6''-tetracarboxylic dianhydrides represented by the following general formula (7):

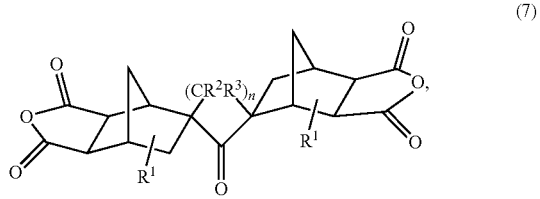

wherein the formula (7), $R^1$, $R^2$, $R^3$, and n have the same meanings as those of $R^1$, $R^2$, $R^3$, and n in the general formulae (1) and (2) and
the cis-endo-endo-norbornane-2-spiro-α-cycloalkanone-α'-spiro-2''-norbornane-5,5'',6,6''-tetracarboxylic dianhydrides represented by the following general formula (8):

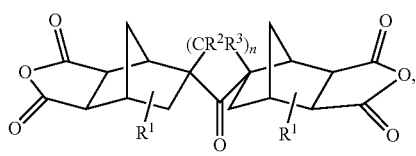
(8)

wherein
the formula (8), $R^1$, $R^2$, $R^3$, and n have the same meanings as those of $R^1$, $R^2$, $R^3$, and n in the general formulae (1) and (2), and
a total amount of the alicyclic tetracarboxylic dianhydrides represented by the general formulae (7) and (8) is 90% by mole or more.

6. A polyamic acid comprising at least one of repeating units represented by the following general formulae (15) and (16):

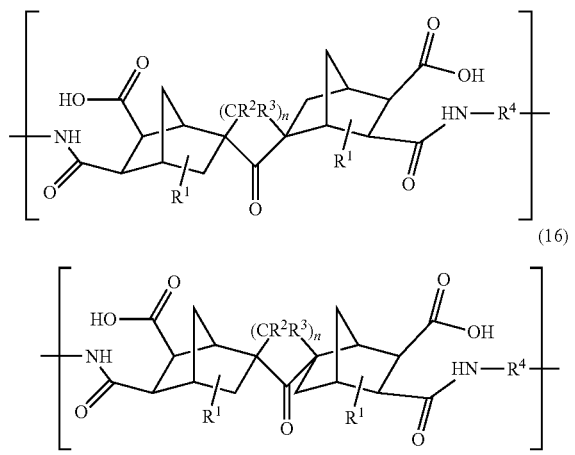

wherein the formulae (15) and (16), $R^1$, $R^2$ and $R^3$ each independently represent one selected from the group consisting of a hydrogen atom, alkyl groups having 1 to 10 carbon atoms, and a fluorine atom, $R^4$ represents an aryl group having 6 to 40 carbon atoms, and n represents an integer of 0 to 12, and wherein as to the polyamic acid comprising at least one of repeating cis-endo-endo and trans-endo-endo units, a total amount of those repeating units represented by the general formulae (15) and (16) is 90% by mole or more relative to all repeating units.

7. A polyamic solution comprising the polyamic acid according to claim 6, and an organic solvent.

8. A polyimide solution comprising the polyimide according to claim 1, and an organic solvent.

9. A film comprising the polyimide according to claim 1.

10. A substrate comprising the polyimide according to claim 1.

11. A liquid crystal orientation film comprising the polyimide according to claim 1.

12. A flexible printed wiring board comprising the polyimide according to claim 1.

13. A polyimide coating material comprising the polyimide according to claim 1.

14. A reflection plate comprising the polyimide according to claim 1.

15. A coating film comprising the polyimide according to claim 1.

* * * * *